(12) United States Patent
Watts et al.

(10) Patent No.: US 8,530,207 B2
(45) Date of Patent: Sep. 10, 2013

(54) PHOTOSYNTHETIC MICROORGANISMS COMPRISING EXOGENOUS PROKARYOTIC ACYL-ACP THIOESTERASES AND METHODS FOR PRODUCING FATTY ACIDS

(75) Inventors: Kevin Watts, Minneapolis, MN (US); Rekha Seshadri, San Diego, CA (US); Toby Richardson, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/324,623

(22) Filed: Dec. 13, 2011

(65) Prior Publication Data

US 2012/0164700 A1 Jun. 28, 2012

Related U.S. Application Data

(60) Provisional application No. 61/426,555, filed on Dec. 23, 2010.

(51) Int. Cl.
*C12P 7/64* (2006.01)
*C12N 1/00* (2006.01)
*C12N 1/12* (2006.01)
*C12N 1/20* (2006.01)

(52) U.S. Cl.
USPC ...... 435/134; 435/243; 435/257.2; 435/252.3

(58) Field of Classification Search
None
See application file for complete search history.

(56) References Cited

U.S. PATENT DOCUMENTS

| | | | |
|---|---|---|---|
| 5,447,858 A | 9/1995 | Key et al. | 435/172.3 |
| 5,451,513 A | 9/1995 | Maliga et al. | 435/172.3 |
| 5,455,167 A | 10/1995 | Voelker et al. | 435/172.3 |
| 5,545,817 A | 8/1996 | McBride et al. | 800/205 |
| 5,545,818 A | 8/1996 | McBride et al. | 800/205 |
| 5,639,952 A | 6/1997 | Quail et al. | 800/205 |
| 5,654,495 A | 8/1997 | Voelker et al. | 800/250 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,851,796 A | 12/1998 | Schatz | 435/69.1 |
| 6,379,945 B1 | 4/2002 | Jepson et al. | 435/243 |
| 6,410,828 B1 | 6/2002 | Armstrong et al. | 800/287 |
| 7,135,290 B2 | 11/2006 | Dillon | 435/6 |
| 7,294,506 B2 | 11/2007 | Daniell et al. | 435/320.1 |
| 2009/0298143 A1 | 12/2009 | Roessler et al. | 435/134 |
| 2011/0020883 A1 | 1/2011 | Roessler et al. | 435/134 |

FOREIGN PATENT DOCUMENTS

| | | |
|---|---|---|
| WO | WO 95/16783 | 6/1995 |
| WO | WO 00/62601 | 10/2000 |
| WO | WO 03/091413 | 11/2003 |
| WO | WO 2005/005643 | 1/2005 |
| WO | WO 2007/133558 | 11/2007 |
| WO | WO 2007/136762 | 11/2007 |
| WO | WO 2008/100251 | 8/2008 |
| WO | WO 2008/119082 A2 * | 10/2008 |
| WO | WO 2008/151149 | 12/2008 |
| WO | WO 2009/036385 | 3/2009 |
| WO | WO 2009/076559 | 6/2009 |
| WO | WO 2009/111513 | 9/2009 |
| WO | WO 2010/019813 | 2/2010 |
| WO | WO 2010/022090 | 2/2010 |
| WO | WO 2010/118410 | 10/2010 |

OTHER PUBLICATIONS

Pfam family Acyl-ACP_TE (PF01643), obtained from pfam.sanger.ac.uk/family/PF01643 on Jul. 17, 2012, 3 pages.*
GenBank Accession No. ABK74560, Dec. 2006, 1 page.*
GenBank Accession No. EFB38222, Dec. 2009, 2 pages.*
Abe, J., et al. (2008), "Expression of exogenous genes under the control of endogenous HSP70 and CAB promoters in the closterium peracerosum-strigosum-littorale complex", *Plant Cell Physiol*, 49(4): 625-632.
Altschul, S., et al. (1997), "Gapped BLAST and PSI-BLAST: a new generation of protein database search programs", *Nucleic Acids Research*, 25(17): 3389-3402.
Angermayr, A., et al. (2009), "Energy biotechnology with cyanobacteria", *Current Opinion in Biotechnology*, 20: 257-263.
Bateman, A., et al. (2000), "The pfam protein families database", *Nucleic Acids Research*, 28(1):263-266.
Bateman, A., et al. (2004), "The pfam protein families database", *Nucleic Acids Research*, 32: Database Issue: D138-D141.
Browse, J., et al. (1991), "Glycerolipid synthesis, biochemistry and regulation", *Plant Molecular Biology*, 42: 467-506.
Cantu, D., et al. (2010), "Thioesterases: A new perspective based on their primary and tertiary structures", *Protein Science*, 19:1281-1295.
Chan, D., et al. (2010), "Current understanding of fatty acid biosynthesis and the acyl carrier protein", *Biochem J*. 430:1-19.
Copeland, A., et al. (2007), "*Clostridium thermocellum* ATCC 27405, complete genome", *Genbank Accession CP000568.1* [Retrieved on Mar. 21, 2012]. Retrieved from the internet at <URL: http://www.ncbi.nlm.nih.gov/nuccore/125712750?sat=11 &satkey=9897002>.
Davies, H., (1993), "Medium chain ACYL-ACP Hydrolysis Activities of Developing Oilseeds" *Phytochemistry* 33 (6):1353-1356.
Dillon, S., et al. (2004), "The hotdog fold: wrapping up a superfamily of thioesterases and dehydratases" *BMC Bioinformatics*, 5:109.
Dörmann, P., et al. (1994), "Specificities of the acyl-acyl carrier protein (ACP) thioesterase and glycerol-3-phosphate acyltransferase for octadecenoyl-ACP isomers" *Plant Physiol*. 104:839-844.

(Continued)

*Primary Examiner* — David J Steadman
(74) *Attorney, Agent, or Firm* — Harness, Dickey & Pierce, P.L.C.

(57) ABSTRACT

The described invention provides genetically engineered photosynthetic microorganisms expressing prokaryotic acyl-ACP thioesterases and methods of using the genetically engineered photosynthetic microorganisms for producing free fatty acids and/or fatty acid derivatives.

21 Claims, 5 Drawing Sheets

(56) References Cited

OTHER PUBLICATIONS

Finn, R., et al. (2006), "Pfam: clans, web tools and services", *Nucleic Acids Research*, 34: Database Issue 34:D247-D251.
Finn, R., et al. (2010), "The pham protein families database", *Nucleic Acids Research*, 38: Database Issue 38:D211-D222.
Gibson, S., et al. (1994), "Use of transgenic plants and mutants to study the regulation and function of lipid composition" *Plant, Cell and Environment*, 17:627-637.
Hallmann, A., et al. (1997), "Gene replacement by homologous recombination in the multicellular green alga *Volvox carteri*" *Proc. Natl. Acad. Sci USA*, 94:7469-7474.
Henikoff, S., et al. (1992), "Amino acid substitution matrices from protein blocks", *Proc. Natl. Acad. Sci USA*, 89:10915-10919.
Ikawa, M., et al. (1994), "Lipids of cyanobacterium aphanizomenon flos-aquae and inhibition of chlorella growth" *Journal of Chemical Ecology*. 20(9):2429-2436.
International Search Report for PCT/US11/64646 dated Apr. 11, 2012.
Iwai, M., et al. (2004), "Improved genetic transformation of the thermophilic cyanobacterium, *Thermosynechoccus elongates* BP-1", *Plant Cell Physiol.* 45(2):171-175.
Jones, A., et al. (1995), "Palmitoyl-acyl carrier protein (ACP) thioesterase and the evolutionary origin of platn acyl-ACP Thioesterases" *The Plant Cell* 7:359-371.
Kindle, K., et al. (1989), "Stable nuclear transformation of *Chlamydomonas* using the *Chlamydomonas* gene for nitrate reductase", *The Journal of Cell Biology*, 109 (6, Part 1), 2589-2601.
Knutzon, D., et al. (1992), "Isolation of characterization of two safflower oleoyl-acyl carrier protein thioesterase cDNA clones", *Plant Physiol.* 100:1751-1758.
Löhden, I., et al. (1988), "Role of plastidial acyl-acyl carrier protein: Glycerol 3-phosphate acyltransferase and acyl-acyl carrier protein hydrolase in channeling the acyl flux through the prokaryotic and eukaryotic pathway", *Planta* 176:506-512.
Mayer, K., et al. (2005), "A structural model of the plant acyl-acyl carrier protein thioesterase fatB comprises two helix/4-stranded sheet domains, the N-terminal domain containing residues that affect specificity and the C-terminal domain containing catalytic residues" *The Journal of Biological Chemistry*, 280(5):3621-3627.
Mayer, K., et al. (2007), "Identification of amino acid residues involved in substrate specificity of plant acyl-ACP thioesterases using a bioinformatics-guided approach", *BMC Plant Biology*, 7:1-11.
McBride, K., et al. (1994), "Controlled expression of plastid transgenes in plants based on a nuclear DNA-encoded and plastid-targeted T7 RNA polymerase" *Proc. Natl. Acad. Sci. USA*, 91:7301-7305.
Méndez-Alvarez, S., et al. (1994), "Transformation of *Chlorobium limicola* by a plasmid that confers the ability to utilize thiosulfate" *Journal of Bacteriology*,176(23):7395-7397.
Murata, N., et al. (1995), "Acyl-lipid desaturases and their importance in the tolerance and acclimatization to cold of cyanobacteria" *Biochem J.* 308:1-8.
Ohnuma M., et al. (2008), "Polyethylene glycol (PEG)-mediated transient gene expression in a red alga, *Cyanidioschyzon merolae* 10D", *Plant Cell Physiol.* 49(1):117-120.
Pearson W., et al. (1988), "Improved tools for biological sequence comparison" *Proc. Natl. Acad. Sci. USA*, 85:2444-2448.
Perrone, C., et al. (1998), "The *Chlamydomonas* IDA7 locus encodes a 140 kDa dynein intermediate chain required to assemble the I1 inner arm complex", *Molecular biology of the Cell*, 9:3351-3365.
Ramesh, V., et al. (2004), "A simple method for chloroplast transformation in *Chlamydomonas reinhardtii*" *Methods in Molecular Biology*, 274:301-307.
Ravindran, C., et al. (2006), "Electroporation as a tool to transfer the plasmid pRL489 in *Oscillatoria* MKU 277" *Journal of Microbiological Methods*, 66:174-176.
Schroda, M., et al. (2000), "The HSP70A promoter as a tool for improved expression of transgenes in *Chlamydomonas*", *The plant journal* 21(2):121-131.
Schweizer, E., et al. (2004), "Microbial Type I Fatty Acid Synthases (FAS): major players in a network of Cellular FAS systems", *Microbiology and molecular biology reviews* 68(3):501-517.
Smith, T., et al., (1981), "Comparison of biosequences", *Advances in Applied Mathematics* 2:482-489.
Sonnhammer, E., et al. (1998), "Pfam: multiple sequence alignments and HMM-profiles of protein domains" *Nucleic Acids Research* 26(1):320-322.
Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.
Tan, C., et al. (2005), "Establishment of a micro-particle bombardment transformation system for *Dunaliella salina*", *The Journal of Microbiology* 43:361-365.
Voelker, T., et al. (1994), "Alteration of the specificity and regulation of fatty acid synthesis of *Escherichia coli* by expression of a plant medium-chain acyl-acyl carrier protein thioesterase" *Journal of Bacteriology* 176(23):7320-7327.
Xu, J., et al. (2007) "Evolution of Symbiotic Bacteria in the Distal Human Intestine" *Uniprot* A6LDN7_9PORP [Retrieved on Mar. 21, 2012]. Retrieved from the internet at <URL: http://www.uniprot.org/uniprot/A6LDN7.txt?version=1>.
Li, J., et al. (2000) "Mutation of the nucleophilic elbow of the lux-specific thioesterase from *Vibrio harveyi*" Biochemical and Biophysical Research Communications, 275:704-708.

\* cited by examiner

SEQUENCE LISTING

<160> NUMBER OF SEQ ID NOS: 30

<210> SEQ ID NO 1
<211> LENGTH: 241
<212> TYPE: PRT
<213> ORGANISM: Parabacteroides distasonis

<400> SEQUENCE: 1

Met Glu Lys Val Gly Leu Phe His Phe Val Ala Glu Pro Tyr Leu Met
1               5                   10                  15

Asp Phe Arg Gly Arg Val Thr Leu Pro Met Ile Gly Asn Tyr Leu Ile
            20                  25                  30

His Ala Ala Ser Ser His Ala Gly Glu Arg Gly Phe Gly Phe Asn Asp
        35                  40                  45

Met Ser Glu Arg His Thr Ala Trp Val Leu Ser Arg Leu Ala Ile Glu
 50                  55                  60

Met Lys Glu Tyr Pro Thr Ala Phe Asp Lys Ile Asn Leu Tyr Thr Trp
65                  70                  75                  80

Ile Asp Glu Val Gly Arg Leu Phe Thr Ser Arg Cys Phe Glu Leu Ala
                85                  90                  95

Asp Glu Asn Gly Lys Thr Phe Gly Phe Ala Arg Ser Ile Trp Ala Ala
            100                 105                 110

Ile Asp Val Glu Thr Arg Arg Pro Thr Leu Leu Asp Ile Glu Ala Leu
        115                 120                 125

Gly Lys Tyr Ile Asp Glu Arg Pro Cys Pro Ile Glu Lys Pro Gly Lys
130                 135                 140

Ile Met Pro Ala Glu Asn Lys Ala Glu Gly Ile Pro Tyr Ser Ile Lys
145                 150                 155                 160

Tyr Ser Asp Leu Asp Ile Asn Gly His Phe Asn Ser Val Lys Tyr Ile
                165                 170                 175

Glu His Leu Leu Asp Leu Phe Asp Ile Asp Gln Phe Lys Thr Arg Glu
            180                 185                 190

Ile Gly Arg Leu Glu Ile Ala Tyr Gln Ser Glu Gly Lys Gln Gly Met
        195                 200                 205

Pro Leu Thr Leu His Lys Ala Glu Ser Asp Pro Asp Lys Gln Asp Met
210                 215                 220

Ala Ile Cys His Glu Gly Lys Ala Ile Cys Arg Ala Ala Val Thr Trp
225                 230                 235                 240

Arg

<210> SEQ ID NO 2
<211> LENGTH: 253
<212> TYPE: PRT
<213> ORGANISM: Clostridium thermocellum

<400> SEQUENCE: 2

Met Gln Lys Lys Arg Phe Ser Lys Lys Tyr Glu Val His Tyr Tyr Glu
1               5                   10                  15

Ile Asn Ser Met Gln Glu Ala Thr Leu Leu Ser Leu Leu Asn Tyr Met
            20                  25                  30

Glu Asp Cys Ala Ile Ser His Ser Thr Ser Ala Gly Tyr Gly Val Asn
        35                  40                  45

Glu Leu Leu Ala Ala Asp Ala Gly Trp Val Leu Tyr Arg Trp Leu Ile
 50                  55                  60

Lys Ile Asp Arg Leu Pro Lys Leu Gly Glu Thr Ile Thr Val Gln Thr
65                  70                  75                  80

Trp Ala Ser Ser Phe Glu Arg Phe Tyr Gly Asn Arg Glu Phe Ile Val
                85                  90                  95

Leu Asp Gly Arg Asp Asn Pro Ile Val Lys Ala Ser Ser Val Trp Ile
            100                 105                 110

Tyr Phe Asn Ile Lys Lys Arg Lys Pro Met Arg Ile Pro Leu Glu Met
        115                 120                 125

Gly Asp Ala Tyr Gly Ile Asp Glu Thr Arg Ala Leu Glu Glu Pro Phe
130                 135                 140

```
Thr Asp Phe Asp Phe Asp Phe Glu Pro Lys Val Ile Glu Glu Phe Thr
145                 150                 155                 160

Val Lys Arg Ser Asp Ile Asp Thr Asn Ser His Val Asn Asn Lys Lys
                165                 170                 175

Tyr Val Asp Trp Ile Met Glu Thr Val Pro Gln Gln Ile Tyr Asp Asn
            180                 185                 190

Tyr Lys Val Thr Ser Leu Gln Ile Ile Tyr Lys Lys Glu Ser Ser Leu
            195                 200                 205

Gly Ser Gly Ile Lys Ala Gly Cys Val Ile Asp Glu Gln Asn Thr Asp
            210                 215                 220

Asn Pro Arg Leu Leu His Lys Ile Trp Asp Lys Asn Thr Gly Leu Glu
225                 230                 235                 240

Leu Val Ser Ala Glu Thr Ile Trp Gln Lys Ile Gln Ser
                245                 250
```

<210> SEQ ID NO 3
<211> LENGTH: 726
<212> TYPE: DNA
<213> ORGANISM: Artificial Sequence
<220> FEATURE:
<223> OTHER INFORMATION: Parabacteroides distasonis thioesterase gene codon-optimized for expression in Synechocystis

<400> SEQUENCE: 3

```
atggaaaaag tgggtctgtt ccactttgtc gcggagccgt acctcatgga cttccgtggg    60
cgcgtaaccc tacccatgat cggtaactac ctgattcacg ccgcctcctc ccatgccggc   120
gaacggggct ttgggttcaa tgatatgtcc gagcgccata ccgcatgggt gttatcccgc   180
ttggcgattg agatgaagga gtaccccgac cgcgttcgac agatcaacct ctacacctgg   240
attgatgaag tgggccgact cttcacttcc cgttgtttcg agttggccga cgaaaatggc   300 aaaaccttg gcttcgcccg gtccatctgg gctgccattg atgtggaaac gcgacggccg   360
accttgttgg atattgaggc cttgggcaag tatatcgacg agcggccctg tcccatcgag   420
aaaccgggca agattatgcc tgcggaaaac aaagcagaag gcatcccgta ctccattaag   480
tactccgacc tcgacatcaa cgggcacttc aacagcgtca agtacatcga acacctgctc   540
gacctgtttg acatcgacca gttcaagaca cgcgaaatcg gtcggttgga gatcgcctac   600
caatccgaag gcaagcaagg tatgcccttg acgttacata aggccgagag cgacccggat   660
aaacaagaca tggcaatctg ccacgagggt aaagccatct gtcgggcagc cgtgacctgg   720
cggtaa                                                             726
```

<210> SEQ ID NO 4
<211> LENGTH: 762
<212> TYPE: DNA
<213> ORGANISM: Artificial Sequence
<220> FEATURE:
<223> OTHER INFORMATION: Clostridium thermocellum acyl-ACP thioesterase gene codon-optimized for expression in Synechocystis

<400> SEQUENCE: 4

```
atgcaaaaaa agcggttcag caagaagtac gaggtccact actacgagat caacagcatg    60
caggaagcca ccttgctgtc tctcctcaac tacatggagg actgcgccat cagccattcc   120
accagtgccg gctatggcgt gaatgaattg ttggccgcgg acgcggggtg ggtgttgtac   180
cggtggctga tcaagattga ccgcttgccc aagctcggag aaaccatcac cgtgcaaacc   240
tgggcctcct cctttgaacg cttctatggc aaccgagagt tcatcgtgct ggacggcgc   300 gacaaccca ttgtgaaggc gagcagcgtc tggatctact tcaacatcaa gaagcgcaag   360
```

```
cccatgcgga tccccctaga gatgggcgac gcctacggca ttgatgagac ccgagccctg      420
gaggagccgt tcacggattt tgacttcgac ttcgagccca aggtgatcga ggagttcacc      480
gtcaagcgca gtgacattga caccaactcc cacgtgaaca acaagaaata cgtcgactgg      540
atcatggaga cggtacccca acaaatctat gacaattaca aggtcacgtc cctgcagatc      600
atctacaaga aggagagtag cctcggcagc gggattaaag ccgggtgcgt catcgacgaa      660
cagaatacgg acaatccgcg cctgctccac aagatctggg ataaaaacac gggcctcgag      720
ctagtgtccg ccgagaccat ttggcagaaa attcagtcct aa                         762

<210> SEQ ID NO 5
<211> LENGTH: 31
<212> TYPE: DNA
<213> ORGANISM: Artificial Sequence
<220> FEATURE:
<223> OTHER INFORMATION: Forward primer for amplifying RS2 from
      Synechocystis

<400> SEQUENCE: 5
gggccctatt tgcccgtatt ctgccctatc c                                      31

<210> SEQ ID NO 6
<211> LENGTH: 32
<212> TYPE: DNA
<213> ORGANISM: Artificial Sequence
<220> FEATURE:
<223> OTHER INFORMATION: Reverse primer for amplifying RS2 from
      Synechocystis

<400> SEQUENCE: 6
gggcccgact gcctttggtg gtattaccga tg                                     32

<210> SEQ ID NO 7
<211> LENGTH: 70
<212> TYPE: DNA
<213> ORGANISM: Artificial Sequence
<220> FEATURE:
<223> OTHER INFORMATION: Forward primer for amplifying the trcY promoter

<400> SEQUENCE: 7
actagtcctg aggctgaaat gagctgttga caattaatca tccggctcgt ataatgtgtg      60
gaattgtgag                                                              70

<210> SEQ ID NO 8
<211> LENGTH: 70
<212> TYPE: DNA
<213> ORGANISM: Artificial Sequence
<220> FEATURE:
<223> OTHER INFORMATION: Reverse primer for amplifying the trcY promoter

<400> SEQUENCE: 8
ccatggtttt tttcctcctt agtgtgaaat tgttatccgc tcacaattcc acacattata      60
cgagccggat                                                              70

<210> SEQ ID NO 9
<211> LENGTH: 90
<212> TYPE: DNA
<213> ORGANISM: Artificial Sequence
<220> FEATURE:
<223> OTHER INFORMATION: trcY promoter sequence

<400> SEQUENCE: 9
ctgaaatgag ctgttgacaa ttaatcatcc ggctcgtata atgtgtggaa ttgtgagcgg      60
```
ataacaattt cacactaagg aggaaaaaaa                                  90

<210> SEQ ID NO 10
<211> LENGTH: 36
<212> TYPE: DNA
<213> ORGANISM: Artificial Sequence
<220> FEATURE:
<223> OTHER INFORMATION: Forward primer for cloning the codon-optimized
      Parabacteroides distasonis thioesterase gene

<400> SEQUENCE: 10
aggaaaaaaa ccatgatgga aaaagtgggt ctgttc                           36

<210> SEQ ID NO 11
<211> LENGTH: 42
<212> TYPE: DNA
<213> ORGANISM: Artificial sequence
<220> FEATURE:
<223> OTHER INFORMATION: Reverse primer for cloning the codon-optimized
      Parabacteroides distasonis thioesterase gene

<400> SEQUENCE: 11
cctgcagata tctagattac cgccaggtca cggctgcccg ac                    42

<210> SEQ ID NO 12
<211> LENGTH: 39
<212> TYPE: DNA
<213> ORGANISM: Artificial sequence
<220> FEATURE:
<223> OTHER INFORMATION: Forward primer for cloning the codon-optimized
      Clostridium thermocellum acyl-ACP thioesterase gene

<400> SEQUENCE: 12
aggaaaaaaa ccatgatgca aaaaaagcgg ttcagcaag                        39

<210> SEQ ID NO 13
<211> LENGTH: 41
<212> TYPE: DNA
<213> ORGANISM: Artificial sequence
<220> FEATURE:
<223> OTHER INFORMATION: Reverse primer for cloning the codon-optimized
      Clostridium thermocellum acyl-ACP thioesterase gene

<400> SEQUENCE: 13
cctgcagata tctagattag gactgaattt tctgccaaat g                     41

<210> SEQ ID NO 14
<211> LENGTH: 7646
<212> TYPE: DNA
<213> ORGANISM: Artificial sequence
<220> FEATURE:
<223> OTHER INFORMATION: pYC expression construct with the codon-
      optimized Parabacteroides distasonis thioesterase gene

<400> SEQUENCE: 14
cagttaccaa tgcttaatca gtgaggcacc tatctcagcg atctgtctat ttcgttcatc    60
catagttgcc tgactcccg tcgtgtagat aactacgata cgggagggct taccatctgg    120
ccccagtgct gcaatgatac cgcgagaccc acgctcaccg gctccagatt tatcagcaat    180
aaaccagcca gccggaaggg ccgagcgcag aagtggtcct gcaactttat ccgcctccat    240
ccagtctatt aattgttgcc gggaagctag agtaagtagt tcgccagtta atagtttgcg    300
caactgttgg gaagggcgat cggtgcgggc ctcttcgcta ttacgccagc tggcgaaagg    360
gggatgtgct gcaaggcgat taagttgggt aacgccaggg ttttcccagt cacgacgttg    420

```
taaaacgacg gccagtgaat tgggcccgac tgcctttggt ggtattaccg atgagtggca   480
cgttattttc accgctctgg ccgtgttgag catggtgctg ggcaacgtgg tggctttagc   540
ccaaaccagc atgaaacgga tgttggccta ctcttccatc ggtcaagcag gctttgtgat   600
gattggccta gtggccggca gtgaagatgg ttacgccagc atggttttct acatgctcat   660
ctatctgttt atgaacctgg gggcgtttag ttgcattatt ctcttcaccc tccgcactgg   720
cagtgaccaa attagtgatt acgctggtct gtaccacaaa gacccttgt taaccttggg   780
cttgagcatt tgtttattat ccttgggggg cattcctcct ctggcgggct ttttcggcaa   840
aatttacatc ttctgggccg gttggcaatc gggattgtat ggcctagtcc tacttggtct   900
ggttaccagt gtagtttcca tctactacta catccgggtg gtgaaaatga tggtggtgaa   960
ggagccccag gaaatgtccg aagtaatcaa aaattacccg ccatcaaat ggaatttacc  1020
cggcatgcgt cccctacagg tgggcattgt cgctactttg gttgctacct cgctggcagg  1080
tattctggct aatcccctct ttaacctcgc caccgattcc gtggtcagca ccaagatgtt  1140
gcagacagcc ctccagcaaa caggagaaac tccggcgatc gccatttccc atgatttacc  1200
ctaggggtat caggaaatat tgctttgcag gcaaaagcca atgagtgtaa ctatagaaac  1260
cgatttaaag gagatccact agtcctgagg ctgaaatgag ctgttgacaa ttaatcatcc  1320
ggctcgtata atgtgtggaa ttgtgagcgg ataacaattt cacactaagg aggaaaaaaa  1380
catgatggaa aaagtgggtc tgttccactt tgtcgcggag ccgtacctca tggacttccg  1440
tgggcgcgta accctaccca tgatcggtaa ctacctgatt cacgccgcct cctcccatgc  1500
cggcgaacgg ggctttgggt tcaatgatat gtccgagcgc ataccgcat gggtgttatc  1560
ccgcttggcg attgagatga aggagtaccc gaccgcgttc gacaagatca acctctacac  1620
ctggattgat gaagtgggcc gactcttcac ttcccgttgt ttcgagttgg ccgacgaaaa  1680
tgcaaaacc tttggcttcg cccggtccat ctgggctgcc attgatgtgg aaacgcgacg  1740
gccgaccttg ttggatattg aggccttggg caagtatatc gacgagcggc cctgtcccat  1800
cgagaaaccg ggcaagatta tgcctgcgga aaacaaagca gaaggcatcc cgtactccat  1860
taagtactcc gacctcgaca tcaacgggca cttcaacagc gtcaagtaca tcgaacacct  1920
gctcgacctg tttgacatcg accagttcaa gacacgcgaa atcggtcggt tggagatcgc  1980
ctaccaatcc gaaggcaagc aaggtatgcc cttgacgtta cataaggccg agagcgaccc  2040
ggataaacaa gacatggcaa tctgccacga gggtaaagcc atctgtcggg cagccgtgac  2100
ctggcggtaa tctagatatc tgcaggccta agctttatgc ttgtaaaccg ttttgtgaaa  2160
aaattttaa aataaaaaag gggacctcta gggtccccaa ttaattagta atataatcta  2220
ttaaaggtca ttcaaaaggt catccaccgg atcaattccc ctgctcgcgc aggctgggtg  2280
ccaggcccga tccttggagc ccttgccctc ccgcacgatg atcgtgccgt gatcgaaatc  2340
cagatccttg acccgcagtt gcaaacccctc actgatccgc atgcccgttc catacagaag  2400
ctgggcgaac aaacgatgct cgccttccag aaaaccgagg atgcgaacca cttcatccgg  2460
ggtcagcacc accggcaagc gccgcgacgg ccgaggtctt ccgatctcct gaagccaggg  2520
cagatccgtg cacagcacct tgccgtagaa gaacagcaag gccgccaatg cctgacgatg  2580
cgtggagacc gaaaccttgc gctcgttcgc cagccaggac agaaatgcct cgacttcgct  2640
gctgccaag gttgccgggt gacgcacacc gtggaaacgg atgaaggcac gaacccagtg  2700
gacataagc tgttcggttc gtaagctgta atgcaagtag cgtatgcgct cacgcaactg  2760
gtccagaacc ttgaccgaac gcagcggtgg taacggcgca gtggcggttt tcatggcttg  2820
```

```
ttatgactgt ttttttgggg tacagtctat gcctcggtcg ggcatccaag cagcaagcgc    2880
gttacgccgt gggtcgatgt ttgatgttat ggagcagcaa cgatgttacg cagcagggca    2940
gtcgccctaa aacaaagtta aacatcatga gggaagcggt gatcgccgaa gtatcgactc    3000
aactatcaga ggtagttggc gtcatcgagc gccatctcga accgacgttg ctggccgtac    3060
atttgtacgg ctccgcagtg gatggcggcc tgaagccaca cagtgatatt gatttgctgg    3120
ttacggtgac cgtaaggctt gatgaaacaa cgccggcgagc tttgatcaac gacctttggg   3180
aaacttcggc ttcccctgga gagagcgaga ttctccgcgc tgtagaagtc accattgttg    3240
tgcacgacga catcattccg tggcgttatc cagctaagcg cgaactgcaa tttggagaat    3300
ggcagcgcaa tgacattctt gcaggtatct tcgagccagc cacgatcgac attgatctgg    3360
ctatcttgct gacaaaagca agagaacata gcgttgcctt ggtaggtcca gcggcggagg    3420
aactctttga tccggttcct gaacaggatc tatttgaggc gctaaatgaa accttaacgc    3480
tatggaactc gccgcccgac tgggctggcg atgagcgaaa tgtagtgctt acgttgtccc    3540
gcatttggta cagcgcagta accggcaaaa tcgcgccgaa ggatgtcgct gccgactggg    3600
caatggagcg cctgccggcc cagtatcagc ccgtcatact tgaagctaga caggcttatc    3660
ttggacaaga agaagatcgc ttggcctcgc gcgcagatca gttggaagaa tttgtccact    3720
acgtgaaagg cgagatcacc aaggtagtcg gcaaataatg tctaacaatt cgttcaagcc    3780
gacgccgctt cgcggcgcgg cttaactcaa gcgttagatg cactaagcac ataattgctc    3840
acagccaaac tatcaggtca agtctgcttt tattattttt aagcgtgcat aataagccct    3900
acacaaattg ggagatatat catgaaaggc tggctttttc ttgttatcgc aatagttggc    3960
gaagtaatcg caacatccgc attaaaatct agcgagggct ttactaagct gatccggtgg    4020
atgacctttt gaatgacctt taatagatta tattactaat taattgggga ccctagaggt    4080
cccctttttt attttaaaaa ttttttcaca aaacggttta caagcataaa gcttccgcgg    4140
tacccgggaa ttcgcccttt caagcttcag atcaattcgc gctaacttac attaattgcg    4200
ttgcgctcac tgcccgcttt ccagtcggga aacctgtcgt gccagctgca ttaatgaatc    4260
ggccaacgcg cggggagagg cggtttgcgt attgggcgcc agggtggttt tcttttcac    4320
cagtgagacg ggcaacagct gattgcccct taccgcctgg ccctgagaga gttgcagcaa    4380
gcggtccacg ctggtttgcc ccagcaggcg aaaatcctgt ttgatggtgg ttaacggcgg    4440
gatataacat gagctgtctt cggtatcgtc gtatcccact accgagatat ccgcaccaac    4500
gcgcagcccg gactcggtaa tggcgcgcat tgcgcccagc gccatctgat cgttggcaac    4560
cagcatcgca gtgggaacga tgccctcatt cagcatttgc atggtttgtt gaaaaccgga    4620
catggcactc cagtcgcctt cccgttccgc tatcggctga atttgattgc gagtgagata    4680
tttatgccag ccagccagac gcagacgcgc cgagacagaa cttaatgggc ccgctaacag    4740
cgcgatttgc tggtgaccca atgcgaccag atgctccacg cccagtcgcg taccgtcttc    4800
atgggagaaa ataatactgt tgatgggtgt ctggtcagag acatcaagaa ataacgccgg    4860
aacattagtg caggcagctt ccacagcaat ggcatcctgg tcatccagcg gatagttaat    4920
gatcagccca ctgacgcgtt gcgcgagaag attgtgcacc gccgctttac aggcttcgac    4980
gccgcttcgt tctaccatcg acaccaccac gctggcaccc agttgatcgg cgcgagattt    5040
aatcgccgcg acaatttgcg acggcgcgtg cagggccaga ctggaggtgg caacgccaat    5100
cagcaacgac tgtttgcccg ccagttgttg tgccacgcgg ttgggaatgt aattcagctc    5160
cgccatcgcc gcttccactt tttcccgcgt tttcgcagaa acgtggctgg cctggttcac    5220
```

```
cacgcgggaa acggtctgat aagagacacc ggcatactct gcgacatcgt ataacgttac    5280
tggtttcaca ttcaccaccc tgaattgact ctcttccggg cgctatcatg ccataccgcg    5340
aaaggttttg caccattcga tggtgtcaac gtaaatgcat gccgcttcgc cttcgcgcaa    5400
gcttagaagg gcgaattccg gacatatgga tcttggggga aattaagacc aaactcgatg    5460
acctccaaaa agatgtaact tctcttaaga tcgatatggc aacggtgaaa accgagttat    5520
ctgcggtcag gatggagata ggtacagtca aggatgatgt taaagatgtc aaagggcggg    5580
ctaatgctca aatttgggcg ttgattcttg ccgtcatcgg agccataatt accaccttgg    5640
tgcgttttgg catttcctt aatccctaac aaaaagcga ccaggctttt ctttcaattg    5700
cccgatcgcc tttgatattt tcccaaagga taaaagctag tccattcaga atcgagcctt    5760
aaagtactcc catattggct agccccagaa ttactccagc gccgaggatg tggccaaagc    5820
tagcggtgcc cagcacagcc cctaaaccaa agccgccaaa gaagttagag gaaggcatgg    5880
gggtgcccac attttgttgt tgatggtca atttaccaaa ggcgatcgcc aaaatgttgc    5940
aagcaatcat caccccagca actttagggc tccaggacag ggtggcggga acggcggtgg    6000
ccaacaaaaa gctatgcatt gagattctcc agaataaaga cggttttaa agggatagcc    6060 ccacgctaat gggggtcttt aaaaatctca tcttacgggg acgctctgcc cctgggaaac    6120
caccgttgca atacttaaca aattttcgtt tttagcttgg caaatgtctt tggcaaaatt    6180
ggttgatctg gcttaaatcg tcagttattt gccctggaat agtctgggga cgggcaattc    6240
tgatcagatt taccccaac gcttccgcca ctttttgctt aaccaattct cccccctggg    6300
caccggaggc tttagttacc acccccttgaa tttgccattg ttgccacagg gcttttcca    6360 atggttcggc tacggggggg cgcaaagcaa tgatacggtc ggaagtaaac ccagcggcga    6420
tcgcctgggc tagggcttgg ggatagggca gaatacggga aaatagggcc cagcttggcg    6480
taatcatggt catagctgtt tcctgtgtga aattgttatc cgctcacaat tccacacaac    6540
atacgagccg gaagcataaa gtgtaaagcc tggggtgcct aatgagtgag ctaactcaca    6600
ttaattgcgt tgcgctcact gcccgctttc cagtcgggaa acctgtcgtg ccagctgcat    6660
taatgaatcg gccaacgcgc ggggagaggc ggtttgcgta ttgggcgctc ttccgcttcc    6720
tcgctcactg actcgctgcg ctcggtcgtt cggctgcggc gagcggtatc agctcactca    6780
aaggcggtaa tacggttatc cacagaatca ggggataacg caggaaagaa catgtgagca    6840
aaaggccagc aaaaggccag gaaccgtaaa aaggccgcgt tgctggcgtt tttccatagg    6900
ctccgccccc ctgacgagca tcacaaaaat cgacgctcaa gtcagaggtg gcgaaacccg    6960
acaggactat aaagatacca ggcgtttccc cctggaagct ccctcgtgcg ctctcctgtt    7020
ccgaccctgc cgcttaccgg atacctgtcc gcctttctcc cttcgggaag cgtggcgctt    7080
tctcatagct cacgctgtag gtatctcagt tcggtgtagg tcgttcgctc caagctgggc    7140
tgtgtgcacg aaccccccgt tcagcccgac cgctgcgcct tatccggtaa ctatcgtctt    7200
gagtccaacc cggtaagaca cgacttatcg ccactggcag cagccactgg taacaggatt    7260
agcagagcga ggtatgtagg cggtgctaca gagttcttga agtggtggcc taactacggc    7320
tacactagaa ggacagtatt tggtatctgc gctctgctga agccagttac cttcggaaaa    7380
agagttggta gctcttgatc cggcaaacaa accaccgctg gtagcggtgg ttttttttgtt    7440 tgcaagcagc agattacgcg cagaaaaaaa ggatctcaag aagatccttt gatcttttct    7500
acggggtctg acgctcagtg gaacgaaaac tcacgttaag ggattttggt catgagatta    7560
tcaaaaagga tcttcaccta gatccttta aattaaaaat gaagttttaa atcaatctaa    7620
```

```
                                        -continued
agtatatatg agtaaacttg gtctga                                        7646

<210> SEQ ID NO 15
<211> LENGTH: 7677
<212> TYPE: DNA
<213> ORGANISM: Artificial sequence
<220> FEATURE:
<223> OTHER INFORMATION: pYC expression construct with the codon-
      optimized Clostridium thermocellum acyl-ACP thioesterase gene

<400> SEQUENCE: 15
cagttaccaa tgcttaatca gtgaggcacc tatctcagcg atctgtctat ttcgttcatc    60
catagttgcc tgactccccg tcgtgtagat aactacgata cgggagggct taccatctgg   120
ccccagtgct gcaatgatac cgcgagaccc acgctcaccg ctccagatt tatcagcaat    180
aaaccagcca gccggaaggg ccgagcgcag aagtggtcct gcaactttat ccgcctccat   240
ccagtctatt aattgttgcc gggaagctag agtaagtagt tcgccagtta atagtttgcg   300
caactgttgg gaagggcgat cggtgcgggc ctcttcgcta ttacgccagc tggcgaaagg   360
gggatgtgct gcaaggcgat taagttgggt aacgccaggg ttttcccagt cacgacgttg   420
taaaacgacg gccagtgaat tgggcccgac tgcctttggt ggtattaccg atgagtggca   480
cgttattttc accgctctgg ccgtgttgag catggtgctg gcaacgtgg tggctttagc    540
ccaaaccagc atgaaacgga tgttggccta ctcttccatc ggtcaagcag gctttgtgat   600
gattggccta gtggccggca gtgaagatgg ttacgccagc atggttttct acatgctcat   660
ctatctgttt atgaacctgg gggcgtttag ttgcattatt ctcttcaccc tccgcactgg   720
cagtgaccaa attagtgatt acgctggtct gtaccacaaa gaccccttgt taaccttggg   780
cttgagcatt tgtttattat ccttgggggg cattcctcct ctggcgggct ttttcggcaa   840
aatttacatc ttctgggccg gttggcaatc gggattgtat ggcctagtcc tacttggtct   900
ggttaccagt gtagtttcca tctactacta catccgggtg gtgaaaatga tggtggtgaa   960
ggagccccag gaaatgtccg aagtaatcaa aaattacccg gccatcaaat ggaatttacc  1020
cggcatgcgt cccctacagg tgggcattgt cgctactttg gttgctacct cgctggcagg  1080
tattctggct aatcccctct ttaacctcgc caccgattcc gtggtcagca ccaagatgtt  1140
gcagacagcc ctccagcaaa caggagaaac tccggcgatc gccatttccc atgatttacc  1200
ctaggggtat caggaaatat tgctttgcag gcaaaagcca atgagtgtaa ctatagaaac  1260
cgatttaaag gagatccact agtcctgagg ctgaaatgag ctgttgacaa ttaatcatcc  1320
ggctcgtata atgtgtggaa ttgtgagcgg ataacaattt cacactaagg aggaaaaaaa  1380
catgcaaaaa aagcggttca gcaagaagta cgaggtccac tactacgaga tcaacagcat  1440
gcaggaagcc accttgctgt ctctcctcaa ctacatggag gactgcgcca tcagccattc  1500
caccagtgcc ggctatggcg tgaatgaatt gttggccgcg gacgcggggt gggtgttgta  1560
ccggtggctg atcaagattg accgcttgcc caagctcgga gaaaccatca ccgtgcaaac  1620
ctgggcctcc tcctttgaac gcttctatgg caaccgagag ttcatcgtgc tggacgggcg  1680
cgacaacccc attgtgaagg cgagcagcgt ctggatctac ttcaacatca gaagcgcaa   1740
gcccatgcgg atccccctag agatgggcga cgcctacggc attgatgaga cccgagccct  1800
ggaggagccg ttcacggatt tgacttcga cttcagcccc aaggtgatcg aggagttcac  1860
cgtcaagcgc agtgacattg acaccaactc ccacgtgaac aacaagaaat acgtcgactg  1920
gatcatggag acggtacccc aacaaatcta tgacaattac aaggtcacgt ccctgcagat  1980
catctacaag aaggagagta gcctcggcag cgggattaaa gccgggtgcg tcatcgacga  2040
```

```
acagaatacg gacaatccgc gcctgctcca caagatctgg gataaaaaca cgggcctcga    2100
gctagtgtcc gccgagacca tttggcagaa aattcagtcc taatctagat atctgcaggc    2160 ctaagctttta tgcttgtaaa ccgttttgtg aaaaaatttt taaaataaaa aaggggacct    2220
ctagggtccc caattaatta gtaatataat ctattaaagg tcattcaaaa ggtcatccac    2280
cggatcaatt cccctgctcg cgcaggctgg gtgccaggcc cgatccttgg agcccttgcc    2340
ctcccgcacg atgatcgtgc cgtgatcgaa atccagatcc ttgacccgca gttgcaaacc    2400
ctcactgatc cgcatgcccg ttccatacag aagctgggcg aacaaacgat gctcgccttc    2460
cagaaaaccg aggatgcgaa ccacttcatc cggggtcagc accaccggca agcgccgcga    2520
cggccgaggt cttccgatct cctgaagcca gggcagatcc gtgcacagca ccttgccgta    2580
gaagaacagc aaggccgcca atgcctgacg atgcgtggag accgaaacct tgcgctcgtt    2640
cgccagccag gacagaaatg cctcgacttc gctgctgccc aaggttgccg ggtgacgcac    2700
accgtggaaa cggatgaagg cacgaaccca gtggacataa gcctgttcgg ttcgtaagct    2760
gtaatgcaag tagcgtatgc gctcacgcaa ctggtccaga accttgaccg aacgcagcgg    2820
tggtaacggc gcagtggcgg ttttcatggc ttgttatgac tgttttttttg gggtacagtc    2880 tatgcctcgg tcgggcatcc aagcagcaag cgcgttacgc cgtgggtcga tgtttgatgt    2940
tatggagcag caacgatgtt acgcagcagg gcagtcgccc taaaacaaag ttaaacatca    3000
tgagggaagc ggtgatcgcc gaagtatcga ctcaactatc agaggtagtt ggcgtcatcg    3060
agcgccatct cgaaccgacg ttgctggccg tacatttgta cggctccgca gtggatggcg    3120
gcctgaagcc acacagtgat attgatttgc tggttacggt gaccgtaagg cttgatgaaa    3180
caacgcggcg agctttgatc aacgaccttt tggaaacttc ggcttcccct ggagagagcg    3240
agattctccg cgctgtagaa gtcaccattg ttgtgcacga cgacatcatt ccgtggcgtt    3300
atccagctaa gcgcgaactg caatttggag aatggcagcg caatgacatt cttgcaggta    3360
tcttcgagcc agccacgatc gacattgatc tggctatctt gctgacaaaa gcaagagaac    3420
atagcgttgc cttggtaggt ccagcggcgg aggaactctt tgatccggtt cctgaacagg    3480
atctatttga ggcgctaaat gaaaccttaa cgctatggaa ctcgccgccc gactgggctg    3540
gcgatgagcg aaatgtagtg cttacgttgt cccgcatttg gtacagcgca gtaaccggca    3600
aaatcgcgcc gaaggatgtc gctgccgact gggcaatgga gcgcctgccg gcccagtatc    3660
agcccgtcat acttgaagct agacaggctt atcttggaca agaagaagat cgcttggcct    3720
cgcgcgcaga tcagttggaa gaatttgtcc actacgtgaa aggcgagatc accaaggtag    3780
tcggcaaata atgtctaaca attcgttcaa gccgacgccg cttcgcggcg cggcttaact    3840
caagcgttag atgcactaag cacataattg ctcacagcca aactatcagg tcaagtctgc    3900
ttttattatt tttaagcgtg cataataagc cctacacaaa ttgggagata tatcatgaaa    3960
ggctggcttt ttcttgttat cgcaatagtt ggcgaagtaa tcgcaacatc cgcattaaaa    4020
tctagcgagg gctttactaa gctgatccgg tggatgacct tttgaatgac ctttaataga    4080
ttatattact aattaattgg ggaccctaga ggtccccttt tttattttaa aattttttc    4140 acaaaacggt ttacaagcat aaagcttccg cggtacccgg gaattcgccc tttcaagctt    4200
cagatcaatt cgcgctaact tacattaatt gcgttgcgct cactgcccgc tttccagtcg    4260
ggaaacctgt cgtgccagct gcattaatga atcggccaac gcgcggggag aggcggtttg    4320
cgtattgggc gccagggtgg tttttctttt caccagtgag acgggcaaca gctgattgcc    4380
cttcaccgcc tggccctgag agagttgcag caagcggtcc acgctggttt gccccagcag    4440
```

```
gcgaaaatcc tgtttgatgg tggttaacgg cgggatataa catgagctgt cttcggtatc    4500
gtcgtatccc actaccgaga tatccgcacc aacgcgcagc ccggactcgg taatggcgcg    4560
cattgcgccc agcgccatct gatcgttggc aaccagcatc gcagtgggaa cgatgccctc    4620
attcagcatt tgcatggttt gttgaaaacc ggacatggca ctccagtcgc cttcccgttc    4680
cgctatcggc tgaatttgat tgcgagtgag atatttatgc cagccagcca gacgcagacg    4740
cgccgagaca gaacttaatg ggcccgctaa cagcgcgatt tgctggtgac ccaatgcgac    4800
cagatgctcc acgcccagtc gcgtaccgtc ttcatgggag aaaataatac tgttgatggg    4860
tgtctggtca gagacatcaa gaaataacgc cggaacatta gtgcaggcag cttccacagc    4920
aatggcatcc tggtcatcca gcggatagtt aatgatcagc ccactgacgc gttgcgcgag    4980
aagattgtgc accgccgctt tacaggcttc gacgccgctt cgttctacca tcgacaccac    5040
cacgctggca cccagttgat cggcgcgaga tttaatcgcc gcgacaattt gcgacggcgc    5100
gtgcagggcc agactggagg tggcaacgcc aatcagcaac gactgtttgc ccgccagttg    5160
ttgtgccacg cggttgggaa tgtaattcag ctccgccatc gccgcttcca cttttttcccg   5220 cgttttcgca gaaacgtggc tggcctggtt caccacgcgg gaaacggtct gataagagac    5280
accggcatac tctgcgacat cgtataacgt tactggtttc acattcacca ccctgaattg    5340
actctcttcc gggcgctatc atgccatacc gcgaaaggtt ttgcaccatt cgatggtgtc    5400
aacgtaaatg catgccgctt cgccttcgcg caagcttaga agggcgaatt ccggacatat    5460
ggatcttggg ggaaattaag accaaactcg atgacctcca aaaagatgta acttctctta    5520
agatcgatat ggcaacggtg aaaaccgagt tatctgcggt caggatggag ataggtacag    5580
tcaaggatga tgttaaagat gtcaaagggc gggctaatgc tcaaatttgg gcgttgattc    5640
ttgccgtcat cggagccata attaccacct tggtgcgttt tggcattttc cctaatccct    5700
aacaaaaaag cgaccaggct tttctttcaa ttgcccgatc gcctttgata ttttcccaaa    5760
ggataaaagc tagtccattc agaatcgagc cttaaagtac tcccatattg gctagcccca    5820
gaattactcc agcgccgagg atgtggccaa agctagcggt gcccagcaca gcccctaaac    5880
caaagccgcc aaagaagtta gaggaaggca tgggggtgcc cacattttgt tgtttgatgg    5940
tcaatttacc aaaggcgatc gccaaaaatgt tgcaagcaat catcacccca gcaactttag    6000
ggctccagga cagggtggcg ggaacggcgg tggccaacaa aaagctatgc attgagattc    6060
tccagaataa agacggtttt taagggata gccccacgct aatggggctc tttaaaaatc    6120
tcatcttacg gggacgctct gcccctggga aaccaccgtt gcaatactta acaaattttc    6180
gtttttagct tggcaaatgt ctttggcaaa attggttgat ctggcttaaa tcgtcagtta    6240
tttgccctgg aatagtctgg ggacgggcaa ttctgatcag atttaccccc aacgcttccg    6300 ccacttttttg cttaaccaat tctccccccct gggcaccgga ggctttagtt accacccctt    6360
gaatttgcca ttgttgccac agggcttttt ccaatggttc ggctacgggg gggcgcaaag    6420
caatgatacg gtcggaagta aacccagcgg cgatcgcctg ggctagggct tgggatagg    6480 gcagaatacg ggcaaatagg gcccagcttg gcgtaatcat ggtcatagct gtttcctgtg    6540
tgaaattgtt atccgctcac aattccacac aacatacgag ccggaagcat aaagtgtaaa    6600
gcctggggtg cctaatgagt gagctaactc acattaattg cgttgcgctc actgcccgct    6660
ttccagtcgg gaaacctgtc gtgccagctg cattaatgaa tcggccaacg cgcgggggaga   6720 ggcggttttgc gtattgggcg ctcttccgct tcctcgctca ctgactcgct gcgctcggtc   6780
gttcggctgc ggcgagcggt atcagctcac tcaaaggcgg taatacggtt atccacagaa   6840
```

-continued

```
tcaggggata acgcaggaaa gaacatgtga gcaaaaggcc agcaaaaggc caggaaccgt    6900
aaaaaggccg cgttgctggc gttttccat aggctccgcc ccctgacga gcatcacaaa      6960 aatcgacgct caagtcagag gtggcgaaac ccgacaggac tataaagata ccaggcgttt    7020 cccctggaa gctccctcgt gcgctctcct gttccgaccc tgccgcttac cggatacctg     7080 tccgccttc tcccttcggg aagcgtggcg ctttctcata gctcacgctg taggtatctc     7140
agttcggtgt aggtcgttcg ctccaagctg ggctgtgtgc acgaaccccc cgttcagccc    7200
gaccgctgcg ccttatccgg taactatcgt cttgagtcca acccgtaag acacgactta     7260 tcgccactgg cagcagccac tggtaacagg attagcagag cgaggtatgt aggcggtgct    7320
acagagttct tgaagtggtg cctaactac ggctacacta aaggacagt atttggtatc      7380 tgcgctctgc tgaagccagt taccttcgga aaaagagttg gtagctcttg atccggcaaa   7440
caaaccaccg ctggtagcgg tggttttttt gtttgcaagc agcagattac gcgcagaaaa   7500
aaaggatctc aagaagatcc tttgatcttt tctacgggt ctgacgctca gtggaacgaa     7560
aactcacgtt aagggatttt ggtcatgaga ttatcaaaaa ggatcttcac ctagatcctt    7620
ttaaattaaa aatgaagttt taaatcaatc taaagtatat atgagtaaac ttggtct       7677
```

<210> SEQ ID NO 16
<211> LENGTH: 259
<212> TYPE: PRT
<213> ORGANISM: Desulfovibrio desulfuricans
<220> FEATURE:
<223> OTHER INFORMATION: subsp. desulfuricans str. G20

<400> SEQUENCE: 16

```
Met Arg Cys Ile Gln Arg Asp His Met Ile Pro Phe Ala Gly His Thr
1               5                   10                  15

Gly Thr Glu Thr Phe Pro Val Arg Thr Tyr Asp Ala Asp Ser Thr Gly
            20                  25                  30

Arg Ala Gly Ile Arg Ala Ile Ala Asp Tyr Phe Gln Glu Ala Ala Ser
        35                  40                  45

Gly His Ala Arg Thr Leu Gly Phe Pro Ala Glu Arg Leu Arg Thr Glu
    50                  55                  60

Gln Leu Ala Trp Val Leu Ala Arg Leu Gln Ile Thr Val Asn Arg Phe
65                  70                  75                  80

Pro Pro Ala Gly Glu Thr Val Thr Ala Val Thr Trp Pro Ala His
                85                  90                  95

Glu Arg His Met Ala Tyr Arg Cys Tyr Glu Leu Tyr Thr Gln Asp Gly
            100                 105                 110

Glu Leu Leu Ala Ala Gly Thr Ser Ala Trp Val Thr Ile His Leu Ala
        115                 120                 125

Asp Arg Ser Met Val Pro Leu Pro Asp Phe Ile Arg Asp Gly Tyr Pro
    130                 135                 140

Gln Asp Asn Pro Pro Cys Arg Pro Phe Glu Thr Arg Thr Leu Pro Arg
145                 150                 155                 160

Leu Arg Glu Glu Ala Ala Gly Val Arg Ile Arg Thr Arg Arg Ala Asp
                165                 170                 175

Leu Asp Ile Asn Gly His Val Asn Asn Gly His Tyr Leu Gln Trp Leu
            180                 185                 190

Leu Glu Cys Met Pro Cys Asp Arg Gln Asn Glu Leu Arg Ala Val Asp
        195                 200                 205

Ile Ser Phe Arg Ala Glu Cys Phe Ala Asp Thr Glu Ile Val Ser Ala
    210                 215                 220
```

Arg Gly Ala Leu Thr Gly Glu His Thr Val Leu His Cys Ile Arg Thr
225                 230                 235                 240

Ala Asp Asp Ala Lys Glu Leu Cys Arg Ala Arg Ser Arg Trp Ala Ala
                245                 250                 255

Pro Leu Gly

<210> SEQ ID NO 17
<211> LENGTH: 243
<212> TYPE: PRT
<213> ORGANISM: Elusimicrobium minutum (strain Pei191)

<400> SEQUENCE: 17

Met Thr Glu Leu Glu Phe Lys Pro Arg Tyr Tyr Glu Ala Ala Leu Asp
1               5                   10                  15

Asp Ser Ile Pro Val His Met Leu Cys Asn Tyr Leu Gln Glu Gly Ala
                20                  25                  30

Gly Gln Asp Ala Asn Asn Leu Ser Phe Gly Arg Glu Gln Ile Gly Glu
            35                  40                  45

His Gly Val Ala Trp Val Leu Ser Arg Met Gln Ile Glu Leu Ile Asn
50                  55                  60

Lys Ala Val Leu Gly Lys Lys Leu Lys Val Lys Thr Trp Pro Ser Phe
65                  70                  75                  80

Ser Glu Lys Ile Ile Ser Arg Arg Glu Tyr Ile Ile Thr Asp Glu Asp
                85                  90                  95

Gly Lys Ile Ile Leu Lys Cys Ser Ser Trp Trp Leu Ile Leu Asn Leu
            100                 105                 110

Asn Thr Arg Lys Ile Thr Arg Ile Pro Gln His Met Leu Asp Leu Asn
        115                 120                 125

Thr Glu Lys Pro Asp Phe Met Val Glu Glu Gly Asn Phe Lys Leu Lys
130                 135                 140

Thr Pro Gln Asp Ala Lys Pro Val Phe Ser Lys Asp Phe Leu Val Arg
145                 150                 155                 160

Leu Glu Asp Ile Asp Cys Asn Gly His Val Asn Asn Thr His Tyr Ile
                165                 170                 175

Ala Trp Ala Ile Glu Thr Leu Pro Ala Glu Val Val Lys Asn Lys Thr
            180                 185                 190

Ile Lys Ser Leu Arg Ile Asn Phe Lys Ser Glu Cys Ile Asp Gly Asn
        195                 200                 205

Lys Ile Lys Ser Phe Val Tyr Asp Asn Gly Asn Ser Glu Tyr Ile His
    210                 215                 220

Glu Leu Val Arg Glu Asp Asp Gly Lys Glu Val Phe Arg Leu Val Ser
225                 230                 235                 240

Asn Trp Gln

<210> SEQ ID NO 18
<211> LENGTH: 220
<212> TYPE: PRT
<213> ORGANISM: Carboxydothermus hydrogenoformans Z-2901

<400> SEQUENCE: 18

Met Asn Ser Asn Ile Phe Glu Leu Glu Tyr Arg Ile Pro Tyr Tyr Asp
1               5                   10                  15

Val Asp Tyr Gln Lys Arg Thr Leu Ile Thr Ser Leu Ile Asn Tyr Phe
                20                  25                  30

Asn Asp Ile Ala Phe Val Gln Ser Glu Asn Leu Gly Gly Ile Ala Tyr
            35                  40                  45

```
Leu Thr Gln Asn Asn Leu Gly Trp Val Leu Met Asn Trp Asp Ile Lys
     50                  55                  60

Val Asp Arg Tyr Pro Arg Phe Asn Glu Arg Val Leu Val Arg Thr Ala
 65                  70                  75                  80

Pro His Ser Phe Asn Lys Phe Ala Tyr Arg Trp Phe Glu Ile Tyr
                 85                  90                  95

Asp Lys Asn Gly Ile Lys Ile Ala Lys Ala Asn Ser Arg Trp Leu Leu
                100                 105                 110

Ile Asn Thr Glu Lys Arg Arg Pro Val Lys Ile Asn Asp Tyr Leu Tyr
            115                 120                 125

Gly Ile Tyr Gly Val Ser Tyr Glu Asn Asn Asn Ile Leu Pro Ile Glu
130                 135                 140

Glu Pro Gln Lys Leu Leu Ser Ile Asp Ile Glu Lys Gln Phe Glu Val
145                 150                 155                 160

Arg Tyr Ser Asp Leu Asp Ser Asn Gly His Val Asn Asn Val Lys Tyr
                165                 170                 175

Val Val Trp Ala Leu Asp Thr Val Pro Leu Glu Ile Ile Ser Asn Tyr
            180                 185                 190

Ser Leu Gln Arg Leu Lys Val Lys Tyr Glu Lys Glu Val Thr Tyr Gly
        195                 200                 205

Lys Thr Val Arg Val Leu Thr Gly Ile Leu Ser Glu
210                 215                 220

<210> SEQ ID NO 19
<211> LENGTH: 252
<212> TYPE: PRT
<213> ORGANISM: Moorella thermoacetica ATCC 39073

<400> SEQUENCE: 19

Met Pro Thr Ser Thr Tyr Gln Arg Asp Tyr Glu Val Arg Tyr Tyr Glu
1               5                   10                  15

Thr Asn Phe Leu Leu Glu Ala Ser Pro Val Thr Ile Leu Gly Tyr Leu
            20                  25                  30

Glu Glu Thr Ala Thr Leu His Ser Glu Thr Ala Gly Ile Gly Ile Asn
        35                  40                  45

Lys Leu Lys Ala Ala Gly Arg Gly Trp Val Val Tyr Arg Tyr His Leu
 50                  55                  60

Gln Met Glu Arg Tyr Pro Arg Trp Arg Glu His Ile Thr Ile Thr Thr
 65                  70                  75                  80

Trp Val Glu Asn Phe Gln Arg Cys Phe Ala His Arg Asp Phe Tyr Ile
                 85                  90                  95

His Asp Ala Gly Gly Asn Leu Ile Gly Arg Ala Ala Ser Val Trp Val
                100                 105                 110

Phe Leu Asp Ile His Lys Lys Lys Pro Leu Arg Ile Pro Pro Gln Val
            115                 120                 125

Thr Gly Ala Tyr Gly Leu Tyr Pro Glu Val Ala Val Pro Gly Ala Phe
130                 135                 140

Thr Asp Leu Pro Ser Leu Glu Lys Pro Ala Thr Ala Gly Glu Phe Thr
145                 150                 155                 160

Val Arg Met Ala Asp Leu Asp Thr Asn His His Ala Asn Asn Lys Arg
                165                 170                 175

Tyr Ile Gly Trp Ile Leu Glu Gly Val Pro Leu Glu Val His Arg Thr
            180                 185                 190

Ala Phe Pro Ala Thr Ile Glu Val Leu Tyr Lys Lys Asp Ala Arg Tyr
        195                 200                 205
```

Gly Glu His Ile His Cys Glu Cys Gln Glu Ile Pro Ala Val Glu Gly
            210                 215                 220

Asp Arg Cys Tyr Leu His Arg Leu Ser Cys Pro Glu Arg Asp Leu Glu
225                 230                 235                 240

Leu Thr Leu Ala Arg Thr Thr Trp Arg Lys Arg Arg
            245                 250

<210> SEQ ID NO 20
<211> LENGTH: 247
<212> TYPE: PRT
<213> ORGANISM: Geobacter metallireducens GS-15

<400> SEQUENCE: 20

Met Lys Thr Glu Asn Ser Ile Phe Glu Thr Ser Phe Thr Ile Arg Ser
1               5                   10                  15

Phe Asp Val Asp Pro His Gly Phe Val Ser Pro Val Thr Leu Leu Gly
            20                  25                  30

Tyr Leu Gln Glu Ala Ala Ser Glu His Met Thr Leu Leu Gly Gly Thr
        35                  40                  45

Val Arg Ser Leu Met Ala Glu Gly Leu Thr Trp Val Leu Ser Arg Val
50                  55                  60

His Leu Ser Ile Glu Arg Tyr Pro Arg Val Arg Asn Glu Met Thr Val
65                  70                  75                  80

Arg Thr Trp Pro Ser Leu Arg Glu Gly Arg Phe Thr Cys Arg Glu Phe
                85                  90                  95

Glu Leu Leu Asp Arg Thr Gly Ala Val Met Ala Arg Ala Thr Thr Ser
            100                 105                 110

Trp Ala Val Ile Asp Phe Lys Thr Arg Arg Ala Val Arg Val Asp Arg
        115                 120                 125

His Pro Pro Tyr Pro Leu Thr Pro Arg Arg Ala Ile Asp Asp Asp Phe
130                 135                 140

Ala Leu Leu Pro Ala Leu Lys Gly Ser Gln Ala Glu Glu Arg Phe Arg
145                 150                 155                 160

Val Arg Arg Ser Asp Leu Asp Leu Asn His His Val Asn His Met Val
                165                 170                 175

Tyr Ala Gly Trp Ala Leu Asp Ala Val Pro Asp Glu Val Ala Glu Arg
            180                 185                 190

His Lys Leu Val Ser Leu Glu Ile Gly Tyr Arg Ala Glu Ala Leu Ala
        195                 200                 205

Gly Glu Glu Val Thr Val Cys Cys Ala Cys Ala Glu Asp Asp Asn Gly
210                 215                 220

Ile Leu Val Ile His Arg Ile Ala Ser Ala Asp Cys Arg Glu Leu Thr
225                 230                 235                 240

Arg Leu Arg Thr Arg Trp Arg
            245

<210> SEQ ID NO 21
<211> LENGTH: 248
<212> TYPE: PRT
<213> ORGANISM: Salinibacter ruber DSM 13855

<400> SEQUENCE: 21

Met Thr Ala Gly Ile Trp Thr Asp Glu Val Arg Val Arg Ser Tyr Asp
1               5                   10                  15

Val Thr Pro Gln Gly Thr Ala Ser Val Leu Thr Leu Ala Asp Tyr Phe
            20                  25                  30

```
Gln Glu Ala Ala Gly Arg His Ala Ala Glu Leu Gly Val Ser Met Thr
            35                  40                  45

Asp Leu Arg Ala Asp Gly Gln Ala Trp Val Leu Ala Phe Met His Met
 50                  55                  60

Gln Val Glu Arg Leu Pro His Gln Asn Glu Ser Leu Arg Ile Glu Thr
 65                  70                  75                  80

Trp Pro Ser Gly Leu Glu Ser Ala Ser Ala His Arg Glu Phe Val Phe
                 85                  90                  95

His Asp Glu Glu Gly Thr Val Leu Ala Gly Gly Thr Ser Arg Trp Phe
                100                 105                 110

Val Phe Asp Val Asp Arg Arg Pro Val Arg Pro Arg Val Leu
                115                 120                 125

Ala Asp Ile Glu Gly Pro Asp Arg Pro Gly Pro Ile Asp Gln Asp Leu
            130                 135                 140

Asp Ala Leu Ser Ala Pro Ala His Thr Asp Arg Glu Gln Thr Phe Thr
145                 150                 155                 160

Ala Arg Tyr His Asp Leu Asp Leu Asn Arg His Val Asn Asn Val Arg
                165                 170                 175

Tyr Leu Glu Trp Ala Leu Glu Thr Leu Pro Ala Val Leu Asp Glu
                180                 185                 190

Arg Arg Cys Leu Gly Phe Ala Val Gln Phe Glu Ala Glu Thr Arg Leu
            195                 200                 205

Gly Asp Pro Val Arg Ala Ser Ala Glu Gln Ile Glu Asp Gly Gly Thr
210                 215                 220

Leu Arg Val Arg His Arg Leu Ala His Ala Glu Ser Asp Gln Thr Leu
225                 230                 235                 240

Ala Leu Val Arg Thr Thr Trp Leu
                245

<210> SEQ ID NO 22
<211> LENGTH: 269
<212> TYPE: PRT
<213> ORGANISM: Microscilla marina  ATCC 23134

<400> SEQUENCE: 22

Met Cys Asp Leu Ile Ile Glu Asp Ala Lys Asn Ile Tyr Leu Trp Tyr
  1               5                  10                  15

Met Glu Lys Asn Gln Thr Thr Gln Leu Pro Lys Ile Trp Leu Asp Phe
             20                  25                  30

Glu Val Arg Ala Tyr Glu Val Asp Ile Tyr Asn Arg Val Ser Pro Val
            35                  40                  45

Thr Ile Ala Asn Tyr Leu Gln Glu Ala Ala Gly Gln His Ala Asp His
 50                  55                  60

Leu Gly Val Gly Val Thr Asp Leu Leu Lys His Arg Leu Thr Trp Val
 65                  70                  75                  80

Leu Thr Arg Ile Lys Ile Asp Met Gln Gln Tyr Pro Ser Arg Tyr Glu
                 85                  90                  95

Pro Val Arg Val Leu Thr Tyr Pro Ile Gly Tyr Asp Lys Tyr Phe Val
                100                 105                 110

Tyr Arg Asn Phe Gln Leu Tyr Asn Ala Gln Gly Lys Gln Ile Gly Gln
            115                 120                 125

Ala Thr Ser Thr Trp Ala Val Met Asp Ile Gln Ala Arg Lys Met Val
130                 135                 140

Gly Val Pro Gln Leu Ile Thr Ser Leu Pro Ile Pro Asp Asp Glu Asp
145                 150                 155                 160
```

```
Phe Ile Thr Arg Thr Lys Gly Lys Ile Ala Lys Val Asn Ala Pro Leu
                165                 170                 175

Ser Glu Thr Leu Phe Arg Val Arg Trp Asn Asp Leu Asp Thr Asn Gln
            180                 185                 190

His Thr Asn Asn Ala Tyr Tyr Leu Gln Trp Ala Ile Glu Ser Leu Pro
        195                 200                 205

Glu Glu Val Leu Lys Ser Arg Gln Leu Ala Ser Ile Asp Leu Leu Tyr
    210                 215                 220

Arg Leu Glu Thr Thr Trp Lys Glu Gly Val Val Ala Arg Thr Glu Gln
225                 230                 235                 240

Thr Ser Thr Gln Pro Leu Ser Phe Ile His Gln Leu Ile Arg Glu Ser
                245                 250                 255

Asp Gln Lys Glu Leu Ala Gln Ala Thr Thr Val Trp Val
            260                 265

<210> SEQ ID NO 23
<211> LENGTH: 251
<212> TYPE: PRT
<213> ORGANISM: Enterococcus faecalis TX0104

<400> SEQUENCE: 23

Met Glu Lys Gly Asp Tyr Phe Val Gly Lys Lys His Thr Ser Ser Tyr
1               5                   10                  15

Glu Val Ala Tyr Tyr Asp Gly Asp Phe Thr Gly Ala Met Lys Ile Pro
            20                  25                  30

Ala Leu Leu Ala Val Val Ile Lys Val Ser Glu Glu Gln Thr Glu Leu
        35                  40                  45

Leu Gly Arg Asn Ala Ala Tyr Val Ala Gln Phe Gly Leu Gly Trp Val
    50                  55                  60

Ile Thr Asn Tyr Glu Ile Glu Ile His Arg Leu Pro Lys Val Gly Glu
65                  70                  75                  80

Lys Val Ala Ile Thr Thr Gln Ala Met Ser Tyr Asn Lys Tyr Phe Cys
                85                  90                  95

Tyr Arg Asn Phe Trp Val His Asp Glu Glu Gly Asn Glu Cys Val Phe
            100                 105                 110

Val Lys Ser Thr Phe Val Leu Met Asp Gln Lys Asn Arg Lys Ile Ser
        115                 120                 125

Ser Val Leu Pro Glu Ile Ile Ala Pro Phe Asp Ser Glu Lys Ile Thr
    130                 135                 140

Lys Ile Tyr Arg His Glu Lys Ile Glu Lys Val Thr Glu Gly Asn Phe
145                 150                 155                 160

Leu Pro Tyr Arg Val Arg Phe Phe Asp Ile Asp Gly Asn Gln His Val
                165                 170                 175

Asn Asn Ala Ile Tyr Phe Asn Trp Leu Leu Asp Val Leu Gly Tyr Asp
            180                 185                 190

Phe Leu Thr Thr His Gln Pro Lys Lys Ile Leu Val Lys Phe Asp Lys
        195                 200                 205

Glu Val Glu Tyr Gly Gln Glu Val Ser His Tyr Glu Ile Val Glu
    210                 215                 220

Gln Glu Asn His Leu Lys Thr Arg His Glu Ile Arg Ile Asp Gly Gln
225                 230                 235                 240

Thr Tyr Cys Glu Ala Asn Ile Asp Trp Thr Asn
                245                 250

<210> SEQ ID NO 24
<211> LENGTH: 261
```

```
<212> TYPE: PRT
<213> ORGANISM: Lactobacillus plantarum JDM1

<400> SEQUENCE: 24

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

Val Thr Val Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Gln Thr Val Thr Ala His Ala Asn Ile
    210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 25
<211> LENGTH: 243
<212> TYPE: PRT
<213> ORGANISM: Leuconostoc mesenteroides
<220> FEATURE:
<223> OTHER INFORMATION: subsp. mesenteroides ATCC 8293

<400> SEQUENCE: 25

Met Lys Lys Tyr Glu Ile Lys Arg Arg Val Glu Tyr Tyr Glu Ala Asp
1               5                   10                  15

Thr Thr Gln Lys Leu Ser Leu Pro Met Ile Leu Asn Tyr Ala Val Leu
            20                  25                  30

Ala Ser Lys Cys Gln Ser Asp Glu Leu Gly Val Gly Gln Asp Phe His
        35                  40                  45

Leu Gly Arg Gly Leu Gly Trp Ile Ile Leu Gln Tyr Glu Val Ile Ile
    50                  55                  60

Lys Arg Arg Pro Lys Ile Gly Glu Ile Ile Arg Ile Gln Thr Phe Ala
65                  70                  75                  80
```

```
Thr Gln Tyr Asn Pro Phe Phe Val Arg Arg Pro Phe Val Phe Leu Asp
                85                  90                  95

Glu Asn Asp Asn Glu Ile Ile Arg Val Asp Ser Ile Trp Thr Met Ile
            100                 105                 110

Asp Met Thr Asn Arg Arg Met Ala Arg Leu Pro Gln Asp Ile Ile Asp
        115                 120                 125

Gln Tyr Asp Ala Lys Arg Val Lys Gln Ile Ser Arg Ile Pro Asn Pro
    130                 135                 140

Glu Lys Phe Ser Asp Asp Gln Tyr Thr Glu Arg Asp Tyr His Val
145                 150                 155                 160

Arg Tyr Leu Asp Ile Asp Gly Asn Lys His Val Asn Asn Ser Lys Tyr
                165                 170                 175

Phe Glu Trp Met Gln Asp Val Ile Ala Pro Glu Tyr Leu Leu Thr His
            180                 185                 190

Glu Ile Thr Tyr Ile Asn Leu Lys Phe Glu Asn Glu Ile Arg Leu Gly
        195                 200                 205

His Thr Ile Leu Ser Gln Val Val Gln Asn Asp Asn Lys Ser Lys His
    210                 215                 220

Arg Ile Met Met Glu Asn Val Ile Ser Ala Glu Ala Glu Phe Lys Trp
225                 230                 235                 240

Arg Lys Ile

<210> SEQ ID NO 26
<211> LENGTH: 260
<212> TYPE: PRT
<213> ORGANISM: Oenococcus oeni ATCC BAA-1163

<400> SEQUENCE: 26

Met Phe Ile Lys Phe Thr Ile Arg Arg Lys Thr Met Ser Glu Ile Tyr
1               5                   10                  15

Ser Glu Glu Leu Tyr Ile Glu Asp Phe Tyr Cys Asp Arg Thr Ala Lys
            20                  25                  30

Leu Ser Leu Pro Met Ile Thr Glu Leu Ala Ile Ser Val Ser Ser Lys
        35                  40                  45

Gln Thr Val Glu Met Gly Ile Gly Met Gln Arg Leu Val Glu Ala His
    50                  55                  60

His Gly Trp Ile Leu Leu Gln Tyr Asp Ile Lys Ile Asn Arg Arg Pro
65              70                  75                  80

Asn Leu Gly Glu Lys Ile Lys Ile Arg Thr Asp Pro Lys Arg His Asn
            85                  90                  95

Arg Phe Phe Ala Phe Arg Asp Phe Asp Phe Asp Gln Asp Gly Asn
        100                 105                 110

Thr Leu Ile His Ile Asp Ser Leu Trp Ala Met Ile Asp Leu Lys Arg
    115                 120                 125

Arg Arg Leu Val Ser Ile Asp Ser Glu Phe Val Asp Pro Leu Lys Gly
130                 135                 140

Asn Leu Val Asp Arg Leu Glu Arg Leu Glu Lys Pro Ala Asp Leu Asp
145                 150                 155                 160

Arg Ser Phe Ser Gly Ala Ser Ile Ser Val Glu Glu Ile Lys Ala Asn
                165                 170                 175

Tyr Phe Asp Ile Asp Thr Asn Gln His Val Asn Asn Ser Asn Tyr Leu
            180                 185                 190

Lys Phe Phe Leu Val Pro Val Ala Glu Asn Phe Leu Leu Arg His Glu
        195                 200                 205
```

-continued

```
Pro Lys Arg Ile Leu Ile Lys Tyr Val Lys Glu Ile Arg Leu Asn Gln
    210                 215                 220

Ser Val Val Ser Met Ala Gln Phe Ile Gly Pro Leu His Ser Val His
225                 230                 235                 240

Glu Ile Ser Asp Asn Ser Leu Ile Asn Ala Gln Ala Glu Ile Glu Trp
                245                 250                 255

Ser Glu Val Glu
            260

<210> SEQ ID NO 27
<211> LENGTH: 282
<212> TYPE: PRT
<213> ORGANISM: Mycobacterium smegmatis str. MC2 155

<400> SEQUENCE: 27

Met Thr Gly Thr Glu Lys Gly Ser Lys Asp Ser Ser Glu Asn Ser Leu
1               5                   10                  15

Val Ser Thr Gly Leu Ala Lys Thr Met Met Pro Val Pro Asp Pro His
            20                  25                  30

Pro Asp Val Phe Asp Thr Gly Trp Pro Leu Arg Val Ala Asp Ile Asp
        35                  40                  45

Arg Asn Gly Arg Leu Arg Phe Asp Ala Ser Thr Arg His Ile Gln Asp
    50                  55                  60

Ile Gly Gln Asp His Leu Arg Gln Leu Gly Phe Glu Asp Thr His Pro
65                  70                  75                  80

Ala Trp Ile Val Arg Arg Thr Met Ile Asp Met Ile Glu Pro Ile Glu
                85                  90                  95

Phe Pro Glu Leu Leu Arg Leu Arg Arg Trp Cys Ser Gly Thr Ser Asn
            100                 105                 110

Arg Trp Cys Glu Met Arg Val Arg Ile Asp Gly Arg Lys Gly Gly Leu
        115                 120                 125

Val Glu Ser Glu Ala Phe Trp Ile Asn Ile Asn Arg Glu Thr Gln Gly
    130                 135                 140

Pro Ser Arg Ile Ala Asp Asp Phe Leu Ala Gly Leu Arg Arg Thr Thr
145                 150                 155                 160

Asp Ile Asp Arg Leu Arg Trp Lys Pro Tyr Leu Lys Ala Gly Ser Arg
                165                 170                 175

Glu Asp Ala Leu Glu Ile Arg Glu Tyr Pro Val Arg Val Ala Asp Ile
            180                 185                 190

Asp Leu Phe Asp His Met Asn Asn Ala Val Tyr Trp Thr Val Val Glu
        195                 200                 205

Asp Tyr Leu Tyr Thr His Pro Glu Leu Leu Ala Gln Pro Leu Arg Val
    210                 215                 220

Thr Ile Glu His Asp Ala Pro Val Ala Leu Gly Asp Lys Leu Glu Ile
225                 230                 235                 240

Ile Ser His Thr His Pro Pro Gly Thr Thr Asp Lys Phe Gly Pro Glu
                245                 250                 255

Leu Thr Asp Arg Thr Val Thr Thr Leu Thr Tyr Ala Val Gly Glu Glu
            260                 265                 270

Thr Lys Ala Val Ala Cys Leu Phe Ser Leu
        275                 280

<210> SEQ ID NO 28
<211> LENGTH: 271
<212> TYPE: PRT
<213> ORGANISM: Mycobacterium vanbaalenii PYR-1
```

```
<400> SEQUENCE: 28

Met Ser Thr Thr Pro Gly Ala Thr Gly Leu Ala Lys Ala Met Met Pro
1               5                   10                  15

Val Pro Asp Pro His Pro Asp Val Phe Asp Ile Gln Trp Pro Leu Arg
            20                  25                  30

Val Ala Asp Val Asp Arg Glu Gly Arg Leu Lys Phe Asp Ala Ala Thr
        35                  40                  45

Arg His Ile Gln Asp Ile Gly Thr Asp Gln Leu Arg Glu Met Gly Tyr
    50                  55                  60

Glu Asp Thr His Pro Leu Trp Ile Val Arg Arg Thr Met Ile Asp Met
65                  70                  75                  80

Ile Glu Pro Val Val Phe Lys Asp Met Leu Arg Leu Arg Arg Trp Cys
                85                  90                  95

Ser Gly Thr Ser Asn Arg Trp Cys Glu Met Arg Val Arg Ile Glu Gly
            100                 105                 110

Arg Lys Gly Gly Leu Ile Glu Ser Glu Ala Phe Trp Ile Asn Ile Asn
        115                 120                 125

Arg Glu Thr Gln Gly Pro Ala Arg Ile Ser Asp Asp Phe Ile Glu Gly
    130                 135                 140

Leu Arg Arg Thr Thr Asp Glu Asn Arg Leu Arg Trp Lys Pro Tyr Leu
145                 150                 155                 160

Arg Ala Gly Ser Arg Glu Asp Ala Glu His Ile Arg Asp Tyr Pro Val
                165                 170                 175

Arg Val Ser Asp Ile Asp Ile Phe Asp His Met Asn Asn Ser Val Tyr
            180                 185                 190

Trp Ser Val Val Glu Asp Tyr Leu Tyr Ser Gln Pro Glu Leu Met Ser
        195                 200                 205

Ala Pro Val Arg Val Thr Ile Glu His Asp Leu Pro Val Ala Leu Gly
    210                 215                 220

Asp Lys Leu Glu Ile Ile Arg His Val His Pro Ala Gly Ser Thr Asp
225                 230                 235                 240

Lys Phe Gly Glu Glu Leu Ser Asp Arg Thr Val Thr Thr Leu Thr Tyr
                245                 250                 255

Ala Val Gly Asn Glu Thr Lys Ala Val Ala Ala Ile Phe Pro Leu
            260                 265                 270

<210> SEQ ID NO 29
<211> LENGTH: 256
<212> TYPE: PRT
<213> ORGANISM: Rhodococcus erythropolis SK121

<400> SEQUENCE: 29

Met Asn Arg Thr Lys Val Asp Asp His Val Ala Met Ala Glu Leu Pro
1               5                   10                  15

Thr Thr Gly Ser Ile Phe Gln Ala Ser Trp Pro Val Arg Thr Gly Asp
            20                  25                  30

Ile His Thr Asp Lys Gln Leu Arg Leu Asp Ala Ile Ala Arg Tyr Leu
        35                  40                  45

Gln Asp Ala Gly Phe Asp Asn Leu Val Asp Arg Gly Ala Met Asp Thr
    50                  55                  60

His Pro Leu Trp Met Val Arg Thr Val Ile Asp Val Leu Glu Pro
65                  70                  75                  80

Val Val Trp Pro Asp Arg Val His Leu Gln Arg Trp Cys Ser Gly Leu
                85                  90                  95

Ser Asn Lys Trp Cys Ser Met Arg Val Arg Ile Arg Ser Asp Gly Gly
```

```
            100                 105                 110
Gly Leu Ile Glu Thr Glu Ala Phe Trp Ile Asn Ile Asp Pro Lys Thr
            115                 120                 125

Gly Met Pro Ala Ser Ile Ser Glu Lys Phe Thr Ala Ala Leu Ala Ser
        130                 135                 140

Thr Ala Val Asp Gln His Leu His Trp Arg Arg Trp Ile Asp Pro Thr
145                 150                 155                 160

Pro Asp Thr Thr Pro Ser Ala Asp Thr Pro Phe Pro Leu Arg Ser Ser
                    165                 170                 175

Asp Phe Asp Pro Phe Asp His Val Asn Asn Ala Ile Tyr Trp Gln Pro
                180                 185                 190

Val Glu Asp Ala Leu Pro Asp Arg Leu Arg Ser Gly Pro Phe Arg Ala
            195                 200                 205

Ile Leu Glu Tyr Thr Gln Pro Ile Lys Arg Gly Glu Gln Val Ser Val
        210                 215                 220

Arg Thr Gly Thr Asn Thr Leu His Ile Asp Ala Gly Asp Glu Ala Arg
225                 230                 235                 240

Ala Ser Ala Arg Trp Phe Ala Leu Ser Pro Lys Ser Asn Asp Gln Gly
                    245                 250                 255

<210> SEQ ID NO 30
<211> LENGTH: 259
<212> TYPE: PRT
<213> ORGANISM: Rhodococcus opacus B4

<400> SEQUENCE: 30

Met Ala Leu Asp Arg Pro Leu Ala Ala Pro Pro Ser Arg Gly Arg Phe
1               5                   10                  15

Phe Glu Thr Ser Trp Pro Val Arg Thr Gly Asp Ile Asp Ala Ala Lys
            20                  25                  30

Arg Leu Arg Leu Asp Gly Ile Ala Arg Tyr Leu Gln Asp Ala Gly Leu
        35                  40                  45

Asp Asn Leu Asp Ala Val Asp Ala Ala Asp Ser His Pro Leu Trp Ile
    50                  55                  60

Val Arg Arg Thr Val Ile Asp Val Leu Arg Pro Ala Val Trp Pro Glu
65                  70                  75                  80

Arg Val His Leu Arg Arg Trp Cys Ser Ala Leu Ser Thr Arg Trp Thr
                85                  90                  95

Asn Met Arg Val Gln Ile Arg Gly Glu Ala Gly Ala Leu Ile Glu Thr
            100                 105                 110

Glu Gly Phe Trp Ile His Ile Ser Gly Glu Thr Gly Met Pro Thr Arg
        115                 120                 125

Ile Asp Asp Gly Phe Ile Glu Arg Leu Gly Glu Ser Ala Glu Glu His
    130                 135                 140

Arg Leu Lys Trp Lys Arg Trp Leu Val Glu Asn Ala Pro Ala Ala Asp
145                 150                 155                 160

Glu Asp Gly Ile Glu Asp Ser Glu Phe Val Leu Arg Arg Thr Asp Ile
                165                 170                 175

Asp Pro Phe Asp His Val Asn Asn Ala Val Tyr Trp Gln Ala Val Glu
            180                 185                 190

Glu Leu Leu Ala Asp His Glu His Pro Gly Gly Gly Arg Leu Val Asp
        195                 200                 205

Asn Pro His Arg Ala Val Leu Glu Tyr Leu Ala Pro Ile Val Ser Thr
    210                 215                 220
```

```
Asp Lys Ile Val Leu Arg Ser Arg Arg Asp Asp Thr Ser Leu Thr Val
225                 230                 235                 240

Trp Phe Leu Val Asp Asp Ala Leu Arg Ala Val Ala His Val Gly Pro
                245                 250                 255

Leu Thr Ala
```

PHOTOSYNTHETIC MICROORGANISMS COMPRISING EXOGENOUS PROKARYOTIC ACYL-ACP THIOESTERASES AND METHODS FOR PRODUCING FATTY ACIDS

CROSS-REFERENCE TO RELATED APPLICATIONS

This application claims benefit of priority to U.S. provisional patent application 61/426,555 of the same title filed Dec. 23, 2010, which is hereby incorporated by reference in its entirety.

REFERENCE TO A SEQUENCE LISTING

This application contains references to amino acid sequences and/or nucleic acid sequences which have been submitted concurrently herewith as the sequence listing text file entitled "2010EM384 (PM0001) sequences.TXT", file size 62.2 KiloBytes (KB), created on Dec. 12, 2011. The aforementioned sequence listing is hereby incorporated by reference in its entirety pursuant to 37 C.F.R. §1.52(e)(5).

FIELD OF THE INVENTION

The invention relates to compositions and methods for producing free fatty acids and/or fatty acid derivatives in microorganisms, including photosynthetic microorganisms such as cyanobacteria and microalgae.

BACKGROUND

1. Biofuels

Biofuels represent renewable energy sources from living organisms, such as higher plants, fungi, or bacteria. Photosynthetic life forms capture light energy and subsequently convert it into the free energy of organic compounds based on fixed CO2, using water as the ultimate electron donor. Currently, two major technologies are employed for generating biofuels using phototrophic organisms: first, plant-based biofuel production via fermentation of the plant's sugar content to ethanol and, second, to a much lesser extent, algae-derived biodiesel production through lipid extraction of biomass from large-scale cultures (Angermayr et al., 2009, Curr Opin Biotechnol, 20(3): 257-263).

2. Fatty Acids

Fatty acids are carboxylic acids with hydrocarbon chains of 4 to 36 carbons. In some fatty acids, this chain is fully saturated (meaning contains no double bonds) and unbranched; others contain one (monounsaturated) or more double bonds (polyunsaturated). A few contain three-carbon rings or hydroxyl groups. A simplified nomenclature for these compounds specifies the chain length and number of double bonds, separated by a colon; the 16-carbon saturated palmitic acid is abbreviated 16:0, and the 18-carbon oleic acid, with one double bond, is 18:1. The positions of any double bonds are specified by superscript numbers following $\Delta$ (delta); a 20-carbon fatty acid with one double bond between C-9 and C-10 (C-1 being the carboxyl carbon), and another between C-12 and C-13, is designated 20:2 ($\Delta$9,12), for example. The most commonly occurring fatty acids have even numbers of carbon atoms in an unbranched chain of 12 to 24 carbons. The even number of carbons results from the mode of synthesis of these compounds, which involves condensation of acetate (two-carbon) units. (Lehninger et al., Principles of Biochemistry, Vol. 1, Macmillan, 2005).

The position of double bonds in unsaturated fatty acids also is irregular; in most monounsaturated fatty acids, the double bond is between C-9 and C-10 ($\Delta$9), and the other double bonds of polyunsaturated fatty acids are generally $\Delta$12 and $\Delta$15. The double bonds of polyunsaturated fatty acids are almost never conjugated (alternating single and double bonds), but commonly are separated by a methylene group ($-CH=CH-CH_2-CH=CH-$). The physical properties of the fatty acids, and of compounds that contain them, are largely determined by the length and degree of unsaturation of the hydrocarbon chain, i.e., the longer the fatty acyl chain and the fewer the double bonds, the lower the solubility in water. (Lehninger et al., Principles of Biochemistry, Volume 1, Macmillan, 2005).

2.1 Fatty Acid Composition of Algae and Cyanobacteria

Algae are at the base of the trophic ladder of aquatic ecosystems, providing energy and essential nutrients for primary consumers. The major acyl lipid classes in algae are typically phospholipids (e.g., phosphatidylcholine, phosphatidylethanolamine, phosphatidylserine, phosphatidylglycerol, phosphatidylinositol), glycolipids (e.g., monogalactosyldiglycerol, digalactosyl glycerol sulfolipids), triacylglycerols, sterol esters, and free fatty acids. Phospholipids are structural constituents of cellular membranes, whereas glycolipids are major components of the thylakoid membrane in chloroplasts. Triacylglycerols produced by some algal species may be present as intracellular storage material and can occur as clearly visible oil droplets. Sterol esters are normally minor lipid constituents in plants (Arts and Wainman, Lipids in Freshwater Ecosystems, Springer, 1998).

Cyanobacterial cells are observed to resemble chloroplasts of eukaryotic plants in terms of membrane structure and glycerolipid composition. There are three types of membrane in the cyanobacterial cells, namely, the plasma membrane, the outer membrane, and the thylakoid membranes. The thylakoid membranes are closed systems and are separated from the plasma membrane. This architecture corresponds to that of the eukaryotic chloroplasts, which has inner and outer envelope membranes and thylakoid membranes. (Murata and Wada, Biochem. J., 1995, 308: 1-8).

The major nonpigment lipids of cyanobacteria have been identified as monogalactosyldiacylglycerol (MGDG), digalactosyldiacylglyerol (DGDG), phosphatidylglycerol, and sulfoquinovosyldiacylglycerol. Other lipids observed to occur in lesser amounts include fatty acids, sterols, hydrocarbons, and heterocyst glycolipids (glycosides of long chain diols, triols, and hydroxy acids). Cyanobacteria are not known to contain phosphatidylcholine, -ethanolamine, -serine, -inositol, and diphosphatidylglycerol (cardiolipin) (Ikawa et al., J. Chem. Ecol., 1994, 20: 2429-2436).

2.2 Fatty Acid Biosynthesis

The irreversible formation of malonyl-CoA from acetyl-CoA is catalyzed by acetyl-CoA carboxylase in what is considered to be the first committed step in fatty acid biosynthesis (FIG. 1). Acetyl-CoA carboxylase contains biotin as its prosthetic group, covalently bound in amide linkage to the s-amino group of a Lys residue on one of the three subunits of the enzyme molecule. The carboxyl group, derived from bicarbonate (HCO3-), is first transferred to biotin in an ATP-dependent reaction. The biotinyl group serves as a temporary carrier of CO2, transferring it to acetyl-CoA in the second step to yield malonyl-CoA. (Lehninger et al., Principles of Biochemistry, Volume 1, Macmillan, 2005).

In contrast to other heterotrophic bacteria, such as E. coli, which have to metabolize glucose from media into acetyl-CoA in order to initiate the fatty acid synthesis, in cyanobacteria, the precursor for fatty acid synthesis, i.e., acetyl-CoA, directly comes from the Calvin-Benson cycle which fixes carbon dioxide using energy and reducing power provided by the light reactions of photosynthesis.

The reaction sequence by which the long chains of carbon atoms in fatty acids are assembled consists of four steps: (1) condensation; (2) reduction; (3) dehydration; and (4) reduction. The saturated acyl group produced during this set of reactions is recycled to become the substrate in another condensation with an activated malonyl group. With each passage through the cycle, the fatty acyl chain is extended by two carbons. In many cells, chain elongation terminates when the chain reaches 16 carbons, and the product (palmitate, 16:0) leaves the cycle. The methyl and carboxyl carbon atoms of the acetyl group become C-16 and C-15, respectively, of the palmitate; the rest of the carbon atoms are derived from malonyl-CoA. All of the reactions in the synthetic process are catalyzed by a multienzymatic complex, the fatty acid synthase (Lehninger et al., Principles of Biochemistry, Volume 1, Macmillan, 2005).

2.3. The Elongation Cycle in Fatty Acid Synthesis

Fatty acid synthesis represents a central, conserved process by which acyl chains are produced for utilization in a number of end-products such as biological membranes. The enzyme system, which catalyzes the synthesis of saturated long-chain fatty acids from acetyl CoA, malonyl-CoA, and NADPH, is called the fatty acid synthase (FAS) (FIG. 1). Fatty acid synthases (FASs) can be divided into two classes, type I and II, which are primarily present in eukaryotes and in bacteria and plants respectively. They are characterized by being composed of either large multifunctional polypeptides in the case of type I or consisting of discretely expressed mono-functional proteins in the type II system. (Chan D. and Vogel H, Biochem J., 2010, 430(1):1-19). The fatty acid synthase contains six catalytic activities and contains beta-ketoacyl synthase (KS), acetyl/malonyl transacylase (AT/MT), beta-hydroxyacyl dehydratase (DH), enoyl reductase (ER), beta-ketoacyl reductase (KR), acyl carrier protein (ACP), and thioesterase (TE) (Chirala and Wakil, Lipids, 2004, 39(11): 1045-53). It has been shown that the reactions leading to fatty acid synthesis in higher organisms are very much like those of bacteria (Berg et al, Biochemistry, 6th ed., Macillan, 2008).

Fatty acid biosynthesis is initiated by the fatty acid synthase component enzyme acetyltransferase loading the acyl primer, usually acetate, from coenzyme A (CoA) to a specific binding site on fatty acid synthase (FAS). At the end of the process, termination of chain elongation occurs by removing the product from the fatty acid synthase (FAS) either by transesterification to an appropriate acceptor or by hydrolysis. The respective enzymes are usually palmitoyl transferase and thioesterase. The reaction sequence between initiation and termination involves the elongation of enzyme-bound intermediates by several iterative cycles of a distinct set of reaction steps. Each cycle includes (i) malonyl-transacylation from CoA to the enzyme by malonyl transferase; (ii) condensation of acyl-enzyme with enzyme-bound malonate to 3-ketoacyl-enzyme by 3-ketoacyl synthase, (iii) reduction of the 3-keto- to the 3-hydroxyacyl intermediate by ketoacyl reductase, (iv) dehydration of 3-hydroxyacyl enzyme to 2,3-transenoate by dehydratase, and, (v) finally, reduction of the enoate to the saturated acyl-enzyme by enoyl reductase. The prosthetic group, 4'-phosphopantetheine, plays a central role in substrate binding, processing of intermediates, and communicating of intermediates between the various catalytic centers of fatty acid synthase (FAS). This cofactor is bound covalently to a specific serine hydroxyl group of the ACP domain or, depending on the FAS system, to the ACP component of FAS. In some bacteria, the iterative sequence of elongation cycles may be interrupted at a chain length of 10 carbons by one cycle involving an intrinsic isomerase converting the 2-trans- into the 3-cis-decenoyl intermediate, which is subsequently not reduced but further elongated to long-chain monounsaturated fatty acids (Schweizer and Hofmann, Microbiol Mol Biol Rev., 2004, 68(3): 501-17).

3. Acyl Carrier Protein (ACP)

The acyl carrier protein (ACP), the cofactor protein that covalently binds fatty acyl intermediates via a phosphopantetheine linker during the synthesis process, is central to fatty acid synthesis. It is a highly conserved protein that carries acyl intermediates during fatty acid synthesis. ACP supplies acyl chains for lipid and lipoic acid synthesis, as well as for quorum sensing, bioluminescence and toxin activation. Furthermore, ACPs or PCPs (peptidyl carrier proteins) also are utilized in polypeptide and non-ribosomal peptide synthesis, which produce important secondary metabolites, such as, the lipopeptide antibiotic daptomycin and the iron-carrying siderophore enterobactin (Chan and Vogel, Biochem. J., 2010, 430:1-19).

In yeast and mammals, ACP exists as a separate domain within a large multifunctional fatty acid synthase polyprotein (type I FAS), whereas it is a small monomeric protein in bacteria and plants (type II FAS) (Byers and Gong, Biochem Cell Biol., 2007, 85(6): 649-62).

In *E. coli*, ACP is highly abundant, comprising approximately 0.25% of all soluble proteins and it represents one of four major protein-protein interaction hubs, the others being DNA and RNA polymerases as well as ribosome-associated proteins. In type I FAS systems, ACP is part of large, multidomain polypeptides that also carry the other protein domains for FA synthesis in a linear fashion. Although the architecture and sequence identity of the type I FAS systems are different from the type II dissociated enzymes, many of the functional units in these complexes are similar. On the other hand, other domains, such as the enoyl reductase and dehydratase enzymes, vary significantly between the type Ia, Ib and II systems (Chan and Vogel, Biochem. J., 2010, 430:1-19).

4. Acyl-ACP Thioesterases

The major termination reaction of fatty acid biosynthesis is catalyzed by acyl-acyl carrier protein (acyl-ACP) thioesterases in eukaryotes. Previous studies have shown that the acyl-ACP thioesterase enzyme terminates acyl elongation of a fatty acyl group by hydrolyzing an acyl group on a fatty acid. In plants, an acyl-ACP thioesterase terminates the acyl elongation process by hydrolysis of the acyl-ACP thioester; free fatty acid then is released from the fatty acid synthase. In *E. coli*, the long-chain acyl group is transferred directly from ACP to glycerol-3-phosphate by a glycerol-3-phosphate acyltransferase, and free fatty acids normally are not found as intermediates in lipid biosynthesis. As in most other organisms, the major end products of the plant and *E. coli* fatty acid synthase are usually 16- or 18-carbon fatty acids. Chain length is determined by the 3-ketoacyl-ACP synthases I and II and the glycerol-3-phosphate acyltransferase in *E. coli*. (Voelker and Davies, J. Bacteriol, 1994, 17: 7320-7327)

4.1. Plant Acyl-ACP Thioesterases

Acyl-ACP thioesterases have been studied extensively in plants. In plants, de novo fatty acid synthesis occurs in the stroma of plastids, where the acyl chains are covalently bound to a soluble acyl carrier protein (ACP) during the extension cycles. Carbon chain elongation can be terminated by transferring the acyl group to glycerol 3-phosphate, thereby retaining it in the plastidial "prokaryotic" lipid biosynthesis pathway. Alternately, specific thioesterases can intercept the prokaryotic pathway by hydrolyzing the newly formed acyl-ACP into free fatty acids and ACP. Subsequently, the free fatty acids exit the plastids by an undetermined mechanism and supply the "eukaryotic" lipid biosynthesis pathway. The latter is located in the endoplasmic reticulum and is responsible for the formation of phospholipids, triglycerides, and other neutral lipids. By catalyzing the first committed step in the eukaryotic lipid biosynthesis pathway in plant cells, acyl-ACP thioesterases play a crucial role in the distribution of de novo synthesized acyl groups between the two pathways (Lohden and Frentzen, Planta, 1988, 176: 506-512; Browse and Somerville, Plant Mol. Biol, 1991, 42: 467-506; and Gibson et al., Plant Cell Environ, 1994, 17: 627-637).

Acyl-ACP thioesterases play an essential role in chain termination during de novo fatty acid synthesis and in the channeling of carbon flux between the two lipid biosynthesis pathways in plants. There are two distinct but related thioesterase gene classes in higher plants, termed FatA and FatB. FatA encodes a C18:1-ACP thioesterase. In contrast, FatB encodes thioesterases preferring acyl-ACPs having saturated acyl groups (Jones et al., Plant Cell, 1995, 7(3):359-71).

Among prokaryotes, acyl groups exiting the dissociable fatty acid synthase are transferred directly from ACP to polar lipids. In contrast, plants must also release sufficient fatty acid from ACP to supply the extraplastidial compartments. Analysis of cloned plant thioesterases suggested that plants possess individual thioesterases with specificity either for C18:1 or for one or more saturated fatty acids (Vance et al., Biochemistry of Lipids, Lipoproteins, and Membranes, Elsevier, 1996). The most prominent thioesterase in most plants has a strong preference for C18:1-ACP, making C18:1 the fatty acid most available for extraplastidial glycerolipid synthesis. Several plant species that produce storage oils containing large amounts of fatty acids having an acyl chain length from 8 to 14 carbons contain thioesterases specific for those acyl chain lengths. By removing acyl groups from ACP prematurely, the medium-chain thioesterase simultaneously prevents further chain elongation and releases fatty acids for triacylglycerol synthesis outside the plastids. Thus, by regulating expression of different thioesterases, plants can both fine tune and radically modify the exported fatty acid pool (Vance et al., Biochemistry of Lipids, Lipoproteins, and Membranes, Elsevier, 1996).

The acyl-ACP hydrolytic specificities of five FatA representatives from three families have been measured in vitro after heterologous expression in *E. coli*. All FatA thioesterases appeared to be C18:1 specific, with minor activities on C18:0 and C16:0 substrates (Knutzon et al., Plant Physiol, 1992, 100(4):1751-1758; Dormann et al., Plant Physiol., 1994, 104(3): 839-844). In contrast to the conserved nature of FatA, the specificities of FatB enzymes show high variability. The California bay *Umbellularia californica* (Uc) FatB1 has a strong preference for C12:0 ACP (and a modest preference for C14:0-ACP; Voelker and Davies, J. Bacteriol., 1994, 176(23): 7320-7327). A *C. hookeriana* thioesterase, encoded by ChFatB2, has been characterized and found to hydrolyze C8:0 and C10:0 ACP; it is the enzyme involved in C8:0 and C10:0 fatty acid production for the storage lipids in seed. In addition, the specificity of a FatB representative from elm (*U. americana*) seed, Ua FatB1, shows that this enzyme is involved in C10:0 production for the elm storage lipids (80 mol % 10:0; Davies, H., Phytochemistry, 1993, 33:1353-1356). Medium chain-preferring FatB representatives may be common, if not universal, components of the fatty acid synthases specialized for medium-chain production in oilseeds (Jones and Davies, Plant Cell, 1995, 7(3): 359-371). Fat A and Fat B plant acyl-ACP thioesterase enzymes contain a targeting peptide at the N-terminal, which transports the expressed enzymes to the chloroplast where the biosynthesis of fatty acid occurs in plants. When expressed in bacteria, these higher plant thioesterase genes generally are N-terminally truncated in order to remove the chloroplast targeting peptide (Jones and Davies, Plant Cell, 1995, 7(3): 359-371). *E. coli* and many other prokaryotes do not have acyl-ACP thioesterases (Jones and Davies, Plant Cell, 1995, 7(3): 359-371), but some prokaryotes do have acyl-CoA thioesterases that cleave acyl chains from coenzyme A, which serves as a cofactor in fatty acid degradation.

Current understanding of the role of the acyl-CoA thioesterases in fatty acid metabolism is incomplete. The *E. coli* acyl-CoA thioesterase TesA (Thioesterase I), for example, is a periplasmic enzyme, but whether it functions in lipid synthesis, recycling, or degradation is unclear. Genes encoding N-terminally truncated TesA or N-terminally truncated TesA variants have been expressed in bacteria. These proteins lack a secretion sequence, and remain in the cytoplasm, where they are able to cleave acyl-ACPs.

For example, U.S. Pat. No. 5,455,167 discloses genes and constructs for expressing genes encoding higher plant acyl-ACP thioesterases, as well as a construct for expressing a gene encoding the *Vibrio harveyi* LuxD acyl transferase (YP_001448362.1 GI:156977456), belonging to pfam PF02273, in higher plants. PCT Publication No. WO2007/136762 discloses recombinant microorganisms engineered for the fermentative production of fatty acid derivatives, such as, inter alia, fatty alcohols and wax esters, in which the host strain can express a higher plant thioesterase or the *E. coli* TesA acyl-CoA thioesterase. PCT Publication No. WO2008/100251 describes methods for engineering microorganisms that include genes encoding synthetic cellulosomes to produce hydrocarbon products (which may be, inter alia, alkanes, alkenes, alkynes, dienes, fatty acids, isoprenoids, fatty alcohols, fatty acid esters, polyhydroxyalkanoates, organic acids, and the like). The microorganism that contains one or more exogenous nucleic acid sequence encoding a synthetic cellulosome can also include an exogenous thioesterase gene, such as the *E. coli* TesA acyl-CoA thioesterase or a plant thioesterase gene, which can be expressed in the host cells.

Other applications disclosing microorganisms, including algae, engineered to express heterologous acyl-ACP thioesterases from higher plants or acyl-CoA thioesterases from *E. coli* for the production of various compounds, including, inter alia, fatty acids or fatty acid derivatives, include PCT Publication Nos. WO2008/151149, WO2009/076559, and WO2009036385, as well as PCT Publication Nos. WO2009/111513, WO2010/022090, and WO2010/118410.

SUMMARY

One aspect of the invention relates to a photosynthetic microorganism that includes a recombinant nucleic acid molecule (e.g., a recombinant gene) that encodes a prokaryotic acyl-acyl carrier protein (acyl-ACP) thioesterase and produces at least one free fatty acid and/or fatty acid derivative, e.g., by expressing the gene encoding the prokaryotic acyl-ACP thioesterase.

In most embodiments, the photosynthetic microorganism that includes a recombinant nucleic acid molecule encoding a prokaryotic acyl-ACP thioesterase can produce at least one free fatty acid and/or fatty acid derivative, in which the amount of at least one free fatty acid and/or derivative produced by the photosynthetic microorganism can be greater than the amount produced by a photosynthetic microorganism that does not include the recombinant nucleic acid molecule encoding the prokaryotic acyl-ACP thioesterase. For example, the photosynthetic microorganism that include the recombinant nucleic acid molecule encoding the prokaryotic acyl-ACP thioesterase can produce at least 5 mg per liter, for example at least 10 mg per liter, per liter, at least 20 mg per liter, at least 30 mg per liter, at least 40 mg per liter, or at least 50 mg per liter, of free fatty acids and/or derivatives, for example, produced over a period from six hours to ten days.

Additionally or alternately, at least one free fatty acid and/or derivative produced by the photosynthetic microorganism that includes a recombinant gene that encodes a prokaryotic acyl-ACP thioesterase can have an acyl chain length from 8 to 24 carbons, for example, an acyl chain length from 8 to 18 carbons or an acyl chain length from 12 to 16 carbons. For example, at least one free fatty acid and/or derivative produced by the photosynthetic microorganism can have an acyl chain length of 8, 10, 12, 14, 16, 18, 20, 22, and/or 24 carbons. In cases where the fatty acid derivative comprises a wax ester, the wax ester comprises A chain carbons, as well as acyl chain carbons (B chain carbons), where the B chain can include 8, 10, 12, 14, 16, 18, 20, 22, and/or 24 carbons. In cases where the fatty acid derivative comprises one or more compounds that do not exhibit a carbonyl group (e.g., fatty alcohols, alkanes, and alkenes), the "acyl" chain length of such compounds should be understood to correspond herein to the total number of carbons in those molecules.

Further additionally or alternately, the photosynthetic microorganism that includes at least one recombinant gene encoding a prokaryotic acyl-ACP thioesterase can produce at least one fatty acid derivative, such as, but not limited to, one or more fatty aldehydes, fatty alcohols, wax esters, alkanes, alkenes, and/or a combination thereof. For example, the photosynthetic microorganism can produce at least one fatty acid derivative having a total number of carbons from 7 to 36, for example, from 7 to 34 or from 11 to 32 carbons. Additionally or alternately, at least one fatty acid derivative produced by the photosynthetic microorganism can have a total number of carbons of 7, 8, 9, 10, 11, 12, 13, 14, 15, 16, 17, 18, 19, 20, 21, 22, 23, 24, 26, 28, 30, 32, 34, and/or 36.

Still further additionally or alternately, at least 30 wt %, for example at least 40 wt %, at least 50 wt %, or at least 60 wt %, of the free fatty acids and/or derivatives produced by the photosynthetic microorganism that includes an recombinant gene encoding a prokaryotic acyl-ACP thioesterase can be free fatty acids having an acyl chain length of 8, 10, 12, 14, 16, and/or 18 carbons and/or fatty acid derivatives having a total number of carbons of 7, 8, 9, 10, 11, 12, 13, 14, 15, 16, 17, 18, 19, 20, 21, 22, 23, 24, 26, 28, 30, 32, 34, and/or 36.

Yet further additionally or alternately, the genetically engineered photosynthetic microorganism provided herein can include a recombinant nucleic acid molecule encoding a prokaryotic acyl-ACP thioesterase that is a member of Pfam family PF01643. Yet still further additionally or alternately, the photosynthetic microorganism can encode a prokaryotic acyl-ACP thioesterase that includes Pfam domain PF01643, and the photosynthetic microorganism produces a fatty acid having an acyl chain length of 12, 14, and/or 16 carbons and/or a fatty acid derivative having a total number of carbons from 11 to 32.

Alternately or in addition, the genetically engineered microorganism can be a photosynthetic organism and/or can include a recombinant nucleic acid molecule encoding a prokaryotic acyl-ACP thioesterase having at least 70%, for example at least 75%, at least 80%, at least 85%, at least 90%, at least 95%, at least 96%, at least 97%, at least 98%, at least 99%, or about 100%, amino acid sequence identity to SEQ ID NO:1 or SEQ ID NO:2. Further additionally or alternately, the photosynthetic microorganism can produce a fatty acid having an acyl chain length of 12, 14, and/or 16 carbons and/or a fatty acid derivative having a total number of carbons from 11 to 32. In some embodiments, the photosynthetic microorganism contains a nucleic acid molecule that includes nucleotide sequence SEQ ID NO:3 or SEQ ID NO:4.

In some embodiments, the nucleic acid molecule encoding the prokaryotic acyl-ACP thioesterase can be stably integrated into a chromosome of the photosynthetic microorganism. Additionally or alternately, the nucleic acid encoding the prokaryotic acyl-ACP thioesterase can be in an autonomously replicating episome. For example, the nucleic acid encoding the prokaryotic acyl-ACP thioesterase present on an episome and/or integrated into the genome of the photosynthetic microorganism can be an exogenous nucleic acid molecule introduced into the host microorganism (or a progenitor of the host microorganism), and can also be a recombinant nucleic acid molecule produced by genetic engineering.

Further additionally or alternatively, the genetically engineered photosynthetic microorganism can include an expression construct that includes the nucleic acid molecule encoding the prokaryotic acyl-ACP thioesterase and one or more additional sequences that regulate expression of the acyl-ACP thioesterase gene. For example, the expression construct can include a promoter operative in the host cells, where the promoter can be, for example, a bacterial, viral, phage, or eukaryotic promoter. Alternately, the promoter can be a synthetic promoter. Further, a promoter in an expression construct that includes a gene encoding an acyl-ACP thioesterase can be a constitutive promoter, or, in alternate embodiments, can be an inducible promoter. For example, the inducible promoter can be controlled by lactose or a lactose analogue, and/or can be controlled by light and can be, for example, a secA promoter, an rbc promoter, a psaAB promoter, or a psbA promoter.

Still further additionally or alternately, the photosynthetic microorganism of the described invention that includes a recombinant nucleic acid molecule encoding a prokaryotic acyl-ACP thioesterase can further comprise a recombinant nucleic acid molecule encoding an acetyl-CoA carboxylase and/or a recombinant nucleic acid molecule encoding a β-ketoacyl synthase (KAS). Yet further additionally or alternatively, the photosynthetic microorganism of the described invention can have attenuated/disrupted expression of one or more genes encoding acyl-ACP synthase, acyl-CoA synthase, acyl-CoA dehydrogenase, glycerol-3-phosphate dehydrogenase, acetaldehyde-CoA dehydrogenase, pyruvate dehydrogenase, or acetate kinase. For example, any of these genes can be knocked out by insertional mutagenesis and/or downregulated via RNA interference or via antisense RNA-mediated gene silencing.

The genetically engineered photosynthetic microorganism in any of the embodiments provided herein can be, for example, a microalga. For example, the photosynthetic microorganism can be a species of microalgal genus including, but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pav-* lova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella, and Volvox.

More particularly, the photosynthetic microorganism can be a prokaryotic microorganism. For example, the photosynthetic microorganism can be a species of cyanobacterial genus, including, but not limited to, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema, and Xenococcus.

According to another aspect, the present invention provides a culture for producing a free fatty acid and/or derivative comprising a population of photosynthetic microorganisms that can comprise a recombinant nucleic acid molecule encoding a prokaryotic acyl-ACP thioesterase. In certain embodiments, the growth media of the culture does not include a reduced carbon source, or at least a substantial amount of a reduced carbon source, where a substantial amount is an amount that can support growth of the culture in the absence of another energy source.

In one preferred embodiment, the microorganisms in the culture of the present invention can produce (and optionally but preferably release and/or secrete) at least one free fatty acid and/or fatty acid derivative. Additionally or alternately, the microorganisms in the culture can produce a greater amount of a fatty acid and/or fatty acid derivative than a culture of the same photosynthetic microorganism that does not include a recombinant nucleic acid molecule encoding a prokaryotic acyl-ACP thioesterase, in which the culture is identical in other respects. Further additionally or alternately, the microorganisms in the culture can includes a recombinant nucleic acid molecule encoding an acyl-ACP thioesterase, in which the culture can further include at least 5 mg per liter, for example at least 10 mg per liter, at least 20 mg per liter, at least 30 mg per liter, at least 40 mg per liter, or at least 50 mg per liter, of free fatty acids and/or fatty acid derivatives, for example, produced over a period from six hours to ten days. The fatty acids and/or fatty acid derivatives can be present in the media, for example, as precipitates in or on, at or near the surface of, the media, associated with the media vessel as droplets, including suspended droplets (e.g., an emulsion), as a relatively immiscible layer floating on top of the aqueous culture medium, as a "scum", film, gel, semi-solid, colloid, fine particulate, particulate, solid, or aggregate that may be dispersed, suspended, or entrained within the culture medium, associated with the cells of the photosynthetic microorganism, phase separated in some other fashion, or a combination thereof.

Additionally or alternately, the growth medium of the culture may not include a substantial amount of a reduced carbon source, where a substantial amount is an amount that can support growth of the culture in the absence of another energy source that can be used by the microorganisms. Further, additionally or alternately, a culture can be provided with at least one source of inorganic carbon, such as, for example, bicarbonate or carbon dioxide ($CO_2$), and/or the photosynthetic microorganisms in the culture can be exposed to light for at least a portion of the culturing period.

Additionally, a free fatty acid and/or derivative can be isolated from the culture, e.g., from the cells, the growth media, or the whole culture. For example, the isolation can be by organic extraction of whole and/or lysed cells, via removal of free fatty acids and/or derivatives as precipitates (e.g., from the upper layer of the culture media, also termed "skimming"), through the use of particulate adsorbents, bubbles, and/or matrices that can bind the fatty acids or fatty acid derivatives, or combinations thereof.

DETAILED DESCRIPTION

Figure 1:
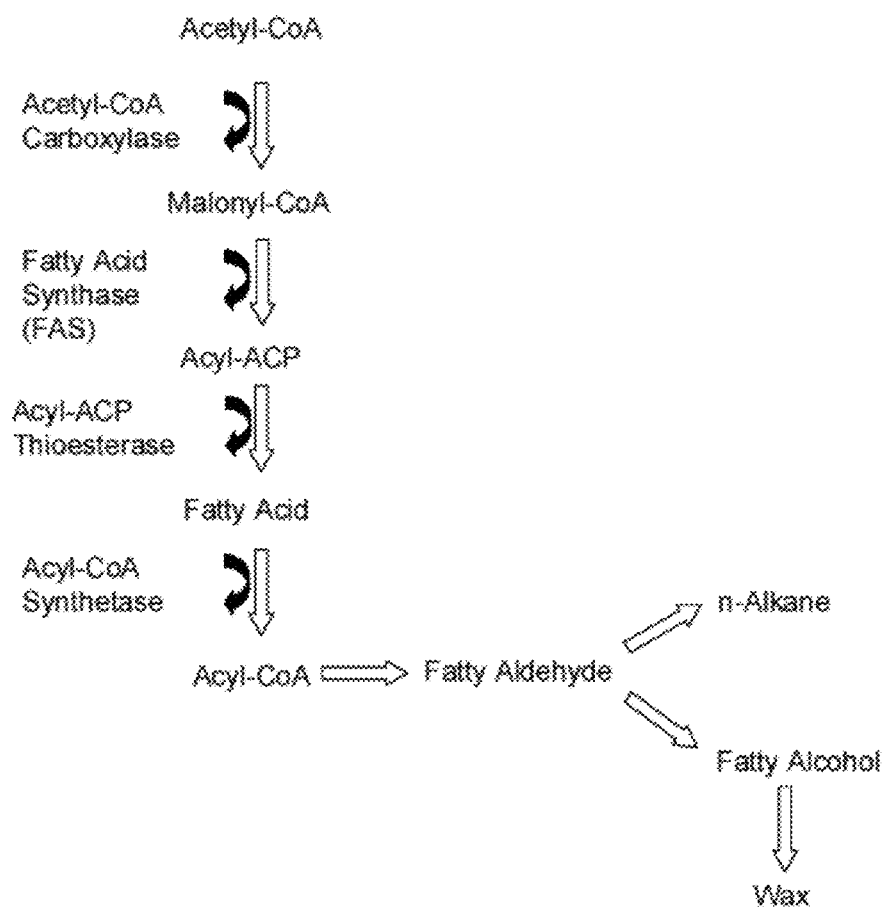
FIG. 1 shows a schematic diagram of the biosynthetic pathway for producing free fatty acids and fatty acid derivatives.

The described invention provides a composition and method for producing one or more free fatty acids and/or derivatives thereof comprising expressing a prokaryotic acyl-ACP thioesterase in a microorganism (e.g., by expressing a recombinant gene encoding a prokaryotic acyl-ACP thioesterase).

GLOSSARY

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered, for example, so as to increase the half-life of the peptide or to modify the activity of the peptide, or to increase the bioavailability of the peptide.

The phrase "conservative amino acid substitution" or "conservative mutation" as used herein refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner can include: a "charged/polar group," including Glu, Asp, Asn, Gln, Lys, Arg, and His; an "aromatic or cyclic group," including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group," comprising Lys, Arg and His; the "negatively-charged sub-group," comprising Glu and Asp; and the "polar sub-group" comprising Asn and Gln. In another example, the aromatic or cyclic group can be sub-divided into sub-groups including: the "nitrogen ring sub-group," comprising Pro, His, and Trp; and the "phenyl sub-group" comprising Phe and Tyr. In another further example, the aliphatic group can be sub-divided into sub-groups including: the "large aliphatic non-polar sub-group," comprising Val, Leu, and Ile; the "aliphatic slightly-polar sub-group," comprising Met, Ser, Thr, and Cys; and the "small-residue sub-group," comprising Gly and Ala. Examples of conservative mutations include amino acid substitutions of amino acids within the sub-groups above, such as, but not limited to:

Alanine (A), Serine (S), Threonine (T);
Aspartic Acid (D), Glutamic Acid (E);
Asparagine (N), Glutamic Acid (Q);
Arginine (R), Lysine (K);
Isoleucine (I), Leucine (L), Methionine (M), Valine (V); and
Phenylalanine (F), Tyrosine (Y), Tryptophan (W).

The term "acyl-acyl carrier protein thioesterase" or "acyl-ACP thioesterase," as used herein, refers to a thioesterase enzyme that hydrolyzes an acyl-ACP ester linkage in preference to other substrates, such as an acyl-CoA substrate and/or a hydroxybenzoyl-CoA substrate (e.g., 4-hydroxybenzoyl-CoA, 2,5-dihydroxybenzoyl-CoA, or the like), and can include an acyl-ACP thioesterase belonging to Protein family (Pfam) PF01643 (at pfam.cgb.ki.se/; at pfam.janelia.org/; at pfam.sanger.ac.uk).

The term "attenuate," as used herein, means to weaken or reduce in force, intensity, activity, effect, or quantity.

The term "autotroph", as used herein, refers to an organism that produces complex organic compounds (carbohydrates, fats, and proteins) from simple inorganic molecules using energy from light (by photosynthesis) or inorganic chemical reactions. They are typically able to make their own food. Some autotrophs can fix carbon dioxide.

The term "autotrophic," as used herein, refers to an organism that is capable of producing complex organic compounds (carbohydrates, fats, and proteins) from simple inorganic molecules using energy from light (by photosynthesis) and/or inorganic chemical reactions. The term "photoautotrophic," as used herein, refers to an organism capable of producing complex organic compounds (carbohydrates, fats, and proteins) from simple inorganic molecules, which include carbon dioxide and other nonreduced sources of carbons, such as bicarbonate, using energy from light (by photosynthesis). "Phototrophic growth" is growth using light as an energy source, and does not require a reduced carbon source such as a sugar, carbohydrate, organic acid, amino acid, protein, lipid, etc.

The term "biofuel," as used herein, refers to any fuel that is obtained from a renewable biological resource.

The term "carbon source," as used herein, refers to a compound that provides carbon needed for biosynthesis of new organic molecules by a cell or microorganism.

The term "clade," as used herein, refers to a group of biological taxa or species that share features inherited from a common ancestor. A clade includes an ancestral lineage and all the descendants of that ancestor. The term clade is used also to refer to a grouping of genes or proteins by relatedness (homology) of their sequences.

A gene that is "codon-optimized" for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except for methionine and tryptophan are encoded by more than one codon. For example, arginine, leucine, and serine are encoded by six different codons; and glycine, alanine, valine, threonine, and proline are encoded by four different codons. Many organisms use certain codons to encode a particular amino acid more frequently than others. Without limiting any aspects of the invention to any particular mechanism, it is believed that some tRNAs for a given amino acid are more prevalent than others within a particular organism, and genes requiring a rare tRNA for translation of the encoded protein may be expressed at a low level due in part to a limiting amount of the rare tRNA. Thus, for adequate or optimal levels of expression of an encoded protein, a gene may be "codon-optimized" to change one or more codons to new codons ("preferred codons") that are among those used more frequently in the genes of the host organism (referred to as the "codon preference" of the organism). As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently that the original codon(s), whether or not they are used most frequently in the organism to encode a particular amino acid.

The term "controllable regulatory element" or "regulatory element," as used herein, refers to nucleic acid sequences capable of effecting the expression of the nucleic acids, or the peptide or protein product thereof. Controllable regulatory elements may be operably linked to the nucleic acids, peptides, or proteins of the present invention. The controllable regulatory elements, such as, but not limited to, control sequences, need not be contiguous with the nucleic acids, peptides, or proteins whose expression they control as long as they function to direct the expression thereof. Thus, for example, intervening untranslated yet transcribed sequences may be present between a promoter sequence and a nucleic acid of the present invention and the promoter sequence may still be considered "operably linked" to the coding sequence. Other such control sequences include, but are not limited to, enhancer sequences, sequences regulating translation, sequences regulating mRNA stability, polyadenylation signals, termination signals, and ribosome binding sites.

The term, "endogenous," as used herein, refers to substances originating or produced within an organism. An "endogenous" gene or protein is a gene or protein residing in a species that is also derived from that species.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native."

An "episome" is a nucleic acid molecule that is not integrated into the chromosome or chromosomes of the cell and replicates autonomously in a cell. An "episomal" nucleic acid molecule or sequence is a gene, nucleic acid molecule, or nucleic acid sequence that is integrated into an episome. An example of an episome is a plasmid, which is a circular DNA molecule outside of the chromosome(s) that includes an origin of replication and replicates autonomously within the cell.

"Expression construct" refers to a nucleic acid that has been generated via human intervention, including by recombinant means or direct chemical synthesis, with a series of specified nucleic acid elements that permit transcription and/or translation of a particular nucleic acid in a host cell. The expression construct can be part of a plasmid, virus, or nucleic acid fragment.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant cell. An "endogenous" nucleic acid molecule, gene, or protein can represent the organism's own gene or protein as it is naturally produced by the organism.

The term "expressing" or "expression," as used herein, means the transcription and translation of a nucleic acid molecule by a cell. Expression can be, for example, constitutive or regulated, such as, by an inducible promoter (e.g., lac operon, which can be triggered by Isopropyl β-D-1-thiogalactopyranoside (IPTG)).

The term "fatty acid," as used herein, is meant to refer to a non-esterified a carboxylic acid having an alkyl chain of at least 3 carbons (that is, having an acyl chain of at least 4 carbons) or its corresponding carboxylate anion, denoted as RCOOH or RCOO— respectively, where R is an alkyl chain of between 3 and 23 carbons. A "free fatty acid" is substantially unassociated, e.g., with a protein, within or outside an organism (e.g., globular and/or micellular storage within an organism, without esterification, can still qualify as a free fatty acid). Thus, a free fatty acid according to the present invention need not necessarily be a strict acid or be structurally "free", but a free fatty acid specifically does not include an acyl moiety whose carboxylate oxygen is covalently linked to any other moiety besides a hydrogen atom, meaning that fatty acid esters are specifically not included in free fatty acids. However, a free fatty acid can advantageously include an acyl moiety containing at least four carbons (for example, at least 6 carbons, for example at least 8 carbons), in which the acyl moiety (i) is covalently linked to a hydrogen atom, (ii) has an ionic charge, to which a counterion can be associated (even if loosely and/or solvent-separated), and/or (iii) is otherwise associated (not covalently) with a moiety other than hydrogen, for example, through an ester bond, such that a free fatty acid is relatively easily transformable into the corresponding acid form or the corresponding ionic form (e.g., through hydrogen-bonding or the like). Nonlimiting examples of counterions can include metals salts (such as calcium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof. The term "free fatty acids" as used herein also refers to fatty acids which are not covalently bound to any other moiety with the exception of hydrogen (bound by the carboxylic acid group). For example, a free fatty acid is not bound to other molecules such as ACP, coenzyme A (CoA), or glycerol (for example, as part of a triglyceride, diglyceride, monoglyceride, or phospholipid molecule). Free fatty acids contain a carboxyl group (—COOH), which can be ionized into an anionic carboxylate form (R—COO—; R: hydrocarbons).

Fatty acids can have an even or an odd number of carbon atoms (e.g., heptadecanoic=C17) and can also have branched chains (e.g., isopalmitic acid, anteisononadecanoic acid) or carbocyclic units (e.g., sterculic acid, chaulmoogric acid).

In some fatty acids, the hydrocarbon chain is fully saturated (meaning contains no double bonds) and unbranched; others contain one (monounsaturated) or more double bonds (unsaturated). A simplified nomenclature for these compounds specifies the chain length and number of double bonds, separated by a colon; the 16-carbon saturated palmitic acid is abbreviated 16:0, and the 18-carbon oleic acid, with one double bond, is 18:1. The positions of any double bonds are specified by superscript numbers following $\Delta$ (delta); a 20-carbon fatty acid with one double bond between C-9 and C-10 (C-1 being the carboxyl carbon), and another between C-12 and C-13, is designated 20:2 ($\Delta$9,12), for example. The most commonly occurring fatty acids have even numbers of carbon atoms in an unbranched chain of 12 to 24 carbons. The even number of carbons results from the mode of synthesis of these compounds, which involves condensation of acetate (two-carbon) units. The position of double bonds is also regular; in most monounsaturated fatty acids, the double bond is between C-9 and C-10 ($\Delta$9), and other double bonds of polyunsaturated fatty acids are generally $\Delta$12 and $\Delta$15. The double bonds of almost all naturally-occurring unsaturated fatty acids are in the cis configuration. (Lehninger et al., Principles of Biochemistry, Vol. 1, Macmillan, 2005)

Examples of saturated fatty acids include, but are not limited to, butanoic (butyric) acid (C4), hexanoic (caproic) acid (C6), octanoic (caprylic) acid (C8), decanoic (capric) acid (C10), dodecanoic (lauric) acid (C12), tetradecanoic (myristic) acid (C14), hexadecanoic (palmitic) acid (C16), octadecanoic (stearic) acid (C18), and eicosanoic (arachidic) acid (C20), docosanoic (behenic) acid (C22), tetracosanoic (lignoceric) acid (C24). Examples of unsaturated fatty acids include, but are not limited to, myristoleic acid (C14:1, cis$\Delta$9), palmitoleic acid (C16:1, cis$\Delta$9), sapienic acid (C16:1, cis$\Delta$6), oleic acid (C18:1, cis$\Delta$9), linoleic acid (C18:2, cis$\Delta$9, cis, $\Delta$12), α-linolenic acid (C18:3, cis$\Delta$9, cis$\Delta$12, cis$\Delta$15), γ-linolenic acid (C18:3, cis$\Delta$6, cis$\Delta$9, cis$\Delta$12), arachidonic acid (C20:4, cis$\Delta$5, cis$\Delta$8, cis$\Delta$11, cis$\Delta$14), eicosapentaenoic acid (C20:5, cisΔ5, cisΔ8, cisΔ11, cisΔ14, cisΔ17), erucic acid (C22:1, cis-Δ13), and docosahexaenoic acid (C22:6, cisΔ4, cisΔ7, cisΔ10, cisΔ13, cisΔ16, cisΔ19). Long chain fatty acids also can be made from more readily available shorter chain fatty acids (C12-C18) by appropriate chain-extension procedures.

Nonlimiting examples of naturally-occurring branched-chain fatty acids include the iso fatty acids (mainly with an even number of carbon atoms) and the anteiso fatty acids (mainly with an odd number of carbon atoms), polymethyl branched acids in bacterial lipids, and phytol-based acids.

The most common cyclic acids contain a cyclopropane, cyclopropene, or cyclopentene unit. Cyclopropane acids occur in bacterial membrane phospholipids and are mainly C17 or C19 (lactobacillic) acids. The cyclopropane unit, like cis double bond, introduces a discontinuity in the molecule and increases fluidity in the membrane.

The physical properties of the fatty acids, and of compounds that contain them, are determined largely by the length and degree of unsaturation of the hydrocarbon chain. The nonpolar hydrocarbon chain accounts for the poor solubility of fatty acids in water. The longer the fatty acyl chain and the fewer the double bonds, the lower the solubility in water. The carboxylic acid group is polar (and ionized at neutral pH) and accounts for the slight solubility of short chain fatty acids in water. The melting points of fatty acids and of compounds that contain them are influenced also strongly by the length and degree of unsaturation of the hydrocarbon chain. In the fully saturated compounds, free rotation around each of the carbon-carbon bonds gives the hydrocarbon chain great flexibility; the most stable conformation is this fully extended form, in which the steric hindrance of neighboring atoms is minimized. These molecule can pack together tightly in nearly crystalline arrays, with atoms all along their lengths in van der Waals contact with the atoms of neighboring molecules. A cis double bond forces a kink in the hydrocarbon chain. Fatty acids with one or several of such kinks cannot pack together as tightly as fully saturated fatty acids and their interactions with each other are therefore weaker. Because it takes less thermal energy to disorder these poorly ordered arrays of unsaturated fatty acids, they have lower melting points than saturated fatty acids of the same chain length (Lehninger et al., Principles of Biochemistry, Vol. 1, Macmillan, 2005).

The term "fatty acid derivative," as used herein, refers to an organic molecule derived from a fatty acid. Examples of fatty acid derivative include, but are not limited to, C1-C5 fatty acid esters such as fatty acid methyl esters and fatty acid ethyl esters, wax esters, fatty alcohols, fatty aldehydes, alkanes, and alkanes.

The term "fatty alcohol," as used herein, refers to an alcohol made from a fatty acid or fatty acid derivative and having the formula ROH, where R is a hydrocarbon chain. The hydrocarbon chain of the fatty alcohol can be straight or branched. The hydrocarbon chain can be saturated or unsaturated.

The term "fatty aldehyde," as used herein, refers to an aldehyde made from a fatty acid or fatty acid derivative and having the formula RCHO, where R is a hydrocarbon chain. The hydrocarbon of the fatty aldehyde can be saturated or unsaturated.

The term "gene," as used herein, refers to a nucleic acid molecule that encodes a protein or functional RNA (for example, a tRNA). A gene can include regions that do not encode the final protein or RNA product, such as 5' or 3' untranslated regions, introns, ribosome binding sites, promoter or enhancer regions, or other associated and/or regulatory sequence regions.

The terms "gene expression" and "expression" are used interchangeably herein to refer to the process by which inheritable information from a gene, such as a DNA sequence, is made into a functional gene product, such as protein or RNA.

The term "genetic engineering," as used herein, refers to the use of molecular biology methods to manipulate nucleic acid sequences and introduce nucleic acid molecules into host organisms. The term "genetically engineered," as used herein, means a cell that has been subjected to recombinant DNA manipulations, such as the introduction of exogenous nucleic acid molecule, resulting in a cell that is in a form not found originally in nature.

The term "growth," as used herein, refers to a process of becoming larger, longer or more numerous, or can indicate an increase in size, number, or volume of cells in a cell population.

The term "heterotrophic," as used herein, refers to requiring reduced carbon substrates for growth.

The term "heterotroph," as used herein, refers to an organism that does not produce its own food and must acquire some of its nutrients from the environment, e.g., in the form of reduced carbon.

A "homolog" of a gene or protein refers to its functional equivalent in another species.

The term "hydrocarbon," as used herein, refers to any of the organic compounds made up exclusively of hydrogen and carbon in various ratios.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed.

The term "inducer," as used herein, refers to a molecule that can initiate the transcription of a gene, which is controlled by a inducible promoter.

The term "inducible promoter," as used herein, refers to a promoter, whose activity in promoting transcription of a gene to which it is operably linked is controlled by an environmental condition (e.g., temperature, light, or the like) or the presence of a factor such as a specific compound or biomolecule. The term "constitutive promoter" refers to a promoter whose activity is maintained at a relatively constant level in all cells of an organism with little or no regard to cell environmental conditions (as the concentration of a substrate).

The terms "inhibiting", "inhibit," and "inhibition," as used herein, refer to reducing the amount or rate of a process, to stopping the process entirely, or to decreasing, limiting, or blocking the action or function thereof. Inhibition may include a reduction or decrease of the amount, rate, action function, or process by at least 5%, for example at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%, when compared to a reference substance, wherein the reference substance is a substance that is not inhibited.

"Inorganic carbon" is a carbon-containing compound or molecule that cannot be used as an energy source by an organism. Typically "inorganic carbon" is in the form of CO2 (carbon dioxide), carbonic acid, bicarbonate, or carbonate, which cannot be oxidized for energy or used as a source of reducing power by organisms.

The term "insertional mutagenesis," as used herein, refers to a mutagenesis of DNA by the insertion of exogenous DNA into a gene.

The term "isolate," as used herein, refers to a process of obtaining a substance, molecule, protein, peptide, nucleic acid, or antibody that is substantially free of other substances with which it is ordinarily found in nature or in vivo systems to an extent practical and appropriate for its intended use.

The term "isolated" refers to a material, such as a nucleic acid, a peptide, or a protein, which is: (1) substantially or essentially free from components that normally accompany or interact with it as found in its naturally occurring environment, or (2) if the material is in its natural environment, the material has been synthetically (non-naturally) altered by deliberate human intervention to a composition and/or placed at a location in the cell (e.g., genome or subcellular organelle) not native to a material found in that environment. The term "substantially or essentially free" is used to refer to a material, which is at least 80% free, for example at least 90% free, at least 95% free, or at least 99% free (with percentages being weight percentages only when applicable) from components that normally accompany or interact with it as found in its naturally occurring environment. The isolated material optionally comprises material not found with the material in its natural environment.

The term "heterologous," as used herein, refers to nucleic acids derived from a different species than that into which they are introduced or than they reside in through genetic engineering of the organism or its ancestor. A heterologous protein is derived from a species other than that is produced in or introduced into. A heterologous nucleic acid sequence, gene, or protein, is a nucleic acid sequence, gene, or protein derived from an organism other than that it is introduced into or resides in.

When referring to gene regulatory elements, "heterologous" refers to a gene regulatory element that is operably linked to a gene with which it is not associated in nature. The term "heterologous expression," as used herein, means that a heterologous nucleic acid encoding a protein (e.g., an enzyme) is put into a cell that does not normally make (i.e., express) that protein.

The term "lactose analogue," as used herein, refers to a compound used as a substitute for lactose, wherein the glucose moiety of lactose is replaced by another chemical group. Examples of a lactose analogue include, but are not limited to, isopropyl-β-D-thio-galactoside (IPTG), phenyl-β-D-galactose (phenyl-Gal), and allolactose.

The term "lipid," as used herein, refers to a chemically diverse group of compounds, the common and defining feature being their insolubility in water.

The term "metabolic engineering," as used herein, generally refers to the targeted and purposeful alteration of metabolic pathways found in an organism in order to better understand and utilize cellular pathways for chemical transformation, energy transduction, and supramolecular assembly.

The term "metabolic intermediate," as used herein, refers to a precursor molecule produced by a series of enzymatic reactions, which is altered by the subsequent enzymatic reactions.

The term "microorganism" refers to a living organism so small in size that it is only visible with the aid of a microscope.

The term "mixotrophic," as used herein, refers to cells or organisms capable of using a mix of different sources of energy and carbon, for example, using phototrophy (meaning growth using energy from light) and chemotrophy (meaning growth using energy by the oxidation of electron donors), or between chemical autotrophy and heterotrophy.

The term "nucleic acid," as used herein, refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide," as used herein, refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The term "operably linked," as used herein, refers to a functional linkage between a genetic regulatory element or region and a second nucleic acid sequence, wherein the genetic regulatory element or region promotes, inhibits, terminates, initiates, or mediates transcription, translation, turnover, processing, or transport, of the nucleic acid sequence corresponding to the second sequence.

The term "origin of replication," as used herein, refers to a particular sequence in a genome, chromosome, or episome at which replication of DNA is initiated.

The term "open reading frame," as used herein, refers to a sequence of nucleotides in a DNA molecule that encodes a sequence of amino acids uninterrupted by a stop codon that has the potential to encode at least a portion of a peptide or protein. A complete open reading frame starts with a start codon (typically ATG), is followed by a string of codons each of which encodes an amino acid, and ends with a stop codon (TAA, TAG or TGA). Open reading frames often can be confirmed by matching their sequences to a database of sequenced genes or expressed sequence tags (ESTs).

The term "overexpressed," as used herein, refers to increased quantity of a gene or gene product relative to a quantity of the gene or gene product under normal conditions.

The term "peptide," as used herein, refers to a biopolymer formed from the linking together, in a defined order, of amino acids. The link between one amino acid residue and the next is known as an amide or peptide bond. The term "polypeptide," as used herein, refers to a single chain of amino acids, and a "protein" refers to one or more polypeptides. The terms polypeptide, peptide, and protein are also inclusive of modifications including, but not limited to, glycosylation, lipid attachment, sulfation, gamma-carboxylation of glutamic acid residues, hydroxylation and ADP-ribosylation. Polypeptides may not be entirely linear. For instance, polypeptides may be branched as a result of ubiquitination, and they may be circular, with or without branching, generally as a result of posttranslational events, including natural processing event and events brought about by human manipulation which do not occur naturally.

The term "Pfam" refers to a large collection of protein domains and protein families maintained by the Pfam Consortium and available at several sponsored world wide web sites, including: pfam.sanger.ac.uk/ (Welcome Trust, S anger Institute); pfam.sbc.su.se/(Stockholm Bioinformatics Center); pfam.janelia.org/(Janelia Farm, Howard Hughes Medical Institute); pfam.jouy.inra.fr/(Institut national de la Recherche Agronomique); and pfam.ccbb.re.kr/. A recent release of Pfam is Pfam 24.0 (October 2009, 11912 families) based on the UniProt protein database release 15.6, a composite of Swiss-Prot release 57.6 and TrEMBL release 40.6. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. All identified sequences belonging to the family are then used to automatically generate a full alignment for the family (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database, for example, using any of the above-reference websites, protein sequences can be queried against the hidden Markov models (HMMs) using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. The term "gathering threshold (GA)" or "gathering cut-off," as used herein, refers to a search threshold value used to build a full alignment. The gathering threshold is the minimum score that a sequence must attain in order to belong the full alignment of a Pfam entry. The gathering threshold for the Acyl-ACP thioesterase family (PF01643) is 20.3. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

The term "phototroph," as used herein, refers to an organism which uses sunlight as its primary energy source. "Phototrophic" growth or culture means growth or culture in which the organisms use light, and not organic molecules, for energy.

The term "photosynthetic microorganism," as used herein, includes, but is not limited to, all algae, microalgae, and photosynthetic bacteria, which can grow phototrophically.

The term "plasmid," as used herein, refers to a DNA molecule that is separate from, and can replicate independently of, the chromosomal DNA of a cell. It is double stranded and, in many cases, circular.

The term "polypeptide" is used herein to refer to a peptide containing from about 10 to more than about 1000 amino acids.

The term "polynucleotide" or "nucleic acid molecule" refers to a deoxyribopolynucleotide, ribopolynucleotide, or an analog thereof that has the essential nature of a natural deoxyribopolynucleotide or ribonucleotide in that it hybridizes, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes are known to those of skill in the art. The term polynucleotide, as it is employed herein, embraces such chemically, enzymatically or metabolically modified forms of polynucleotides, as well as the chemical forms of DNA and RNA characteristic of viruses and cells, including among other things, simple and complex cells.

The term "primer" refers to a nucleic acid molecule which, when hybridized to a strand of DNA or RNA, is capable of serving as the substrate to which nucleotides are added in the synthesis of an extension product in the presence of a suitable polymerization agent (e.g., a DNA polymerase). In some cases, the primer is sufficiently long to uniquely hybridize to a specific region of a DNA or RNA strand.

The term "promoter," as used herein, refers to a region of DNA proximal to the start site of transcription, which is involved in recognition and binding of RNA polymerase and other proteins to initiate transcription. A given promoter may work in concert with other regulatory regions (enhancers, silencers, boundary elements/insulators) in order to direct the level of transcription of a given gene.

The term "lac promoter," as used herein, refers to a promoter of the lac operon, whose transcription activity is repressed by a repressor protein (i.e., the LacI protein encoded by the lad gene) but relieved by an inducer, such as, lactose or analogues thereof (e.g., isopropyl-β-D-thiogalactoside (IPTG)). The inducer binds to the repressor protein and prevents it from repressing gene transcription.

The term "tac promoter," as used herein, refers to a strong hybrid promoter composed of the position -35 region of the trp promoter and the position -10 region of the lacUV5 promoter/operator. Expression of the tac promoter is repressed by the LacI protein. The lacIq allele is a promoter mutation that increases the intracellular concentration of the LacI repressor, resulting in strong repression of tac promoter. The transcriptional activity of the tac promoter is controlled by a lactose or analogues thereof.

The term "trc promoter," as used herein, refers to a hybrid promoter sequence of the lac and trp promoters. The transcriptional activity of the trc promoter also is controlled by lactose or analogues thereof. One example of a trc promoter is the trcY promoter (SEQ ID NO:9).

The term "recombination," as used herein, refers to the process by which pieces of DNA are broken apart and recombined. The term "homologous recombination," as used herein, refers to a type of genetic recombination in which nucleotide sequences are exchanged between two similar or identical molecules of DNA.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of an exogenous or recombinant nucleic acid sequence into the organism, and includes organisms having gene knockouts, targeted mutations and gene replacement, promoter replacement, deletion, or insertion, as well as organisms having exogenous genes that have been introduced into the organism. An exogenous or recombinant nucleic acid molecule can be integrated into the recombinant/genetically engineered organism's genome or in other instances may not be integrated into the recombinant/genetically engineered organism's genome.

The term "recombinant protein," as used herein, refers to a protein produced by genetic engineering.

The term "recombinase," as used herein, refers to an enzyme that catalyzes genetic recombination.

"Reduced carbon" or a "reduced carbon compound" or "reduced carbon source" refers to a carbon-based molecule that includes carbon and hydrogen and can be used as an energy source by an organism, either through oxidation or glycolysis. Non-limiting examples of reduced carbon are sugars (including polysaccharides and starch), alcohols (including glycerol and sugar alcohols), forms of organic acids (e.g., acetate, citrate, succinate, etc.), amino acids, proteins, lipids, and fatty acids. Reduced carbon is sometimes referred to as "organic carbon."

The term "regulatory sequence" (also referred to as a "regulatory region" or "regulatory element") refers to a promoter, enhancer, 5' untranslated region, 3' untranslated region, ribosome binding site, or other segment of DNA or RNA that regulate expression of a proximal gene.

The terms "amino acid residue" and "amino acid" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, for example at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA, 1989, 89:10915).

In addition to calculating percent sequence identity, the BLAST algorithm also performs a statistical analysis of the similarity between two sequences (see, e.g., Karlin & Altschul, Proc. Natl. Acad. Sci. USA, 1993, 90: 5873-5787). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 1993, 17:149-163) and XNU (Claverie and States, Comput. Chem., 1993, 17:191-201) low-complexity filters may be employed alone or in combination.

As used herein, "sequence identity" or "identity" in the context of two nucleic acid or polypeptide sequences refers to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g., charge and/or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 1988, 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise stated, % homology of a sequence is across the entire length of the query sequence (the comparison window).

The term "substantial identity" of polynucleotide sequences means that a polynucleotide comprises a sequence that has at least 70% sequence identity, for example at least 80% sequence identity, at least 85% sequence identity, at least 90% sequence identity, at least 95% sequence identity, at least 96% sequence identity, at least 97% sequence identity, at least 98% sequence identity, or at least 99% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, for example at least 70%, at least 80%, at least 85%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, for example at least 80%, at least 85%, at least 90%, at least 95%, at least 96%, at least 97%, at least 98%, or at least 99% sequence identity to the reference sequence, over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

A "variant" of a gene or nucleic acid sequence is a sequence having at least 65% identity with the referenced gene or nucleic acid sequence, and can include one or more base deletions, additions, or substitutions with respect to the referenced sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" of the original sequence.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

A "conservative variant" of a polypeptide is a polypeptide having one or more conservative amino acid substitutions with respect to the reference polypeptide, in which the activity, substrate affinity, binding affinity of the polypeptide does not substantially differ from that of the reference polypeptide.

A skilled artisan likewise can produce polypeptide variants having single or multiple amino acid substitutions, deletions, additions, and/or replacements. These variants may include, inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (e) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "specifically hybridizes," as used herein, refers to the process whereby a nucleic acid distinctively or definitively forms base pairs with complementary regions of at least one strand of the nucleic acid target sequence that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 85% sequence identity, at least 90% sequence identity, at least 95% sequence identity, at least 96% sequence identity, at least 97% sequence identity, at least 98% sequence identity, at least 99% sequence identity, or about 100% sequence identity (i.e., complementary) with each other.

The term "stably integrated," as used herein, means that an exogenous or heterologous genetic material is integrated into a host genome and is inherited by the descendants of the cell.

The term "thioesterase (TE)" or "thioester hydrolase," as used herein, refers to a large enzyme group whose members hydrolyze the thioester bond between a carbonyl group and a sulfur atom. They are classified by the Nomenclature Committee of the International Union of Biochemistry and Molecular Biology (NC-IUBMB) into EC (enzyme commission) 3.1.2.1 to EC 3.1.2.27, as well as EC 3.1.2.—for unclassified TEs. Substrates of 15 of these 27 groupings contain coenzyme A (CoA), two contain acyl carrier proteins (ACPs), four have glutathione or its derivatives, one has ubiquitin, and two contain other moieties. In addition, three groupings have been deleted (Cantu et al. (2010) Protein Science, 19:1281-1295).

The term "triacylglycerol" or "triglycerides," as used herein, refers to a class of compounds that consist of a glycerol backbone with a fatty acid linked to each of the three OH groups by an ester bond.

The term "transit peptide," as used herein, refers to a peptide sequence, often at the N-terminus of a precursor protein, which directs a gene product to its specific cellular destination, such as plastid.

The term "underexpressed," as used herein, refers to decreased quantity of a gene or gene product relative to the quantity of a gene or gene product under normal conditions.

The term "vector" is used herein to refer to any agent that acts as a carrier or transporter, such as a phage, plasmid, cosmid, bacmid, phage or virus, to which another genetic sequence or element (either DNA or RNA) may be attached so that sequence or element can be conveyed into a host cell.

The term "expression vector," as used herein, generally refers to a nucleic acid molecule that has been constructed in such as way that, after insertion of a DNA molecule, its coding sequence is properly transcribed into an RNA molecule and the RNA molecule can be optionally translated into a protein. The nucleic acid construct, which can be a vector, frequently is engineered to contain regulatory sequences that act as enhancer and promoter regions, which lead to efficient transcription of the open reading frame carried on the expression vector.

A "fatty acid ester" is an ester of a fatty acid and an alcohol. The carbon chain originating from an alcohol is referred to as the A chain and the carbon chain originating from a fatty acid (the fatty acid moiety can be provided by an acyl thioester) is referred to as the B chain. A fatty acid ester can have an A side of any length, for example, 1, 2, 3, 4, 5, 6, 7, 8, 9, 10, 12, 14, 16, 18, 20, 22, 24, or more than 24 carbons in length. A fatty acid ester can have a B side of any length, for example, 4, 6, 7, 8, 9, 10, 12, 14, 16, 18, 20, 22, 24, or more than 24 carbons in length. The lengths of the A and B chains of a fatty acid ester can vary independently. For example, condenstation of methanol (C1) and an acyl chain (fatty acid or acyl-thioester) of C4 or greater can result in a fatty acid methyl ester ("FAME") and condenstation of ethanol and an acyl chain can result in a fatty acid ethyl ester ("FAEE"). Condensation of a fatty acohol (C8 or above) with an acyl thioester (C8 or greater) produces a wax ester.

The term "wax" or "wax esters," as used herein, refers to esters of long chain fatty acids and monohydric straight chain aliphatic alcohols, which form solids or pliable substances under an identified set of physical conditions.

The term "wild type," as used herein, refers to an organism or phenotype as found in nature.

I. Genetically Engineered Microorganism for Producing Free Fatty Acids and/or Derivatives According to one aspect, the described invention provides a microorganism that includes a recombinant nucleic acid molecule that encodes a prokaryotic acyl-ACP thioesterase. The genetically engineered microorganism can produce at least one free fatty acid and/or fatty acid derivative.

Additionally or alternately, the amount of at least one free fatty acid and/or derivative produced by the genetically engineered microorganism can be at least twice the amount of the free fatty acid and/or derivative produced by the same microorganism that does not include a recombinant prokaryotic acyl-ACP thioesterase gene. For example, the photosynthetic microorganism that includes the recombinant nucleic acid molecule that encodes the prokaryotic acyl-ACP thioesterase can produce at least 30 mg per liter, for example at least 40 mg per liter or at least 50 mg per liter, of free fatty acids and/or derivatives. For example, the host microorganism can express prokaryotic thioesterase such that one or more fatty acids and/or derivates can be produced.

The genetically engineered microorganism can be any microorganism, including, but not limited to, a heterokont, fungus, bacterium, microalga, or cyanobacterium.

The genetically engineered host organism can additionally or alternately be a photosynthetic microorganism, such as, a microalga. Representative algae include green algae (chlorophytes), red algae, diatoms, prasinophytes, glaucophytes, chlorarachniophytes, euglenophytes, chromophytes, and dinoflagellates. Non-limiting examples of a microalgal genus that can contain an exogenous nucleic acid molecule encoding a prokaryotic acy-ACP thioesterase include, but are not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox*.

Alternately, the photosynthetic microorganism can be a cyanobacterial species. Non-limiting examples of a cyanobacterial genus that can include an exogenous nucleic acid molecule encoding a prokaryotic acyl-ACP thioesterase include, but are not limited to, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, and *Xenococcus*. For example, the photosynthetic microorganism can be a *Synechococcus, Synechocystis*, or *Thermosynechococcus* species. Alternatively, the photosynthetic microorganism can be a *Cyanobium, Cyanothece*, or *Cyanobacterium* species, or further alternatively, the photosynthetic microorganism can be a *Gloeobacter, Lyngbya* or *Leptolyngba* species.

The prokaryotic acyl-ACP thioesterase gene can be any prokaryotic acyl-ACP thioesterase gene that, when expressed in the microorganism, can result in the production of free fatty acids and/or derivatives by the microorganism. Prokaryotic acyl-ACP thioesterases considered useful herein can include members of the acyl-ACP thioesterase family (e.g., PF01643; see pfam.cgb.ki.se/ or pfam.janelia.org/ or pfam.sanger-.ac.uk/) that, when queried against the Pfam bioinformatics annotated database of protein families, can demonstrate a match with the Pfam acyl-ACP thioesterase family (PF01643) with a bit score higher than the threshold gathering score (for example, a bit score higher that 20.3), and/or can demonstrate a Pfam-A match with the Pfam acyl-ACP thioesterase family with an expectation value (e value) of less than 0.01 (Bateman et al. (2000) Nucleic Acids Research 28:263-266; Bateman et al. (2006) Nucleic Acids Research 32:D138-D141, Finn et al. (2010) Nucleic Acids Research 38:D211-222). Prokaryotic thioesterases expressed in a photosynthetic microorganism as provided herein in some embodiments have the EC designation EC 3.1.2.14.

Non-limiting examples of prokaryotic acyl-ACP thioesterases that can be used to transform a microorganism for producing fatty acids and fatty acid derivatives include, without limitation, the *Desulfovibrio desulfuricans* acyl-ACP thioesterase (SEQ ID NO:16) having Genbank Accession Number Q312L1 and GenInfo Identifier GI:123552742; the *Elusimicrobium minutum* acyl-ACP thioesterase (SEQ ID NO:17) having Genbank Accession Number ACC98705 and GenInfo Identifier GI:186971720; the *Carboxydothermus hydrogenoformans* acyl-ACP thioesterase (SEQ ID NO:18) having Genbank Accession Number YP_359670 and GenInfo Identifier GI:78042959; the *Clostridium thermocellum* acyl-ACP thioesterase (SEQ ID NO:2) having Genbank Accession Number YP_001039461 and GenInfo Identifier GI:125975551; the *Moorella thermoacetica* acyl-ACP thioesterase (SEQ ID NO:19) having Genbank Accession Number YP_431036 and GenInfo Identifier GI:83591027; the *Geobacter metallireducens* acyl-ACP thioesterase (SEQ ID NO:20) having Genbank Accession Number YP_384688 and GenInfo Identifier GI:78222941; the *Salinibacter ruber* acyl-ACP thioesterase (SEQ ID NO:21) having Genbank Accession Number YP_444210 and GenInfo Identifier GI:83814393; the *Microscilla marina* acyl-ACP thioesterase (SEQ ID NO:22) having Genbank Accession Number EAY28464 and GenInfo Identifier GI: 123988858; the *Parabacteroides distasonis* acyl-ACP thioesterase (SEQ ID NO:1) having Genbank Accession Number YP_001303423 and GenInfo Identifier GI:150008680; the *Enterococcus faecalis* acyl-ACP thioesterase (SEQ ID NO:23) having Genbank Accession Number: ZP_03949391 and GenInfo Identifier GI:227519342; the *lactobacillus plantarum* oleoyl-(acyl-ACP) thioesterase (SEQ ID NO:24) having Genbank Accession Number YP_003062170 and GenInfo Identifier GI:254555753; the *Leuconostoc mesenteroides* subsp. *mesenteroides* acyl-ACP thioesterase (SEQ ID NO:25) having Genbank Accession Number YP_817783 and GenInfo Identifier GI:116617412; the *Oenococcus oeni* acyl-ACP thioesterase (SEQ ID NO:26) having Genbank Accession Number: ZP_01544069 and GenInfo Identifier GI:118586629; the *Mycobacterium smegmatis* str. MC2 155 acyl-ACP thioesterase (SEQ ID NO:27) having Genbank Accession Number ABK74560 and GenInfo identifier GI:118173664; the *Mycobacterium vanbaalenii* PYR-1 acyl-ACP thioesterase (SEQ ID NO:28) having Genbank Accession Number ABM11638 and GenInfo Identifier GI:119954633; the *Rhodococcus erythropolis* SK121 acyl-ACP thioesterase (SEQ ID NO:29) having Genbank Accession Number ZP_04385507 and GenInfo Identifier GI:229491686; and the *Rhodococcus opacus* B4

ROP_16330 (SEQ ID NO:30) having Genbank Accession Number YP_002778825 and GenInfo Identifier GI:226361047.

Also considered herein are microorganisms that include nucleic acid molecules encoding variants of the above-listed acyl-ACP thioesterases, in which the variants have at least 70% identity, for example at least 75%, at least 80%, at least 85%, at least 90%, at least 95%, at least 96%, at least 97%, at least 98%, at least 99%, or about 100% identity, to the amino acid sequences accessed by the provided Genbank Accession Numbers, in which the variants have acyl-ACP thioesterase activity, and expression of the variant in a microorganism can result in production of a free fatty acid and/or derivative in an amount greater than (for example at least twice as much as) that produced by a microorganism that does not express the variant. Sequence-structure-function relationships for thioesterases have been advanced significantly in recent years (see, for example, Dillon and Bateman, BMC Bioinformatics 2004, 5:109; Mayer and Shanklin, J Biological Chem., 2005, 280: 3621-3627; Mayer and Shanklin, BMC Plant Biology, 2007, 7:1). A variant of a wild-type prokaryotic acyl-ACP thioesterase can have at least 70% identity with the amino acid sequence of a prokaryotic acyl-ACP thioesterase as provided hereinabove. A variant of a wild-type prokaryotic acyl-ACP thioesterase can have at least 75% identity, for example at least 80%, at least 85%, at least 90%, at least 95%, at least 96%, at least 97%, at least 98%, or at least 99%, identity, with a wild-type prokaryotic acyl-ACP thioesterase provided herein.

Additionally or alternately, the genetically engineered microorganism that includes a recombinant nucleic acid molecule encoding a prokaryotic acyl-ACP thioesterase can produce at least one free fatty acid having an acyl chain length of 8 carbons, of 10 carbons, of 12 carbons, of 14 carbons, of 16 carbons, of 18 carbons, of 20 carbons, of 22 carbons, and/or of 24 carbons. Further additionally or alternately, the genetically engineered microorganisms can produce at least one free fatty acid having an acyl chain length from 8 to 18 carbons, for example from 12 to 16 carbons.

Typically, acyl-ACP thioesterases are active to some degree on acyl-ACP substrates having a plurality of different acyl chain lengths, but can have higher activity on (e.g., have a substrate preference for) one or more acyl-ACP substrates having particular acyl chain lengths than on other chain length substrates. For example, an acyl-ACP thioesterase may have a substrate preference for one or more of acyl-ACP substrates having acyl chain lengths of 8, 10, 12, 14, 16, 18, 20, 22, and/or 24 carbons. Additionally or alternately, the acyl-ACP thioesterase can hydrolyze one or more acyl-ACP substrates having an acyl chain length from 8 to 18 carbons, for example from 12 to 16 carbons. Further additionally or alternately, an acyl-ACP thioesterases of the present invention can, in some embodiments, have its highest level of activity on an acyl-ACP substrate having an acyl chain length of 12, 14, and/or 16 carbons.

In some embodiments, the microorganism expressing a prokaryotic acyl-ACP thioesterase can produce predominantly free fatty acids having acyl chain lengths of 12, 14, and/or 16 carbons and/or fatty acid derivatives having a total carbon number of 12, 14, 16, 24, 26, 28, 30, and/or 32. Additionally or alternately, at least 30 wt %, for example at least 40 wt %, at least 50 wt %, at least 60 wt %, at least 70 wt %, at least 80 wt %, at least 90 wt %, or at least 95 wt %, of the free fatty acids produced by a genetically engineered microorganism as disclosed herein can be fatty acids having acyl chain lengths of 12, 14, and/or 16 carbons and/or fatty acid derivatives having a total carbon number of 12, 14, 16, 24, 26, 28, 30, and/or 32. One or more free fatty acids produced by the genetically engineered microorganism may be saturated or may have one or more double bonds.

In some embodiments, the genetically engineered microorganism expressing a prokaryotic acyl-ACP thioesterase can produce free fatty acids and/or derivatives of more than one acyl chain length, for example, any combination of two or more of fatty acids having chain lengths of 8, 10, 12, 14, 16, 18, 20, 22, and/or 24 carbons (for example, predominantly fatty acids having acyl chain lengths of 12, 14, and/or 16 carbons). In one such embodiment, at least 50 wt %, for example at least 60 wt %, at least 70 wt %, at least 80 wt %, at least 90 wt %, or at least 95 wt %, of the free fatty acids and/or derivatives produced by a genetically engineered microorganism as disclosed herein can have acyl chain lengths of 12, 14, and 16 carbons, of 12 and 14 carbons, of 12 and 16 carbons, or of 14 and 16 carbons.

Alternatively or in addition, the genetically engineered microorganism can include a recombinant nucleic acid molecule encoding a prokaryotic acyl-ACP thioesterase having an amino acid sequence that has at least 70% identity, for example at least 75%, at least 80%, at least 85%, at least 90%, or at least 95% identity, with SEQ ID NO:1 or SEQ ID NO:2, and the microorganism (e.g., including a prokaryotic thioesterase and/or a nucleic acid molecule that encodes an acyl-ACP thioesterase) can produce a fatty acid having an acyl chain length of 12, 14, and/or 16 carbons (optionally with at least 50 wt % of the fatty acids produced having an acyl chain length from 12 to 16 carbons) and/or a fatty acid derivative having a total number of carbons from 7 to 36 (for example from 7 to 32; from 11 to 36; from 11 to 30; and/or of 7, 8, 9, 10, 11, 12, 13, 14, 15, 16, 17, 18, 20, 22, 24, 26, 28, 30, 32, 34, and/or 36 carbons).

In some embodiments, the genetically engineered photosynthetic microorganism that includes an acyl-ACP thioesterase can produce a fatty aldehyde, fatty alcohol, and/or a wax ester, and can optionally include one or more recombinant nucleic acid molecules encoding a acyl-CoA reductase, carboxylic acid reductase, acyl-ACP reductase, a fatty aldehyde reductase, a wax synthase, or a combination thereof. Wax esters include an acyl chain (A chain) on the carbonyl side of the ester bond and an ester chain (B chain) connected to the oxygen of the ester bond, one or both of which can be derived from a fatty acid, e.g., generated by a thioesterase such as the prokaryotic acyl-ACP thioesterase. Wax esters can have a total number of carbons (an A+B "chain length"), for example, from 10 to 36 carbons, for example from 16 to 36 carbons, from 16 to 32 carbons, or from 24 to 32 carbons.

Additionally or alternately, the genetically engineered photosynthetic microorganism that includes an acyl-ACP thioesterase can produce an alkane and/or alkene and can optionally include at least one recombinant nucleic acid molecule encoding a fatty acid decarboxylase, a fatty aldehyde decarboxylase, an acyl-CoA reductase, carboxylic acid reductase, acyl-ACP reductase, or a combination thereof. Alkanes and/or alkenes produced by and/or derived from a photosynthetic microorganism that includes a recombinant nucleic acid molecule encoding a prokaryotic acyl-ACP thioesterase can, for example, have a chain length of 7, 9, 11, 13, 15, 17, 19, 21, and/or 23 carbons (e.g., one or more odd numbered chain lengths from 7 to 17 carbons, from 7 to 15 carbons, or from 11 to 15 carbons).

Further additionally or alternately, a genetically engineered photosynthetic microorganism that can produce a fatty alcohol, fatty aldehyde, wax ester, alkane, or alkene may optionally include a nucleic acid molecule encoding an acyl-CoA synthetase.

The nucleic acid molecule encoding the prokaryotic acyl-ACP thioesterase can advantageously be stably integrated into the chromosome of the host microorganism, in an autonomously replicating episome, in an expression construct, or a combination thereof. Additionally or alternately, the genetically engineered microorganisms can be transformed with exogenous genes from prokaryotes by the introduction of appropriate nucleic acid expression constructs that can include, in addition to the gene of interest, gene expression sequences and optionally sequences that can mediate recombination into the host chromosome.

Expression constructs can be introduced into prokaryotic and eukaryotic cells via conventional transformation or transfection techniques. The terms "transformation" and "transfection", conjugation and transduction, as used in the present context, are intended to comprise a multiplicity of methods known in the art for the introduction of foreign nucleic acid (for example DNA) into a host cell, including, but not limited to, calcium phosphate or calcium chloride coprecipitation, DEAE-dextran-mediated transfection, lipofection, natural competence, chemically mediated transfer, electroporation, and/or particle bombardment. Suitable methods for the transformation or transfection of host cells can be found in Molecular Cloning—A Laboratory Manual (2010), Cold Spring Harbor Laboratory Press, the contents of which are incorporated by reference herein.

For example, algae and photosynthetic bacteria can be transformed by any suitable method, including, as non-limiting examples, natural DNA uptake (Chung et al. (1998) FEMS Microbiol. Lett. 164: 353-361; Frigaard et al. (2004) Methods Mol. Biol. 274: 325-40; Zang et al. (2007) J. Microbiol. 45: 241-245), conjugation, transduction, glass bead transformation (Kindle et al. (1989) J. Cell Biol. 109: 2589-601; Feng et al. (2009) Mol. Biol. Rep. 36: 1433-9; U.S. Pat. No. 5,661,017), silicon carbide whisker transformation (Dunahay et al. (1997) Methods Mol. Biol. (1997) 62: 503-9), biolistics (Dawson et al. (1997) Curr. Microbiol. 35: 356-62; Hallmann et al. (1997) 94: 7469-7474; Jakobiak et al. (2004) Protist 155:381-93; Tan et al. 2005) J. Microbiol. 43: 361-365; Steinbrenner et al. (2006) Appl Environ. Microbiol. 72: 7477-7484; Kroth (2007) Methods Mol. Biol. 390: 257-267; U.S. Pat. No. 5,661,017), electroporation (Kjaerulff et al. (1994) Photosynth. Res. 41: 277-283; Iwai et al. (2004) Plant Cell Physiol. 45: 171-5; Ravindran et al. (2006) J. Microbiol. Methods 66: 174-6; Sun et al. 2006. Gene 377: 1340-649; Wang et al. (2007) Appl. Microbiol. Biotechnol. 76: 651-657; Chaurasia et al. (2008) J. Microbiol. Methods 73: 133-141; Ludwig et al. (2008) Appl. Microbiol. Biotechnol. 78: 729-35), laser-mediated transformation, or incubation with DNA in the presence of or after pre-treatment with any of poly (amidoamine) dendrimers (Pasupathy et al. 2008. Biotechnol. J. 3: 1078-82), polyethylene glycol (Ohnuma et al. (2008) Plant Cell Physiol. 49: 117-120), cationic lipids (Murakawa et al. (2008) J. Biosci. Bioeng. 105: 77-80), dextran, calcium phosphate, or calcium chloride (Mendez-Alvarez et al. (1994) J. Bacteriol. 176: 7395-7397), optionally after treatment of the cells with cell wall-degrading enzymes (Perrone et al. (1998) Mol. Biol. Cell 9: 3351-3365). *Agrobacterium*-mediated transformation also can be performed on algal cells, for example after removing or wounding the algal cell wall (e.g., International Publication No. WO 2000/62601; Kumar et al. (2004) Plant Sci. 166: 731-738). Biolistic methods are useful for transformation of the chloroplasts of plant and eukaryotic algal species (see, for example, Ramesh et al. (2004) Methods Mol. Biol. 274: 355-307; Doestch et al. 2001. Curr. Genet. 39: 49-60; U.S. Pat. No. 7,294,506; and International Publication Nos. WO 2003/091413, WO 2005/005643, and WO 2007/133558 (each of which cited reference is incorporated by reference in its entirety).

For optimal expression of a recombinant protein, in many instances it can be beneficial to employ coding sequences that can produce mRNA with codons preferentially used by the host cell to be transformed. Thus, for an enhanced expression of transgenes, the codon usage of the transgene can be matched with the specific codon bias of the organism in which the transgene is being expressed. For example, methods of recoding genes for expression in microalgae are described in U.S. Pat. No. 7,135,290, the content of which is incorporated by reference. All or a subset of the codons of a gene can be changed to incorporate a preferred codon used by the host organism. Additional information for codon optimization is available, e.g., at the codon usage database of Genbank.

In some embodiments, the thioesterase-encoding nucleotide sequence in microorganisms transformed with an isolated nucleic acid molecule including a recombinant nucleic acid sequence encoding a prokaryotic acyl-ACP thioesterase can be operably linked to one or more expression control elements and can optionally be codon-optimized for expression in the microorganism.

Alternatively or in addition, the exogenous nucleic acid molecule as disclosed herein can be cloned into an expression vector for transformation into a microalga or a photosynthetic bacterium. The vector can include sequences that promote expression of the transgene of interest (e.g., an exogenous prokaryotic acyl-ACP thioesterase gene) such as a heterologous promoter, and may optionally include, for expression in eukaryotic cells, without limitation, an intron sequence, a sequence having a polyadenylation signal, etc. Alternately, if the vector does not contain a promoter in operable linkage with the gene of interest, the gene can be transformed into the cells such that it becomes operably linked to an endogenous promoter by homologous recombination or vector integration.

Vectors designed for expression of a gene in microalgae can include a promoter active in microalgae operably linked to the exogenous gene being introduced. A variety of gene promoters and terminators that function in microalgae can be utilized in expression vectors, including, but not limited to, promoters and terminators from prokaryotes or eukaryotes, such as, but not limited to, *Chlamydomonas* and other algae (see, for example, Plant Cell Physiol 49: 625-632, 2008), promoters and terminators from viruses, and synthetic promoters and terminators.

For transformation of diatoms, a variety of gene promoters that function in diatoms can be utilized in these expression vectors, including, but not limited to: promoters from *Thalassiosira* and other heterokont algae, promoters from viruses, and synthetic promoters. Promoters from *Thalassiosira pseudonana* that would be suitable for use in expression vectors include, without limitation, an alpha-tubulin promoter, a beta-tubulin promoter, and an actin promoter. Promoters from *Phaeodactylum tricornutum* that would be suitable for use in expression vectors include, without limitation, an alpha-tubulin promoter, a beta-tubulin promoter, and an actin promoter. The terminators associated with these genes, other diatom genes, or particular heterologous genes can be used to stop transcription and provide the appropriate signal for polyadenylation.

If desired, in order to express the exogenous nucleic acid molecule, such as, prokaryotic acyl-ACP thioesterase, in the plastid, where the fatty acid biosynthesis occurs in microalgae, a nucleotide sequence encoding a chloroplast transit peptide can be added to the N-terminus of the exogenous nucleic acid molecule. Alternately, the exogenous nucleic acid molecule encoding a prokaryotic acyl-ACP thioesterase can be introduced directly into the plastid chromosome of microalgae without disrupting photosynthetic capability of the plastid. Methods for plastid transformation are well known for introducing a nucleic acid molecule into a plant cell chloroplast (see, for example, International Publication Nos. WO 2010/019813 and WO 95/16783; U.S. Pat. Nos. 5,451,513, 5,545,817, and 5,545,818; and McBride et al., Proc. Natl. Acad. Sci. USA 91:7301-7305 (1994), each of which are incorporated by reference herein).

In some instances, it can be advantageous to express an enzyme, such as, but not limited to, a prokaryotic acyl-ACP thioesterase, at a certain point during the growth of the genetically engineered host organism to minimize any deleterious effects on the growth of that organism and/or to maximize production of the fatty acid product of interest. In these instances, one or more exogenous nucleic acid molecules encoding a prokaryotic acyl-ACP thioesterase introduced into the genetically engineered organism can be operably linked to an inducible promoter. The promoter can be, for example, without limitation, a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter; see U.S. Pat. No. 6,379,945), a metallothionien promoter (U.S. Pat. No. 6,410,828), and/or a pathogenesis-related (PR) promoter that can be responsive to a chemical such as, for example, salicylic acid, ethylene, thiamine, or BTH (U.S. Pat. No. 5,689,044). An inducible promoter can be responsive to light or dark (U.S. Pat. Nos. 5,750,385 and 5,639,952), temperature (U.S. Pat. No. 5,447,858; Abe et al., Plant Cell Physiol. 49: 625-632 (2008); Shroda et al. Plant J. 21: 121-131 (2000)), or the like, or combinations thereof. The foregoing list is meant to be exemplary and not limiting. The promoter sequences can be from any organism, provided that they are functional in the host organism. Inducible promoters, as used in the constructs of the present invention, can use one or more portions/domains of the aforementioned promoters and/or other inducible promoters fused to at least a portion of a different promoter that operates in the host organism to confer inducibility on a promoter that operates in the host species.

For example, for transformation of cyanobacteria, a variety of promoters that function in cyanobacteria can be utilized, including, but not limited to, the lac, tac and trc promoters and derivatives that are inducible by the addition of isopropyl β-D-1-thiogalactopyranoside (IPTG), promoters that are naturally associated with transposon- or bacterial chromosome-borne antibiotic resistance genes (neomycin phosphotransferase, chloramphenicol acetyltransferase, spectinomycin adenyltransferase, etc.), promoters associated with various heterologous bacterial and native cyanobacterial genes, promoters from viruses and phages, and synthetic promoters. One embodiment of such promoter includes an IPTG-inducible trcY promoter (SEQ ID NO:9). Promoters isolated from cyanobacteria that can be used can include, without limitation, secA (secretion; controlled by the redox state of the cell), rbc (Rubisco operon), psaAB (PS I reaction center proteins; light regulated), and psbA (Dl protein of PSII; light-inducible).

Likewise, a wide variety of transcriptional terminators can be used for expression vector construction. Examples of possible terminators include, but are not limited to, psbA, psaAB, rbc, secA, and T7 coat protein.

Transformation vectors can optionally also include a selectable marker, such as, but not limited to, a drug resistance gene, an herbicide resistance gene, a metabolic enzyme or factor required for survival of the host (for example, an auxotrophic marker), and the like, as well as combinations thereof. Transformed cells can optionally be selected based upon the ability to grow in the presence of the selectable marker under conditions in which cells lacking the resistance cassette or auxotrophic marker would not grow. Alternately, a non-selectable marker may be present on a vector, such as a gene encoding a fluorescent protein or enzyme that generates a detectable reaction product.

Expression vectors can be introduced into the microorganisms by standard methods, including, but not limited to, natural DNA uptake, conjugation, electroporation, particle bombardment and abrasion with glass beads, SiC fibers, or other particles. The vectors can be, for example, (1) targeted for integration into the host chromosome by including flanking sequences that enable homologous recombination into the chromosome, (2) targeted for integration into endogenous plasmids by including flanking sequences that enable homologous recombination into the endogenous plasmids, and/or (3) designed such that the expression vectors replicate within the chosen host.

The genetically engineered microorganism can further comprise one or more additional recombinant nucleic acid molecules that may enhance production of fatty acids and/or fatty acid derivatives, such as, for example, a gene encoding an acetyl-CoA carboxylase or a subunit thereof and/or a gene encoding a β-ketoacyl synthase (KAS), such as a KAS III, KAS II, or KAS I enzyme. Additionally or alternately, the microorganism can have attenuated expression of a gene encoding acyl-ACP synthase, acyl-CoA synthase, acyl-CoA dehydrogenase, glycerol-3-phosphate dehydrogenase, acetaldehyde-CoA dehydrogenase, pyruvate dehydrogenase, acetate kinase, or the like, or a combination thereof.

In some embodiments, the culture medium does not include a reduced carbon compound for supplying energy to the genetically engineered photosynthetic microorganism, and yet the culture comprising the microorganism can produce at least twice the amount of a free fatty acid and/or fatty acid derivative, compared to a culture of the same microorganism that does not include a recombinant nucleic acid encoding the prokaryotic thioesterase, and/or the culture medium that includes the transformed microorganism that includes an acyl-ACP thioesterase can include at least 5 mg per liter, for example at least 10 mg per liter, at least 20 mg per liter, at least 30 mg per liter, at least 40 mg per liter, or at least 50 mg per liter, of free fatty acids and/or fatty acid derivatives produced by the microorganism.

The nucleic acid molecule encoding the prokaryotic acyl-ACP thioesterase can be any as described hereinabove, for example, a member of Pfam family PF01643 and/or, when queried against the Pfam database, is a match with PF01643 with a bit score greater than the gathering threshold value and/or with an e value of less than 0.01. As mentioned herein, the nucleic acid molecule can be operably linked to a promoter active in the photosynthetic microorganism and optionally one or more additional nucleic acid regulatory sequences, such as, for example, a transcriptional terminator sequence. Additionally or alternately, the nucleic acid molecule can be present on a self-replicating plasmid introduced into the photosynthetic microorganism, and/or can be integrated into the genome of the photosynthetic microorganism.

In some embodiments, the fatty acids and/or fatty acid derivatives can be present in the media, for example, as precipitates in or on, at or near the surface of the media, associated with the media vessel as droplets, including suspended droplets (e.g., an emulsion), as a relatively immiscible layer floating on top of the aqueous culture medium, as a "scum", film, gel, semi-solid, colloid, fine particulate, particulate, solid, or aggregate that may be dispersed, suspended, or entrained within the culture medium, associated with the cells of the photosynthetic microorganism, phase separated in some other fashion, or a combination thereof.

In preferred embodiments, at least one free fatty acid produced by a culture as disclosed herein can have an acyl chain length from 8 to 24 carbons, for example from 8 to 18 carbons, from 12 to 16 carbons, or of 8, 10, 12, 14, 16, 18, 20, 22, and/or 24 carbons. In embodiments where at least one fatty acid derivative (such as one or more fatty alcohols, fatty aldehydes, wax esters, alkanes, and alkenes) are produced by a culture as disclosed herein, the at least one fatty acid derivative can have a total number of carbons from 7 to 36, for example from 11 to 34, from 12 to 32, or of 7, 8, 9, 10, 11, 12, 13, 14, 15, 16, 17, 18, 19, 20, 21, 22, 23, 24, 26, 28, 30, 32, 34, and/or 36.

Advantageously, the culture medium can be any suitable for growth of the photosynthetic microorganism. In one embodiment, the culture can include a source of reduced carbon, such as, for example, one or more sugars or organic acids that can be used by the microorganism for growth, such that the microorganism can grow heterotrophically or mixotrophically. Additionally or alternately, the culture medium does not include a substantial amount of a reduced carbon compound that can be used for the organism as an energy source and/or includes a source of inorganic carbon, such as $CO_2$ or bicarbonate.

II. Methods of Producing Free Fatty Acids and/or Derivatives

An aspect of the present invention relates to a method for producing a free fatty acid and/or derivative in a culture, the method comprising culturing photosynthetic microorganisms that include at least one recombinant nucleic acid sequence encoding a prokaryotic acyl-ACP thioesterase in growth media under conditions that allow expression of the prokaryotic acyl-ACP thioesterase. Expression of the prokaryotic acyl-ACP thioesterase in the photosynthetic microorganism can result in production of at least one free fatty acid and/or fatty acid derivative.

In one embodiment, the culture that includes the photosynthetic microorganism that expresses a prokaryotic acyl-ACP thioesterase can produce at least twice the amount of the fatty acid and/or derivative, compared to a culture that is identical in all respects except that the photosynthetic microorganism does not include a recombinant nucleic acid sequence encoding a prokaryotic acyl-ACP thioesterase. For example, the photosynthetic microorganism that includes the recombinant nucleic acid molecule encoding the prokaryotic acyl-ACP thioesterase can produce (and optionally but preferably release and/or secrete) at least 5 mg per liter, for example at least 10 mg per liter, at least 20 mg per liter, at least 30 mg per liter, at least 40 mg per liter, or at least 50 mg per liter, of free fatty acids and/or fatty acid derivatives.

The method can further comprise isolating/removing the free fatty acid and/or derivative from the culture, e.g., from the cells, the growth media, or the whole culture. For example, the isolation can be by organic extraction of whole or lysed cells, removal of free fatty acids or fatty acid derivatives as precipitates or from the upper layer of the culture media ("skimming"), through the use of particulate adsorbents, bubbles, or matrices that bind the fatty acids and/or derivatives, or the like, or any combination thereof.

The genetically engineered photosynthetic microorganism can be any as described herein that includes a recombinant nucleic acid molecule encoding a prokaryotic acyl-ACP thioesterase, whose expression can result in production of free fatty acids and/or fatty acid derivatives. The acyl-ACP thioesterase can be expressed for at least a portion of the time during which the photosynthetic microorganism is cultured and/or upon administering an inducer to the culture. Non-limiting examples of the inducer include lactose or a lactose analogue, such as isopropyl β-D-1-thiogalactopyranoside, and light, which can be provided as sunlight or artificial light, such as, for example, fluorescent light.

Additionally or alternately, the genetically engineered photosynthetic microorganism can be grown phototrophically, in which case the growth media typically does not include a substantial amount of (e.g., includes none of) a reduced carbon source. When growing phototrophically, the microorganism uses light as its energy source, and an inorganic carbon source, such as $CO_2$ or bicarbonate, is used for synthesis of biomolecules by the microorganism. Alternately, an organic carbon molecule or compound can be provided in the culture medium of a microorganism grown phototrophically, but it either cannot be taken up or metabolized by the cell for energy or is not present in an amount effective to provide energy sufficient for the growth of the cell culture.

In many embodiments, the culture can include an inorganic carbon source, including, but not limited to, bicarbonate, calcium carbonate, and/or $CO_2$, present in air, or provided in enriched form with respect to ambient $CO_2$, for example, as 5 vol % $CO_2$ in air. Additionally or alternately, the photosynthetic microorganisms can be exposed to light for at least a portion of the culturing period. Artificial light sources can be used as the sole light source or to enhance or extend natural light.

"Culturing" refers to the intentional fostering of growth (increases in cell size, cellular contents, and/or cellular activity) and/or propagation (increases in cell numbers, e.g., via mitosis) of one or more cells by use of selected and/or controlled conditions. The combination of both growth and propagation may be termed "proliferation." Examples of selected and/or controlled conditions can include the use of a defined medium (with known characteristics, such as pH, ionic strength, and carbon source), specified temperature, oxygen tension, carbon dioxide levels, and growth in a bioreactor, inter alia.

The photosynthetic microorganisms, such as, microalgae or cyanobacteria, can be cultured phototrophically, in the absence of a substantial amount of a fixed carbon source, or mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid form (e.g., acetate, citrate, succinate), and/or glycerol. The photosynthetic microorganism, alternately, can be cultured mixotrophically, such that the organism is grown in the presence of light for at least a part of the day, and also provided with one or more sources of reduced carbon. Cells can alternately be grown heterotrophically, where a reduced carbon source is provided in the media for energy and biochemical synthesis. A photosynthetic organism can be grown mixotrophically for a period of time, followed by a period of phototrophic growth, or vice versa.

A variety of media for phototrophic and/or mixotrophic growth of algae and cyanobacteria are known in the art, and media can be optimized to enhance growth or production of fatty acid products for a particular species.

Microorganisms that may be useful in accordance with the methods of the present invention can be found in various locations and environments throughout the world. As a consequence of their isolation from other species and their resulting evolutionary divergence, the particular growth medium for optimal growth and generation of lipid and/or hydrocarbon constituents can vary. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of strains of microorganisms. For example, various fresh water and salt water media can include those described in Barsanti, L. amd Gualtieri, P. (2005) Algae: Anatomy, Biochemistry, and Biotechnology, CRC Press, Taylor & Francis Group, Boca Raton, Fla., USA, which is incorporated herein by reference for media and methods for culturing algae. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (cca-p.ac.uk/media/pdfrecipes); and Katedra Botaniky (/bot-any.natur.cuni.cz/algo/caup-media.html).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Table 2), or a modified medium such as ATCC Medium 854 (BG-11 modified to contain vitamin B12) or ATCC Medium 617 (BG-11 modified for marine cyanobacteria, containing additional NaCl and vitamin B12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation.

In further embodiments, by using the excess amount of metal (e.g., calcium) in the medium, at least a portion of the fatty acid(s) can be sequestered as soap precipitates, which may result in decreasing the toxic effects of free fatty acid(s). Addition of metal (e.g., calcium) in the medium can additionally or alternately increase the tolerance of microorganism in media with a relatively high concentration of free fatty acids. Additionally or alternately, fatty acid-producing strains can advantageously be more robust with excess metal (e.g., calcium) content. Although the excess component is described herein as a metal, it is contemplated that the component can more generally be described as a carboxylate counterion source, for example an soap-forming counterion source, a metal ion source (noted as "metal" herein), a multivalent (i.e., having a valence of +2 or higher) counterion source, a divalent counterion source, or some combination. Other details regarding this metal/carboxylate counterion source are described in the co-pending, commonly-assigned patent application, entitled "Culturing a Microorganism in a Medium with an Elevated Level of a Carboxylate Counterion Source" and filed on the same day herewith.

For production of fatty acids and/or fatty acid derivatives, photosynthetic microorganisms can be grown indoors (e.g., in photobioreactors, in shake flasks, test tubes, vials, microtiter dishes, petri dishes, or the like) or outdoors (e.g., in ponds, canals, trenches, raceways, channels, or the like). Additionally or alternately, a source of inorganic carbon (such as, but not limited to, $CO_2$), including, but not limited to, air, $CO_2$ enriched air, or flue gas, can be supplied to the photosynthetic microorganisms.

Additionally or alternately, the present invention can include one or more of the following embodiments.

Embodiment 1

A photosynthetic microorganism (e.g., a microalga or a cyanobacterium) comprising a recombinant nucleic acid molecule encoding a prokaryotic acyl-acyl carrier protein (acyl-ACP) thioesterase, wherein the photosynthetic microorganism (e.g., through expression of the prokaryotic acyl-ACP thioesterase) results in production of at least one free fatty acid and/or fatty acid derivative.

Embodiment 2

The photosynthetic microorganism according to embodiment 1, wherein the at least one fatty acid derivative comprises at least one fatty aldehyde, at least one fatty alcohol, at least one wax ester, at least one alkane, at least one alkene, or a combination thereof, and/or has a total number of carbons from 7 to 36, for example from 11 to 34 or from 11 to 32.

Embodiment 4

The photosynthetic microorganism according to any one of the previous embodiments, wherein the photosynthetic microorganism is capable of producing at least one fatty acid having an acyl chain length from 8 to 24 carbons or from 8 to 18 carbons.

Embodiment 5

The photosynthetic microorganism according to any one of the previous embodiments, wherein at least 30 wt % of the free fatty acids produced by the photosynthetic microorganism are free fatty acids having an acyl chain length of 12 carbons, 14 carbons, 16 carbons, or any mixture thereof.

Embodiment 6

The photosynthetic microorganism according to any one of the previous embodiments, wherein the prokaryotic acyl-ACP thioesterase has at least 70% amino acid sequence identity, for example at least 75%, at least 80%, at least 85%, at least 90%, at least 95%, at least 96%, at least 97%, at least 98%, at least 99%, or about 100% sequence identity, to SEQ ID NO:1 or SEQ ID NO:2.

Embodiment 7

The photosynthetic microorganism according to any one of the previous embodiments, wherein the nucleic acid molecule encoding the prokaryotic acyl-ACP thioesterase comprises nucleotide sequence SEQ ID NO:3 or SEQ ID NO:4.

Embodiment 8

The photosynthetic microorganism according to any one of the previous embodiments, wherein the nucleic acid molecule encoding the prokaryotic acyl-ACP thioesterase is stably integrated into a chromosome of the photosynthetic microorganism and/or is in an expression construct.

Embodiment 9

The photosynthetic microorganism according to embodiment 8, wherein the expression construct comprises a promoter operably linked to the nucleic acid molecule encoding the prokaryotic acyl-ACP thioesterase, and optionally wherein the promoter is functional in the photosynthetic microorganism.

Embodiment 10

The photosynthetic microorganism according to any one of the previous embodiments, wherein the photosynthetic microorganism further comprises at least one additional nucleic acid molecule encoding at least one additional polypeptide such as acetyl-CoA carboxylase or β-ketoacyl synthase (KAS), wherein expression of the additional nucleic acid molecule in the photosynthetic microorganism enhances production of a free fatty acid and/or fatty acid derivative.

Embodiment 11

The photosynthetic microorganism according to any one of the previous embodiments, wherein the photosynthetic microorganism has attenuated expression of at least one gene encoding a protein comprising acyl-acyl carrier protein (ACP) synthase, acyl-CoA dehydrogenase, glycerol-3-phosphate dehydrogenase, acetaldehyde-CoA dehydrogenase, pyruvate dehydrogenase, acetate kinase, and combinations thereof.

Embodiment 12

A method for producing a free fatty acid and/or fatty acid derivative in a culture, the method comprising culturing a photosynthetic microorganism in growth media, wherein the photosynthetic microorganism comprises at least one nucleic acid molecule encoding an prokaryotic acyl-ACP thioesterase according to any one of the previous embodiments; and wherein the photosynthetic microorganism is grown under a condition that allows expression of the prokaryotic acyl-ACP thioesterase in the photosynthetic microorganism during a culturing period.

Embodiment 13

The method according to embodiment 12, wherein at least a portion of the free fatty acid and/or fatty acid derivative is secreted into the growth media.

Embodiment 14

The method according to embodiment 12 or embodiment 13, wherein the growth media does not include a substantial amount of a reduced carbon source, wherein the culture is provided with at least one source of inorganic carbon, and/or wherein the culture is exposed to light for at least a portion of the culturing period.

Embodiment 15

The method according to any one of embodiments 12-14, wherein the method further comprises isolating at least one free fatty acid and/or derivative from the photosynthetic microorganism, the growth media, or the whole culture.

Embodiment 16

The method according to embodiment 12, wherein the photosynthetic microorganism comprises at least one nucleic acid molecule encoding an prokaryotic acyl-ACP thioesterase having at least 70% amino acid sequence identity to SEQ ID NO:1, wherein the photosynthetic microorganism produces at least one free fatty acids or fatty acid derivative, wherein at least 50%, at least 60%, or at least 65% of the free fatty acids or fatty acid derivatives produced are C12, C14, and/or C16 free fatty acids or fatty acid derivatives.

Embodiment 17

The method according to embodiment 12, wherein the photosynthetic microorganism comprises at least one nucleic acid molecule encoding an prokaryotic acyl-ACP thioesterase having at least 70% amino acid sequence identity to SEQ ID NO:2, wherein the photosynthetic microorganism produces at least one free fatty acids or fatty acid derivative, wherein at least 50%, of the free fatty acids or fatty acid derivatives produced are C12, C14, and/or C16 free fatty acids or fatty acid derivatives.

Embodiment 17

The method according to embodiment 12, wherein the photosynthetic microorganism comprises at least one nucleic acid molecule encoding an prokaryotic acyl-ACP thioesterase having at least 70% amino acid sequence identity to SEQ ID NO:2, wherein the photosynthetic microorganism produces at least one free fatty acids or fatty acid derivative, wherein at least 50%, of the free fatty acids or fatty acid derivatives produced are C14, C16, and/or C18 free fatty acids or fatty acid derivatives.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference in their entireties.

Nucleic acid and amino acid sequences identified by Accession Numbers or GenInfo Identifiers are also incorporated by reference herein. Accession numbers are unique identifiers for a sequence record publicly available at the National Center for Biotechnology Information internet site maintained by the United States National Institutes of Health, which can be accessed at ncbi.nlm.nih.gov. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appeared in a specific Genbank record. Searching and obtaining nucleic acid or gene sequences or protein sequences based on Accession numbers and GI numbers is well known in the arts of cell biology, biochemistry, molecular biology, and molecular genetics.

It must also be noted that as used herein and in the appended claims, the singular forms "a," "an," and "the" include plural referents unless the context clearly dictates otherwise. All technical and scientific terms used herein have the same meaning. The use of "or" in a listing of two or more items indicates that any combination of the items is contemplated, for example, "A or B" indicates that A alone, B alone, or both A and B are intended.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification of Prokaryotic Acyl-ACP Thioesterases

In order to identify prokaryotic acyl-ACP thioesterases that can produce fatty acids and be expressed in microorganisms, such as microalgae and cyanobacteria, prokaryotic sequence databases were searched using the BLASTP tool (National Center for Biotechnology Information (NCBI) and using sequences of known bacterial acyl-CoA thioesterases. A phylogenetic tree then was constructed using Vector NTI® software (Invitrogen, Carlsbad, Calif.), based on the retrieved sequences of acyl-CoA thioesterases, non-ribosomal peptide synthetase (NRPS) thioesterase modules, polyketide thioesterase modules, and 4-hydroxybenzoyl-CoA thioesterases. Known plant acyl-ACP thioesterases also were added to the tree. Analysis of the phylogenetic tree suggested that the prokaryotic acyl-ACP thioesterases form a clade together with plant acyl-ACP thioesterase, distinct from the bacterial acyl-CoA thioesterases. Among the identified prokaryotic acyl-ACP thioesterases, two examples of the clade were selected for further characterization, i.e., the polypeptide EMRE031 (YP_001303423 GI:150008680; SEQ ID NO:1) from *Parabacteroides distasonis* and the polypeptide EMRE032 (YP_001039461 GI:125975551; SEQ ID NO:2) from *Clostridium thermocellum*.

Example 2

Molecular Cloning of Prokaryotic Acvl-ACP Thioesterases

The nucleotide sequences encoding the *Parabacteroides distasonis* EMRE 031 polypeptide (nucleotides 2447794 to 2447069 of Genbank Accession CP000140) and the *Clostridium thermocellum* EMRE032 polypeptide (nucleotides 3613743 to 3612982 of Genbank Accession CP000568) were obtained from National Center for Biological Information (NCBI). These sequences then were used to design nucleotide sequences consistent with the codon usage of *Synechocystis* sp. PCC6803 (at kazusa.or.jp/codon/cgi-bin/showcodon.cgi?species=1148). Genes encoding the *Parabacteroides distasonis* thioesterase EMRE031, codon-optimized for expression in *Synechocystis* (SEQ ID NO:3), and the *Clostridium thermocellum* acyl-ACP thioesterase EMRE032, codon-optimized for expression in *Synechocystis* (SEQ ID NO:4), were synthesized by GENEWIZ (La Jolla, Calif.).

In order to express the *Parabacteroides distasonis* acyl-ACP thioesterase EMRE031 (SEQ ID NO:1) and the *Clostridium thermocellum* EMRE032 (SEQ ID NO:2) in *E. coli* and *Synechocystis*, the inserts (i.e., the *Parabacteroides distasonis* thioesterase gene (SEQ ID NO:3) and the *Clostridium thermocellum* thioesterase gene (SEQ ID NO:4)) were subcloned into a pYC expression vector. The pYC vector was derived from a pUC19 backbone, which includes a bacterial origin of replication for maintenance of the plasmid in *E. coli*. The pYC vector includes the RS2 "up" (5') and RS1 "down" (3') sequences from the *Synechocystis* genome for homologous recombination (Williams et al., 1988, Methods in Enzymology, 167: 766-778). In addition, the expression vector included an omega-Sp cassette providing spectinomycin resistance, and the isopropyl β-D-1-thiogalactopyranoside (IPTG)-inducible trcY promoter (SEQ ID NO:9).

Figure 2:
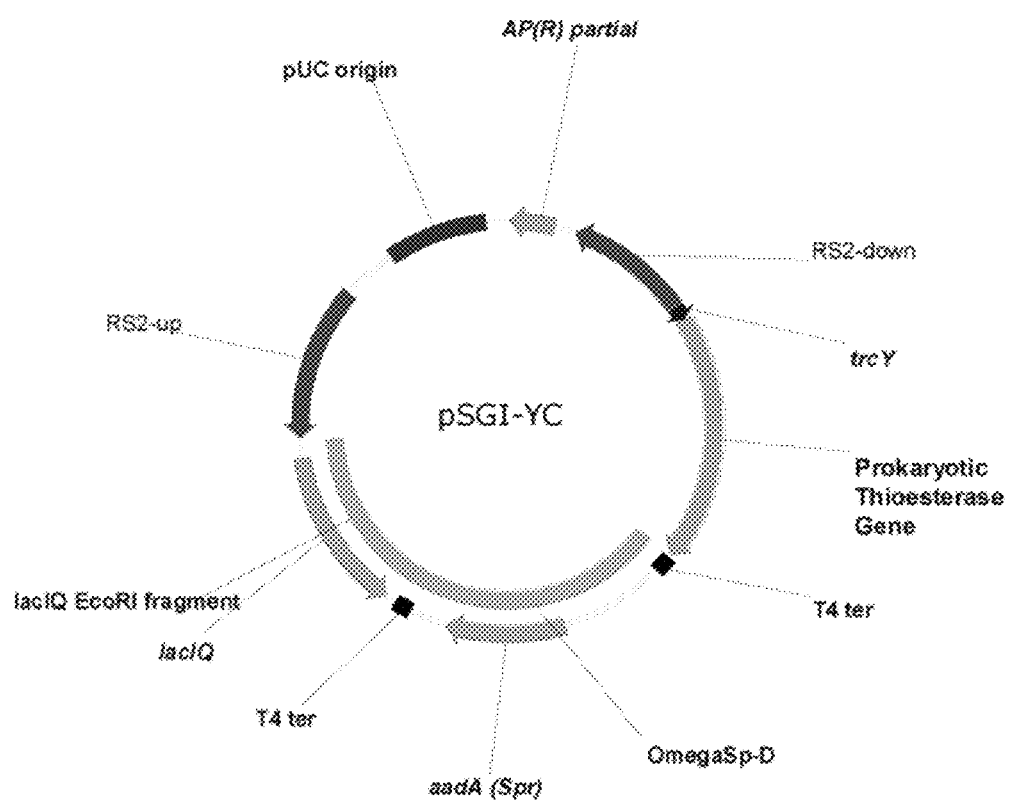
FIG. 2 shows the physical map of the expression vector (pSGI-YC) containing the prokaryotic acyl-ACP thioesterase genes (EMRE031 (SEQ ID NO:3) and EMRE032 (SEQ ID NO:4)) of the invention.

Specifically, in order to create the pYC vector expressing prokaryotic thioesterases, the RS2 sequence (including both the up and down fragments shown in the vector map in FIG. 2) was amplified from *Synechocystis* sp. PCC 6803 genomic DNA using the primers: RS2 (5'-GGGCCCTATTTGCCCG-TATTCTGCCCTATCC-3'; SEQ ID NO:5) and RS2-3 (5'-GGGCCCGACTGCCTTTGGTGGTATTACCGATG-3'; SEQ ID NO:6). Plasmid pUC19 was digested with HindIII and EcoRI to remove the multiple cloning site (MCS), and then treated with T4-DNA polymerase to blunt the ends. The RS2 sequence (comprising RS2 up and RS2 down, 1.8 kb) was ligated then into the pUC19 backbone. The resulting plasmid was named pYC34. The pYC34 plasmid was digested then with BglII, which cut within the RS2 sequence, opening up the integration site. A copy of the omega-Sp cassette (BamHI fragment) was ligated into the BglII site of pYC34 to make pYC36. The pYC36 plasmid was digested with FspI to remove the majority of the Ampicillin resistance gene (Apr), making spectinomycin/streptomycin as the only selectable marker. The constructed plasmid was named pYC37. An EcoRI fragment containing the lacIq gene was inserted into the EcoRI site of pYC37, between the RS2 "up" sequence and the omega Sp cassette to allow for regulation of lac-inducible promoters. The vector further included a TrcY promoter. The TrcY promoter was amplified using the following primers: 4YC-trcY-5 (5'-ACTAGTCCTGAGGCT-GAAATGAGCTGTTGACAATTAATCATC-CGGCTCGTATAATGTGTGGA ATTGTGAG-3'; SEQ ID NO:7) and 4YC-trcY-3 (5'-CCATGGTTTTTTTCCTCCT-TAGTGTGAAATTGTTATCCGCTCACAAT-TCCACACATTATACGA GCCGGAT-3'; SEQ ID NO:8) and inserted into the vector digested with SpeI-XbaI. The plasmid was called pYC45. The sequence of the TrcY promoter is provided as (5'-CTGAAATGAGCTGTTGACAATTAAT-CATCCGGCTCGTATAATGTGTGGAAT-TGTGAGCGGAT AACAATTTCACAC TAAGGAG-GAAAAAAA-3'; SEQ ID NO:9).

For cloning the prokaryotic thioesterase genes into a pYC expression vector for use in *E. coli* and *Synechocystis*, primers were designed to the 5' and 3' ends of each gene, in which the 5' primer had homology to the region of the pYC vector upstream of the NcoI cloning site, and the 3' primer had homology to the region of the pYC vector downstream of the XbaI cloning site, both downstream of the TrcY promoter (SEQ ID NO:9). PCR was performed to generate fragments having 5' and 3' ends homologous to the vector. The primers for cloning the EMRE031 gene were: 5'-AGGAAAAAAAC-CATGATGGAAAAAGTGGGTCTGTTC-3' (SEQ ID NO:10) and 5'-CCTGCAGATATCTAGATTACCGCCAG-GTCACGGCTGCCCGAC-3' (SEQ ID NO:11). The primers for cloning the EMRE032 gene were: 5'-AGGAAAAAAAC-CATGATGCAAAAAAAGCGGTTCAGCAAG-3' (SEQ ID NO:12) and 5'-CCTGCAGATATCTAGATTAGGACT-GAATTTTCTGCCAAATG-3' (SEQ ID NO:13).

The pYC expression vector was digested with NcoI and XbaI and co-transformed with the EMRE031 or EMRE032 PCR fragment into One Shot® Top10 competent cells (Invitrogen, Carlsbad, Calif.) according to the manufacturer's protocol. The competent cells were plated on an agar plate coated with spectinomycin (~50 μg/ml) for antibiotic selection. The resulting colonies were screened further by PCR using the same primers used for generating the EMRE031 and EMRE032 fragments for cloning. The PCR conditions were ~94° C. for ~5 minutes, followed by ~29 cycles of ~30 secs at ~94° C., ~30 secs at ~55° C., and ~90 secs at ~72° C., followed by a final run-off for ~5 min at ~72° C.

The resulting expression constructs had a pUC origin of replication, a prokaryotic thioesterase gene cloned downstream of the TrcY promoter and upstream of the T4 terminator and flanked by the RS1 up and RS1 down sequences; the omega spectinomycin cassette, and the lacIq gene positioned between the RS1 down and RS1 up sequences.

The sequence of the pYC expression construct that includes the EMRE-031 gene is provided as SEQ ID NO:14 and the sequence of the pYC expression construct that includes the EMRE-032 gene is provided as SEQ ID NO:15

Example 3

Expression of Prokaryotic Acyl-ACP Thioesterase in *Escherichia coli*

For the expression of the prokaryotic thioesterase genes (SEQ ID NO:3 and SEQ ID NO:4) in *E. coli*, ~1.2 ml of 2×YT media (~1.6% Bacto-tryptone, ~1% Bacto-yeast extract, ~0.5% NaCl, pH ~7.2) containing ~50 μg/ml spectinomycin and ~1 mM Isopropyl β-D-1-thiogalactopyranoside (IPTG) in a glass tube was inoculated with ~30 microliters of a saturated culture of each bacterial strain and cultured for ~24 hours. About 0.6 mL of the culture was removed for biochemical analysis.

Example 4

Analysis of Fatty Acid Samples from *Escherichia coli*

Free fatty acids were analyzed by gas chromatography (GC) with flame ionization detection (GC-FID). Specifically, ~0.6 mL of the *E. coli* cultures in Example 3 were added to ~2 ml glass gas chromatography vials with PTFE (polytetrafluoroethylene)-lined caps (National Scientific). About fifty microliters of an internal standard set that included the free fatty acids C9:0, C13:0, and C17:0, each at a concentration of ~600 μg/ml, in hexane, were added to the culture sample, followed by ~50 microliters of ~50% H2SO4, ~100 microliters of ~5M NaCl, and ~850 microliters of hexane. The final concentration of each internal standard was ~50 μg/ml. The fatty acids for making the internal standard set were purchased from Fluka or Nu Chek Prep. The cultures were then vortexed on a multi-tube vortexer at ~2,500 rpm for ~30 mins. The vials were finally centrifuged for ~3 mins at ~2500 rpm to provide good separation between organic and aqueous phases. The hexane layers were sampled by a Gerstel MPS2L Autos ampler.

*E. coli* fatty acid samples were analyzed on an Agilent model 7890A gas chromatograph equipped with an FID (flame ionization detector) that included a J&W Scientific DB-FFAP capillary column (~15 m length, ~0.25 mm internal diameter, ~0.25 μm film thickness) coupled to an Agilent 5975C mass spectrophotometer. The GC oven was programmed as follows: ~140° C. for ~0.5 min., then heated at ~20° C./min. to ~230° C. (hold ~5 mins). The injector temperature was kept at ~250° C., and a ~40:1 split ~1 μl injection was used. Helium was used as a carrier gas at a flow rate of ~1.2 ml/min. The analytes were identified by comparison of retention times to individually injected standards. The calibration range for the analytes was ~2 μg/ml to ~200 μg/ml for C8:0-C16:1 fatty acids and ~0.5 μg/ml to ~50 μg/ml for C18:0-C18:2 fatty acids. Spiking and recovery experiments into whole cell culture showed that the extraction method recovered consistently within a range of about 85%-115% of each analyte.

Figure 3:
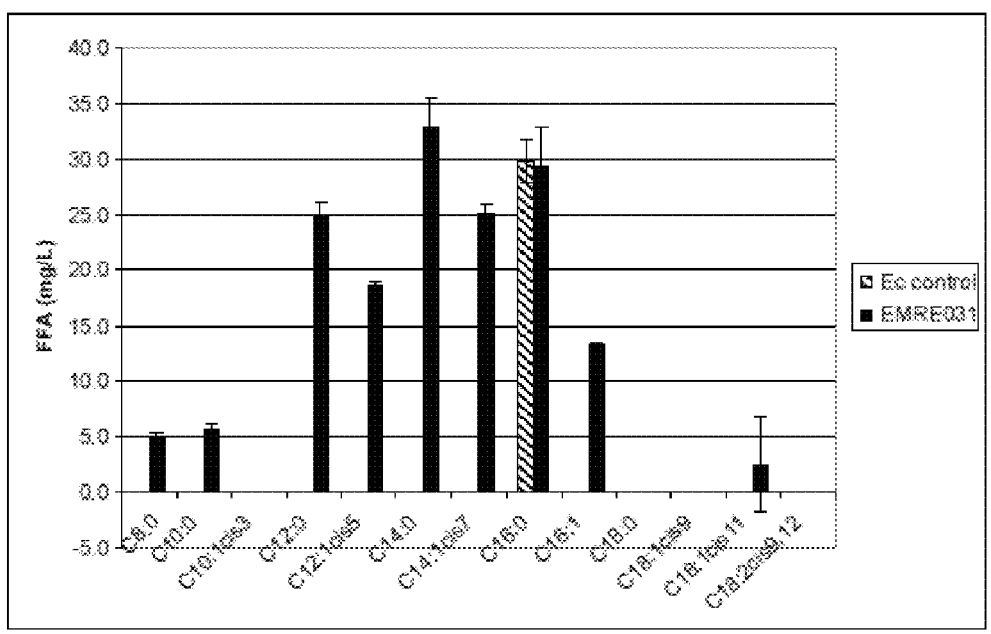
FIG. 3 shows the profile of the free fatty acids (FFA) isolated from the culture of Escherichia coli K19 expressing the EMRE031 gene (SEQ ID NO:3) and the profile of the free fatty acids (FFA) isolated from the culture of a control Escherichia coli K19 strain without the EMRE031 gene (Ec control).
Figure 4:
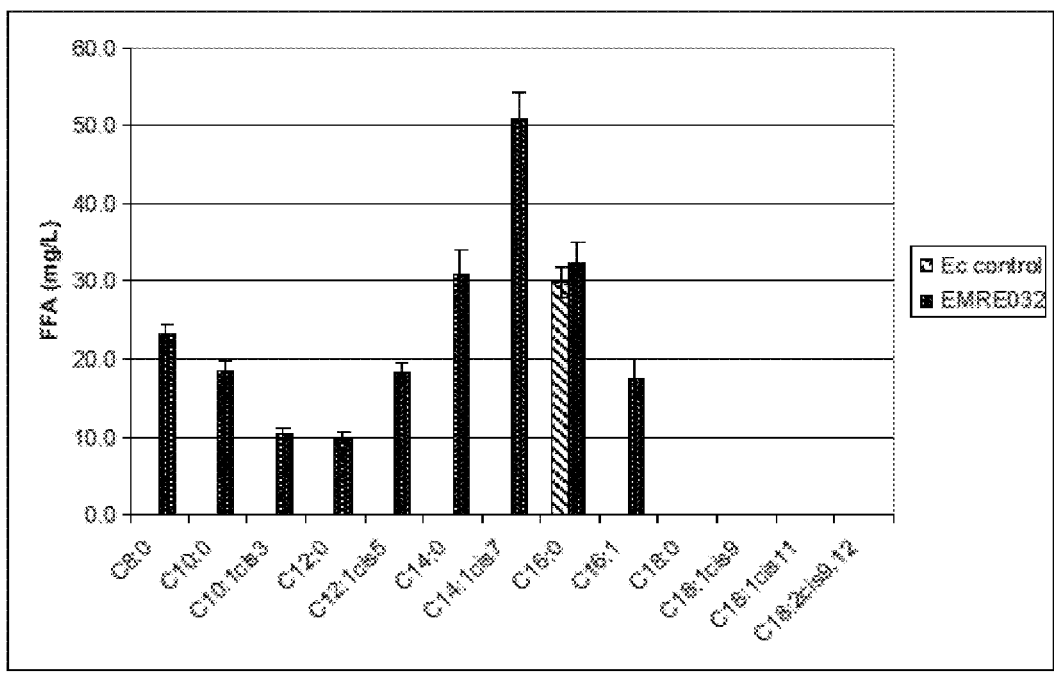
FIG. 4 is a bar chart illustrating the free fatty acids isolated from the culture of Escherichia coli K19 expressing the EMRE032 gene (SEQ ID NO:4) and the profile of the free fatty acids (FFA) isolated from the culture of a control Escherichia coli K19 strain without the EMRE032 gene (Ec control).

Expression of both prokaryotic acyl-ACP thioesterases in *E. coli* led to an increase in free fatty acids in the whole culture (cells plus media) compared to a control culture without the genes. (FIGS. 3 and 4). Moreover, the prokaryotic acyl-ACP thioesterases exhibited distinct substrate specificity when expressed in *E. coli*. Specifically, as shown in FIG. 3, expression of EMRE031 acyl-ACP thioesterase (SEQ ID NO:1) in *E. coli* increased the production of free fatty acids having a chain length of 12 and 14 carbons, whereas EMRE032 acyl-ACP thioesterase (SEQ ID NO:2; FIG. 4) showed highest specificity toward fatty acids having a chain length of 14 carbons in *E. coli*, while also demonstrating activity on fatty acids having an acyl chain length of 8, 10, and 12 carbons, indicating that the two prokaryotic acyl-ACP thioesterases exhibit substrate specificities for fatty acids distinct from each other when expressed in *E. coli*.

Example 5

Transformation of Cyanobacteria

The plasmids containing the EMRE031 (SEQ ID NO:3) and the EMRE032 (SEQ ID NO:4) prokaryotic acyl-ACP thioesterase genes described in Example 2 were introduced into a cyanobacterial host. *Synechocystis* sp. PCC 6803 cells were transformed essentially according to (Zang et al. (2007) J. Microbiology 45:241-245, the content of which is incorporated herein by reference in its entirety). Briefly, cells were grown under constant light to an optical density 730 (O.D. 730) of approximately 0.7 to 0.9 (an OD730 of ~0.25 corresponds to ~1×108 cells/ml) and harvested by centrifugation at ~2,000 g for ~15 mins at room temperature (~20-25° C.). The cell pellet was resuspended in approximately 0.3 times the growth volume of fresh BG-11 medium and used immediately for transformation. About 1 microgram of plasmid DNA (containing the EMRE031 acyl-ACP thioesterase gene (SEQ ID NO:3) or EMRE032 acyl-ACP thioesterase gene (SEQ ID NO:4)) was added to ~0.3 ml of cells, gently mixed, and incubated approximately 5 hours with illumination at ~30° C. without agitation. Cells were spread on a filter (Whatmann Nuclepore Polycarbonate Track-Etched membrane, PC ~47 mm, ~0.2 micron) positioned on a ~50 ml BG-11 agar plates and allowed to recover for about 16 to 24 hours under light, after which the filter was lifted and placed on a fresh BG-11 plate containing spectinomycin (20 µg/ml) to select for transformants. Resulting colonies were screened further for the presence of the thioesterase genes by PCR using the primers used to generate the gene fragments.

Example 6

Culturing Cyanobacteria

*Synechocystis* cells transformed with the EMRE031 and EMRE032 expression constructs were cultured phototrophically, using light as an energy source. Ten ml of BG-11 medium containing 1 mM IPTG in 20 mL glass vials were inoculated at an OD730 nm of 0.6 and grown for 6.5 days (150 rpm) at 30° C. with constant illumination (40 µEinsteins m-2 sec-1). 0.6 ml of culture was removed for biochemical analysis. The ingredients of the BG-11 medium (ATCC medium: 616 Medium BG-11 for blue-green algae) were as follows:

| | | |
|---|---|---|
| NaNO3 | 1.5 | g |
| K2HPO4 | 40 | mg |
| MgSO4•7H2O | 75 | mg |
| CaCl2•2H2O | 36 | mg |
| Citric acid | 6 | mg |
| Ferric ammonium citrate | 6 | mg |
| EDTA | 1 | mg |
| Na2CO3 | 20 | mg |
| Trace Metal Mix A5 (see below) | 1 | ml |
| Agar (if needed) | 10 | g |
| Distilled water | 1 | L |

Adjust final pH to ~7.1
Autoclave at ~121° C. for ~15 minutes.

Trace Metal Mix A5 Composition:

| | | |
|---|---|---|
| H3BO3 | 2.86 | g |
| MnCl2•4H2O | 1.81 | g |
| ZnSO4•7H2O | 0.22 | g |
| Na2MoO4•2H2O | 0.39 | g |
| CuSO4•5H2O | 79.0 | mg |
| Co(NO3)2•6H2O | 49.4 | mg |
| Distilled water | 1 | L |

Example 7

Analysis of Fatty Acid Samples from Cyanobacteria (Synechocystis)

*Synechocystis* fatty acid samples were analyzed on an Agilent model 7890A gas chromatograph equipped with an FID (flame ionization detector) that included a J&W Scientific DB-FFAP capillary column (~15 m length, ~0.25 mm internal diameter, ~0.25 µm film thickness) coupled to an Agilent 5975C mass spectrophotometer. The gas chromatography oven was programmed as follows: ~140° C. for ~0.5 min, then heated at ~20° C./min. to ~230° C. (hold ~5 min). The injector temperature is kept at ~250° C., and a ~40:1 split ~1.0 µl injection was used. Helium was used as a carrier gas at a flow rate of ~1.2 mL/min. The analytes were identified by comparison of retention times to individually injected standards. The calibration range for the analytes was ~2 µg/ml to ~200 µg/ml for C8:0-C16:1 fatty acids and ~0.5 µg/ml to ~50 µg/ml for C18:0-C18:2 fatty acids.

Figure 5:
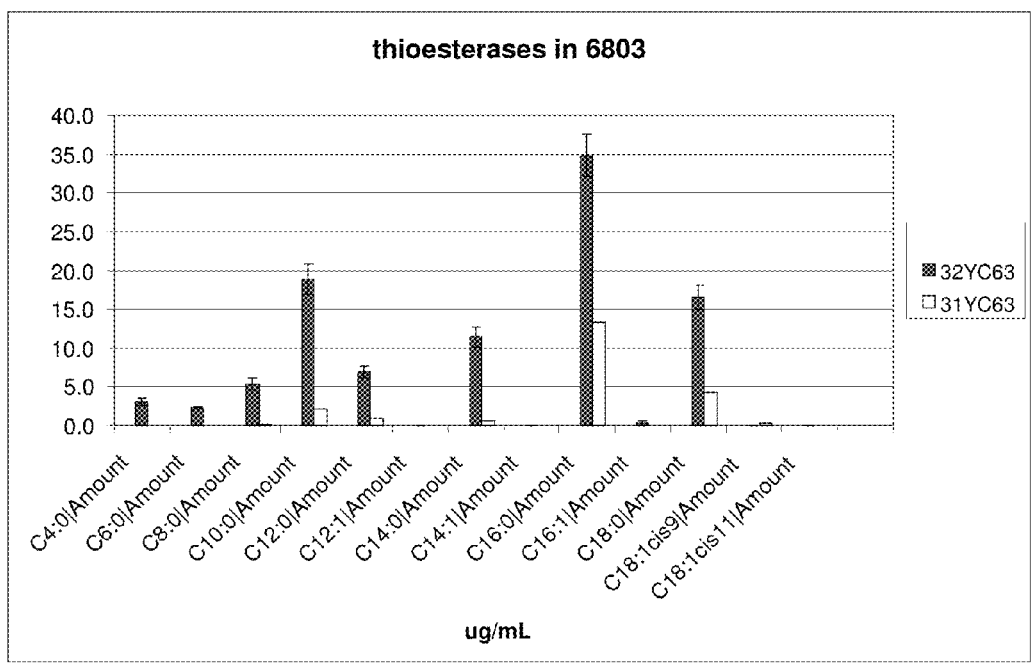
FIG. 5 is a bar chart illustrating the free fatty acids produced by the photosynthetic cyanobacterium Synechocystis sp. PCC 6803 (labeled as 31YC63) expressing the EMRE031 acyl-ACP thioesterase (SEQ ID NO:1) and by the photosynthetic cyanobacteria Synechocystis sp. PCC 6803 (labeled as 32YC63) expressing the EMRE032 acyl-ACP thioesterase (SEQ ID NO:2).

As shown in FIG. 5, expression of prokaryotic acyl-ACP thioesterases EMRE031(SEQ ID NO:1; labeled as 31YC63) and EMRE032 (SEQ ID NO:2; labeled as 32YC63)) led to an increase in free fatty acids with a chain length of 8, 10, 12, 14, 16, and/or 18 carbons in the cyanobacterial cultures (*Synechocystis* sp. PCC 6803). The Y axis indicates the amount of free fatty acids in the sample and the X axis indicates the amount of free fatty acids with different carbon lengths in the sample. The data presented are averaged results of three cultures of each strain. These data indicate that, when expressed in cyanobacteria, both prokaryotic acyl-ACP thioesterases exhibit a distinct substrate specificity (e.g., acyl-ACPs with a chain length of 8, 10, 12, 14, 16 and/or 18 carbons). Approximately 60% of the fatty acids produced by the cyanobacterial strain expressing the EMRE031 acyl-ACP thioesterase were C16 fatty acids, and over 65% (approximately 67%) of the fatty acids produced by the cyanobacterial strain expressing EMRE031 were C12, C14, and C16 fatty acids. The cyanobacterial strain expressing the EMRE032 acyl-ACP thioesterase produced proportionately more C18 fatty acids as compared with the EMRE031 acyl-ACP thioesterase-expressing strain. The EMRE032-expressing strain produced, on average, greater than 35% C16 fatty acids (as a percentage of the total fatty acids produced), with an average of more than 50% (approximately 55%) of the total fatty acids produced by the EMRE032-expressing strain being C12, C14, or C16 fatty acids. Approximately 65% (average of approximately 65.9%) of the fatty acids produced by the EMRE032-expressing strain were C14, C16, or C18 fatty acids.

It should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A photosynthetic microorganism comprising a nucleic acid molecule encoding an exogenous acyl-acyl carrier protein (acyl-ACP) thioesterase selected from the group consisting of SEQ ID NO: 1, SEQ ID NO:2, and variants thereof having at least 80% amino acid sequence identity to the amino acid sequence of SEQ ID NO:1 or 2, wherein the acyl-ACP thioesterase, when queried against Pfam database hidden Markov models, demonstrates inclusion in Pfam PF01643 with a bit score higher than 20.3 and an E-value of less than or equal to 0.01, and wherein the photosynthetic microorganism produces at least one free fatty acid, and further wherein greater than 35% of the at least one free fatty acid or fatty acid derivative produced by the photosynthetic microorganism has a chain length of 16 carbons.

2. The photosynthetic microorganism according to claim 1, wherein the photosynthetic microorganism further produces at least one fatty acid derivative comprising at least one fatty aldehyde, at least one fatty alcohol, at least one fatty acid ester, at least one wax ester, at least one alkane, at least one alkene, or a combination thereof.

3. The photosynthetic microorganism according to claim 2, wherein the photosynthetic microorganism produces at least one wax ester having a total number of carbons from 16 to 36.

4. The photosynthetic microorganism according to claim 2, wherein the photosynthetic microorganism produces at least one free fatty acid, at least one fatty aldehyde, at least one fatty alcohol, at least one alkane, or at least one alkene having a carbon chain length of from 8 to 24 carbons.

5. The photosynthetic microorganism according to claim 4, wherein at least one free fatty acid, at least one fatty aldehyde, at least one fatty alcohol, at least one alkane, or at least one alkene produced by the photosynthetic microorganism has a chain length of from 12 to 16 carbons.

6. The photosynthetic microorganism according to claim 4, wherein at least 50% of the at least one free fatty acid, at least one fatty aldehyde, at least one fatty alcohol, at least one alkane, or at least one alkene produced by the photosynthetic microorganism has a chain length of from 12 to 16 carbons.

7. The photosynthetic microorganism according to claim 1, wherein the photosynthetic microorganism is a microalga.

8. The photosynthetic microorganism according to claim 7, wherein the photosynthetic microorganism is of a genus selected from the group consisting of Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella, and Volvox.

9. The photosynthetic microorganism according to claim 1, wherein the photosynthetic microorganism is a cyanobacterium.

10. The photosynthetic microorganism according to claim 9, wherein the photosynthetic microorganism is of a genus selected from the group consisting of Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema, and Xenococcus.

11. A method for producing a free fatty acid or fatty acid derivative in a culture, the method comprising culturing the photosynthetic microorganism of claim 1 in a growth medium,
wherein the photosynthetic microorganism is cultured under conditions that allow for expression of the exogenous acyl-ACP thioesterase in the photosynthetic microorganism; and
wherein the expression of the exogenous acyl-ACP thioesterase in the photosynthetic microorganism results in production of at least one free fatty acid or at least one fatty acid derivative.

12. The method according to claim 11, wherein the at least one fatty acid derivative comprises at least one fatty aldehyde, at least one fatty alcohol, at least one fatty acid ester, at least one wax ester, at least one alkane, at least one alkene, or a combination thereof.

13. The method according to claim 11, wherein the growth medium does not include a reduced carbon source.

14. The method according to claim 11, wherein the method further comprises isolating the at least one free fatty acid or fatty acid derivative from the culture.

15. The method according to claim 11, wherein the photosynthetic microorganism is a microalga.

16. The method according to claim 15, wherein the photosynthetic microorganism is of a genus selected from the group consisting of Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella,

*Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox.*

17. The method according to claim 11, wherein the photosynthetic microorganism is a cyanobacterium.

18. The method according to claim 17, wherein the photosynthetic microorganism is of a genus selected from the group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.*

19. The photosynthetic microorganism according to claim 6, wherein at least 30 wt % of the at least one free fatty acid, at least one fatty aldehyde, at least one fatty alcohol, at least one alkane, or at least one alkene produced by the photosynthetic microorganism has a chain length of 16 carbons.

20. The photosynthetic microorganism according to claim 1, wherein the exogenous acyl-ACP thioesterase is selected from the group consisting of: SEQ ID NO:1, SEQ ID NO:2, and variants thereof having at least 85% amino acid sequence identity to the amino acid sequence of SEQ ID NO:1 or 2.

21. A photosynthetic microorganism comprising a nucleic acid molecule encoding an exogenous acyl-acyl carrier protein (acyl-ACP) thioesterase selected from the group consisting of SEQ ID NO: 1, SEQ ID NO:2, and variants thereof having at least 80% amino acid sequence identity to the amino acid sequence of SEQ ID NO:1 or 2, wherein the acyl-ACP thioesterase, when queried against Pfam database hidden Markov models, demonstrates inclusion in Pfam PF01643 with a bit score higher than 20.3 and an E-value of less than or equal to 0.01, and wherein the photosynthetic microorganism produces at least 30 wt % of at least one fatty acid derivative having a chain length of 16 carbons.

\* \* \* \* \*